(12) United States Patent
Kodanko et al.

(10) Patent No.: US 9,593,138 B2
(45) Date of Patent: Mar. 14, 2017

(54) NITRILE-CONTAINING ENZYME INHIBITORS AND RUTHENIUM COMPLEXES THEREOF

(71) Applicants: Wayne State University, Detroit, MI (US); Ohio State Innovation Foundation, Columbus, OH (US)

(72) Inventors: Jeremy J. Kodanko, Grosse Pointe Park, MI (US); Claudia Turro, Columbus, OH (US)

(73) Assignees: Wayne State University, Detroit, MI (US); Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 13/998,148

(22) Filed: Oct. 7, 2013

(65) Prior Publication Data

US 2014/0100173 A1    Apr. 10, 2014

Related U.S. Application Data

(60) Provisional application No. 61/710,552, filed on Oct. 5, 2012.

(51) Int. Cl.
C07F 15/00 (2006.01)

(52) U.S. Cl.
CPC ................................ C07F 15/0053 (2013.01)

(58) Field of Classification Search
None
See application file for complete search history.

(56) References Cited

U.S. PATENT DOCUMENTS

| | | | |
|---|---|---|---|
| 5,445,608 | A | 8/1995 | Chen et al. |
| 5,637,479 | A * | 6/1997 | Rubin et al. ........... 435/69.2 |
| 5,766,234 | A | 6/1998 | Chen et al. |
| 5,800,478 | A | 9/1998 | Chen et al. |
| 5,876,427 | A | 3/1999 | Chen et al. |
| 6,416,531 | B2 | 7/2002 | Chen |
| 6,445,011 | B1 | 9/2002 | Hirano et al. |
| 6,784,460 | B2 | 8/2004 | Ng et al. |
| 6,958,498 | B2 | 10/2005 | Shelton et al. |
| 8,063,216 | B2 | 11/2011 | Etchenique et al. |
| 8,338,600 | B2 | 12/2012 | Schindler et al. |
| 2007/0191392 | A1 | 8/2007 | Missbach |
| 2007/0197510 | A1 | 8/2007 | Ohmoto et al. |
| 2009/0216300 | A1 | 8/2009 | Keltner et al. |
| 2010/0145415 | A1 | 6/2010 | Dahm et al. |
| 2012/0220922 | A1 | 8/2012 | Yuste et al. |
| 2014/0100173 | A1 * | 4/2014 | Kodanko et al. ........... 514/20.1 |

OTHER PUBLICATIONS

Respondek et al. Light Activation of a Cysteine Protease Inhibitor: Caging of a Peptidomimetic Nitrile with RuII(bpy)2. Journal of the American Chemical Society (Oct. 5, 2011), 133(43), 17164-17167.*
Garner et al. [Ru(bpy)2(5-cyanouracil)2]2+ as a Potential Light-Activated Dual-Action Therapeutic Agent. Inorganic Chemistry (Aug. 3, 2011), 50(19), 9213-9215.*
Abouelatta et al., "Synthesis, Characterization, and Theoretical Studies of Metal Complexes Derived from the Chiral Tripyridyldiamine Ligand Bn-CDPy3," Inorg. Chem. (2010) 49: 5202-5211.
Altmann et al., "Dipeptide nitrile inhibitors of cathepsin K," Bioorg. Med. Chem. Lett. (Feb. 9, 2006) 16: 2549-2554.
Barton et al., "Chiral Discrimination in the Covalent Binding of Bis (phenanthroline) Dichlororuthenium (II) to B-DNA," J. Am. Chem. Soc. (1985) 107: 709-711.
Boxer et al. "A Highly Potent and Selective Caspase 1 Inhibitor that Utilizes a Key 3-Cyanopropanoic Acid Moiety," NIH Public Access Author Manuscript (May 3, 2010) 5 (5): 730-738.
Filevich et al., "Fast Optical pH Manipulation and Imaging," Anal. Chem. (Jun. 6, 2012) 84: 5618-5624.
Fleming et al., "Nitrile-Containing Pharmaceuticals: Efficacious Roles of the Nitrile Pharmacophore," NIH Public Access Author Manuscript (Nov. 25, 2010) 53 (22): 7902-7917.
Frizler et al., "Development of Nitrile-Based Peptidic Inhibitors of Cysteine Cathepsins," Curr. Top. Med. Chem. (2010) 10: 294-322.
Gauthier et al., "The discovery of odanacatib (MK-0822), a selective inhibitor of cathepsin K," Bioorg. Med. Chem. Lett. (Jan. 15, 2008) 18: 923-928.
Greenspan et al., "Identification of Dipeptidyl Nitriles as Potent and Selective Inhibitors of Cathepsin B through Structure-Based Drug Design," J. Med. Chem. (Nov. 14, 2001) 44: 4524-4534.
Grover et al., "Stereoselective Covalent Binding of Aquaruthenium (II) Complexes to DNA," J. Am. Chem. Soc. (1992) 114: 3390-3393.
Jabre et al., "A Divergent Strategy for Attaching Polypyridyl Ligands to Peptides," J. Org. Chem (Jan. 5, 2010) 75: 650-659.
Jabre et al., "A Highly Divergent Approach for Synthesis of Metal-Binding Peptide Libraries," J. Org. Chem. (2011) 76: 2273-2276.
Loser et al., "Interaction of Papain-like Cysteine Proteases with Dipeptide-Derived Nitriles," J. Med. Chem. (Nov. 3, 2005) 48: 7688-7707.
Priestman et al., "Merging of Confocal and Caging Technologies: Selective Three-Color Communication with Profluorescent Reporters," Angew. Chem. Int. Ed. (2012) 51: 7654-7687.
Salierno et al., "Caged Amino Acids for Visible-Light Photodelivery," Eur. J. Inorg. Chem. (2008) 1125-1128.
Sgambellone et al., "Cellular Toxicity Induced by the Photorelease of a Caged Bioactive Molecule: Design of a Potential Dual-Action Ru(II) Complex," J. Am. Chem. Soc. (2013) 135 (30): 11274-11282.
Singh et al., "Photoinitiated DNA Binding by cis-[Ru(bpy)2(NH3)2]2+," Inorg. Chem. (2004) 43: 7260-7262.
Garner et al., "[Ru(bpy)2(5-cyanouracil)2]2+ as a Potential Light-Activated Dual-Action Therapeutic Agent," Inorg. Chem. (Aug. 31, 2011) 50: 9213-9215.
Zayat et al., "A New Inorganic Photolabile Protecting Group for Highly Efficient Visible Light GABA Uncaging," ChemBioChem (2007) 8: 2035-2038.
Zayat et al., "A New Strategy for Neurochemical Photodelivery: Metal-Ligand Heterolytic Cleavage," J. Am. Chem. Soc. (Jan. 1, 2003) 125: 882-883.

* cited by examiner

*Primary Examiner* — Maury Audet
(74) *Attorney, Agent, or Firm* — Billion & Armitage; Patti J. Jurkovich

(57) ABSTRACT

The invention provides nitrile-containing protease inhibitors caged to ruthenium compounds. The nitrile-caged ruthenium compounds provide inactivated inhibitors that can be delivered to surface or site for activation, for example, but exposure to light. The invention also provides methods for delivering protease inhibitors to subjects for the therapeutic treatment of conditions such as cancer.

9 Claims, 25 Drawing Sheets
(16 of 25 Drawing Sheet(s) Filed in Color)

(15-1)

(15-2)

(15-3)

(15-4)

17A

17B

17C

17D

A.

B.

NITRILE-CONTAINING ENZYME INHIBITORS AND RUTHENIUM COMPLEXES THEREOF

RELATED APPLICATIONS

This application claims priority under 35 U.S.C. §119(e) to U.S. Provisional Patent Application No. 61/710,552, filed Oct. 5, 2012, which is incorporated herein by reference.

GOVERNMENT SUPPORT

This invention was made with government support under CHE-0911354 and CHE-1213646 awarded by the National Science Foundation and GM 833552 and EB016072 awarded by the National Institutes of Health. The government has certain rights in the invention.

BACKGROUND OF THE INVENTION

Cysteine cathepsins and caspases are a class of cystein proteases which are associated with regulation of apoptosis, inflammation and cancer. Cysteine cathepsins and caspases are overexpressed in a variety of cancers. Downregulation and gene knockout studies in mice support a causal role for cysteine proteases in tumor growth, migration, invasion, angiogenesis and metastasis. Because of their broad pro-tumorigenic activities, these enzymes are considered viable targets for chemotherapy. However, cathepsins are necessary for normal cell function so selective inhibition within cancerous tissue would be beneficial to achieve high levels of therapeutic selectivity and to avoid systemic toxicity issues found with many cysteine cathepsin inhibitors.

Thus, compounds that enable the selective inhibition of cathepsins within cancerous tissue are needed. Delivery methods and techniques for enhancing or activating the selective inhibition of cathepsins are also needed.

SUMMARY

The invention provides biological compounds that are masked in dark and can be unmasked when irradiated with suitable light. These compounds are stable in the dark and can rapidly release the active molecules when irradiated with light. Preferably, the compounds have a high dark to light activity ratio.

The masked or caged biological compounds can be triggered by release with light to provide a method that yields spatial and kinetic control over compound activation. Light activated compounds can be used as drugs in photodynamic therapy because lasers and fiber optics make it possible for light to reach almost any tissue in the human body. The invention provides compounds having caged cysteine protease inhibitors and methods for their release. For example, a peptidomimetic nitrile-based inhibitor can be rendered inert through binding to a ruthenium center. Upon photolysis, the nitrile-based inhibitor can be unleashed, providing high levels of selectivity for enzyme inhibition under light vs. dark conditions. This strategy was proven effective against purified enzymes and in lysates.

Accordingly, the invention provides a compound of Formula I:

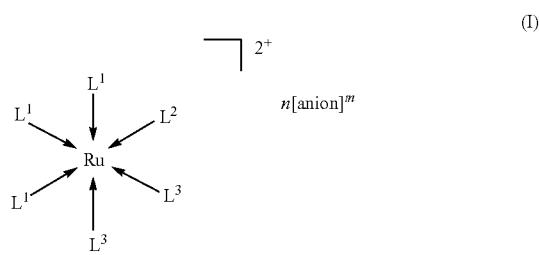

wherein each $L^1$ is independently a nitrogen-containing ruthenium ligand, each $L^2$ is an enzyme inhibitor, and each $L^3$ can be $L^1$ or $L^2$, and $L^1$ groups can be monodentate ligands, or two or more can combine to form bidentate, tridentate, tetradentate, or pentadentate ruthenium ligands. For example, in some embodiments, two $L^1$ groups optionally form a bidentate ligand, three $L^1$ groups optionally form a tridentate ligand, four $L^1$ groups optionally form a tetradentate ligand, or five $L^1$ groups optionally form a pentadentate ligand. Each $L^2$ can be a nitrile-containing protease inhibitor, for example, having the formula R—CN, or one $L^2$ is a protease inhibitor and the other $L^2$ is a solvent molecule or anion coordinated to ruthenium. When both $L^2$ are protease inhibitors, R—CN of each $L^{-2}$ can be the same or different. The group n[anion]$^m$ is a pharmaceutically acceptable anion where n is $-1$, or n is 1 and m is $-2$. In some embodiments, n[anion]$^m$ is $2PF_6^-$.

The ruthenium metal center can have one, two, or three nitrile compound ligands, and the remaining ligands can be any combination of monodentate, bidentate, tridentate, tetradentate, or pentadentate ruthenium ligands, in any combination to fit the structural aspects of Formula I. For example, in various embodiments, the ligands $L^1$ of Formula I can be:
  a) two $L^1$ groups form a bpy ligand and Formula I comprises two bpy ligands;
  b) two $L^1$ groups form a phen ligand and Formula I comprises two phen ligands;
  c) two $L^1$ groups form a biq ligand and Formula I comprises two biq ligands;
  d) two $L^1$ groups form a biq ligand and two $L^1$ groups form a phen ligand;
  e) three $L^1$ groups form a tpy ligand;
  f) four $L^1$ groups form a TPA ligand; or
  g) five $L^1$ groups form an N4Py ligand.
Other combinations of these ligands and other ligands described herein will be readily apparent to those of skill in the art.

In various embodiments, the compound of Formula I can be a compound of Formula II:

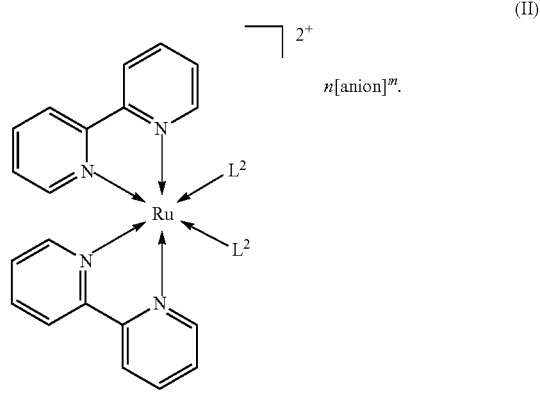

As discussed above, each $L^2$ can be a nitrile-containing protease inhibitor, for example, having the formula R—CN. The group R—CN can be any suitable protease inhibitor. Examples of specific $L^2$ groups include, but are not limited to, the nitrile compounds described herein such as balicatib, L-006235, L-873724, MK-1256, nilvadipine, odanacatib, saxagliptin, or vildagliptin.

The group, R, can be dipeptide, tripeptide, tetrapeptide, oligopeptides, or polypeptide conjugated to the —CN groups through a direct bond, a methylene group, or a linker comprising an optionally functionalized ($C_1$-$C_{20}$)alkyl group or ($C_3$-$C_{16}$)cycloalkyl group.

The invention also provides a method for rendering a protease inhibitor substantially inactive, or significantly less active, comprising contacting a protease inhibitor that comprises a nitrile group and a $Ru^{II}$ complex, in the presence of a suitable organic solvent and an oxidant, thereby forming a $Ru^{II}$ compound comprising two equivalents of the protease inhibitor as ligands of the $Ru^{II}$ compound. The $Ru^{II}$ compound formed can be, for example, a compound described herein.

The invention further provides a method of delivering a nitrile-containing protease inhibitor to a surface or a cell comprising irradiating a compound described herein with light or a sufficient amount of electromagnetic radiation. The light can be visible light or near-IR light, for example, electromagnetic radiation having wavelengths of about 350 nm to about 1100 nm. In some embodiments, the light can have a wavelength of, for example, about 390 nm to about 400 nm, or about 395 nm. In some embodiments, the surface is bone and/or the cell is a cancer cell.

In a specific embodiment, R—CN is:

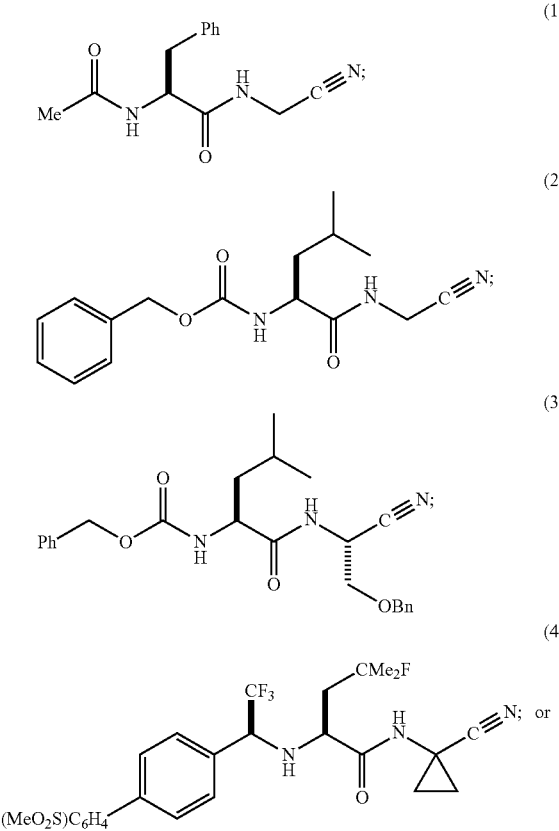

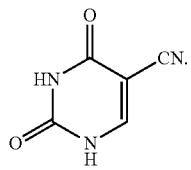

The invention thus provides novel compounds of the formulas described herein, as well as methods of preparing compounds of the formulas described herein. The invention also provides compounds of the formulas described herein that are useful as intermediates for the synthesis of other useful compounds. The invention further provides for the use of compounds of the formulas described herein for the manufacture of medicaments useful for the treatment of diseases in a mammal, for example, cancer in a human. The medicament can include a pharmaceutically acceptable diluent, excipient, or carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 15-1) buffer control plus light; 15-2) 3 (250 nM) plus light; 15-3) 3 (250 nM), no light; and 15-4) cis-[Ru(bpy)$_2$(MeCN)$_2$](PF$_6$)$_2$ (250 nM, ruthenium control) plus light. For each of 15-1, 15-2, 15-3, and 15-4, panels are A) green fluorescence of cleaved substrate due to active cathepsin K; B) DIC image; C) blue fluorescence due to DAPI nuclear stain; and D) DIC image merged with green and blue fluorescence demonstrating the intracellular cathepsin K activity.

Panels are A) green fluorescence of cleaved substrate due to active cathepsin K; B) DIC image; C) blue fluorescence due to DAPI nuclear stain; and D) DIC image merged with green and blue fluorescence demonstrating the intracellular cathepsin K activity.

Figure 16:
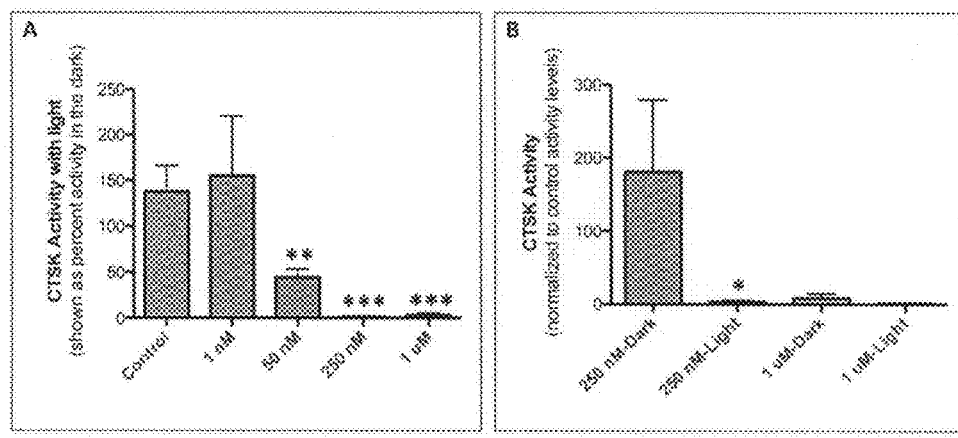

FIG. 16. A) CTSK activity with light; and B) CTSK activity normalized to control activity levels.

Figure 17:
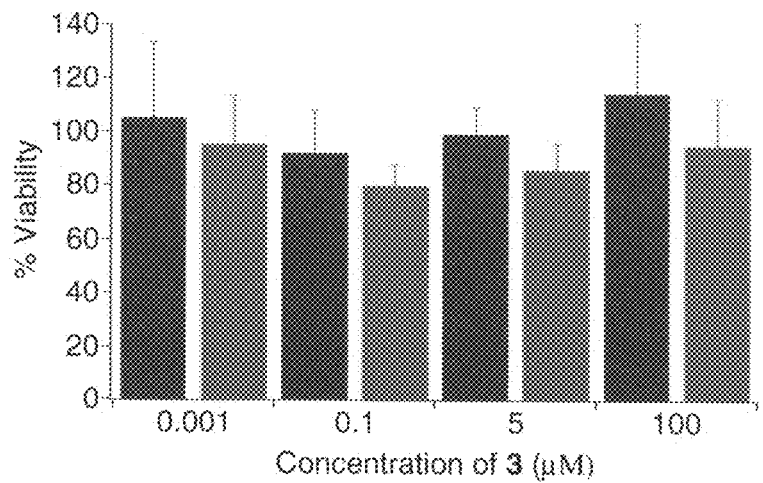
Figure 17:
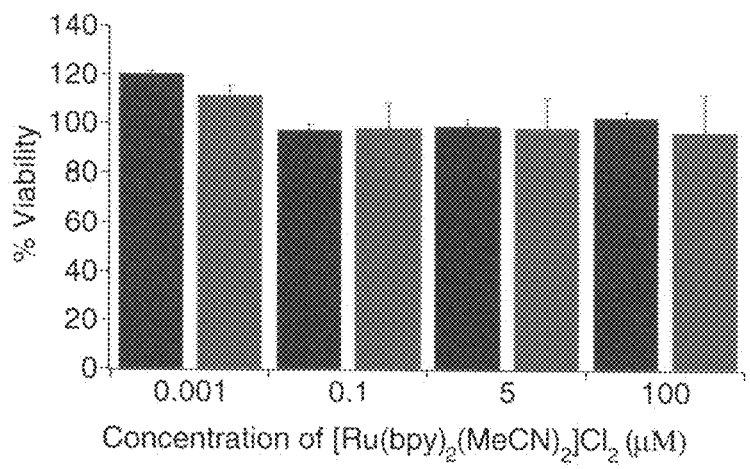
Figure 17:
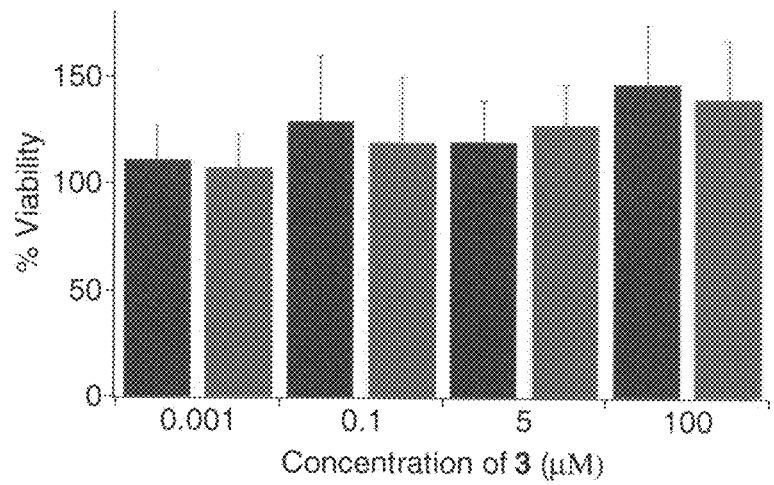
Figure 17:
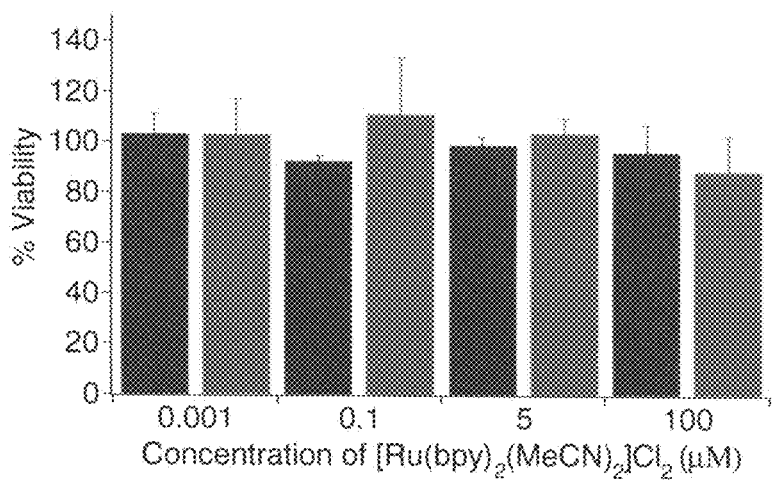

FIG. 17. Cytotoxicity of cis-[Ru(bpy)$_2$(2)$_2$]Cl$_2$ (VI) and the control compound cis-[Ru(bpy)$_2$(MeCN)$_2$](PF$_6$)$_2$ on BMM cells (A-B) and prostate cancer PC3 cells (C-D).

Figure 18:
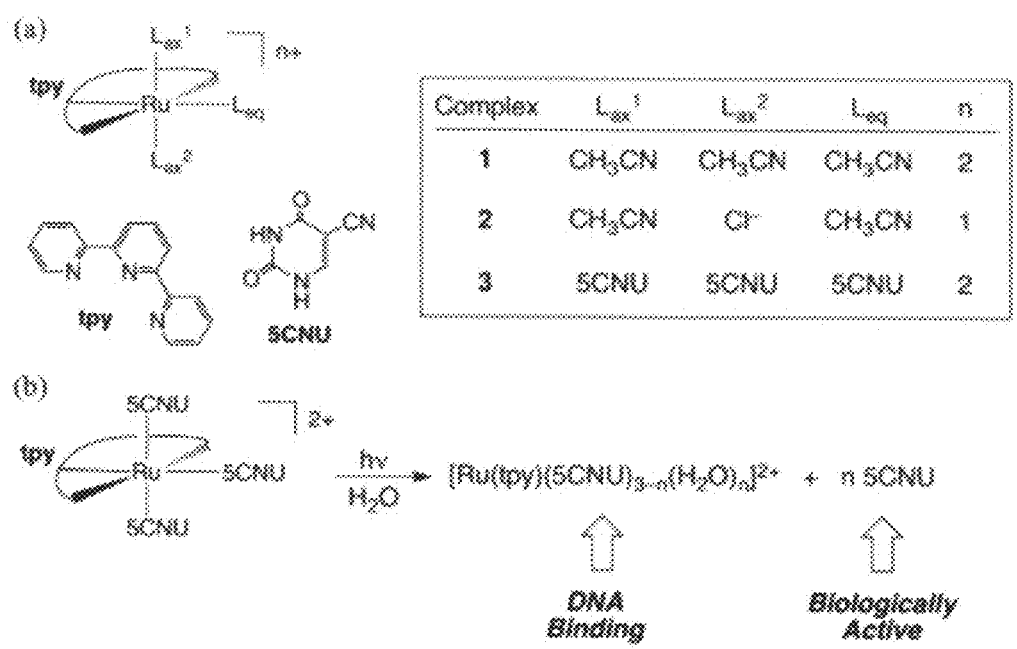

FIG. 18. (a) Schematic representation of the molecular structures from Example 8, of 1-3, tpy, and 5CNU, and (b) photorelease of a metal complex able to bind DNA and of the biologically active 5CNU molecule through irradiation with visible light in water.

Figure 19:
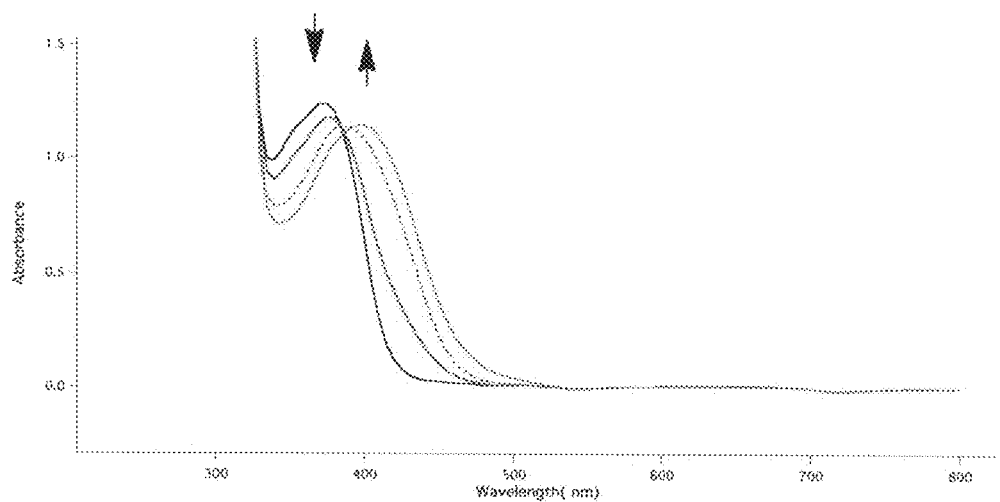

FIG. 19. Changes in electronic absorption spectrum of [Ru(TPA)(MeCN)$_2$](PF$_6$)$_2$ (compound 1 of Example 10) in 10:1 acetone:H$_2$O upon irradiation with long-range handheld TCL lamp (~365 nm light (8 W)) at $t_{irra}$=0 (black), 5 (red), 15 (green), and 100 (pink) minutes.

Figure 20:
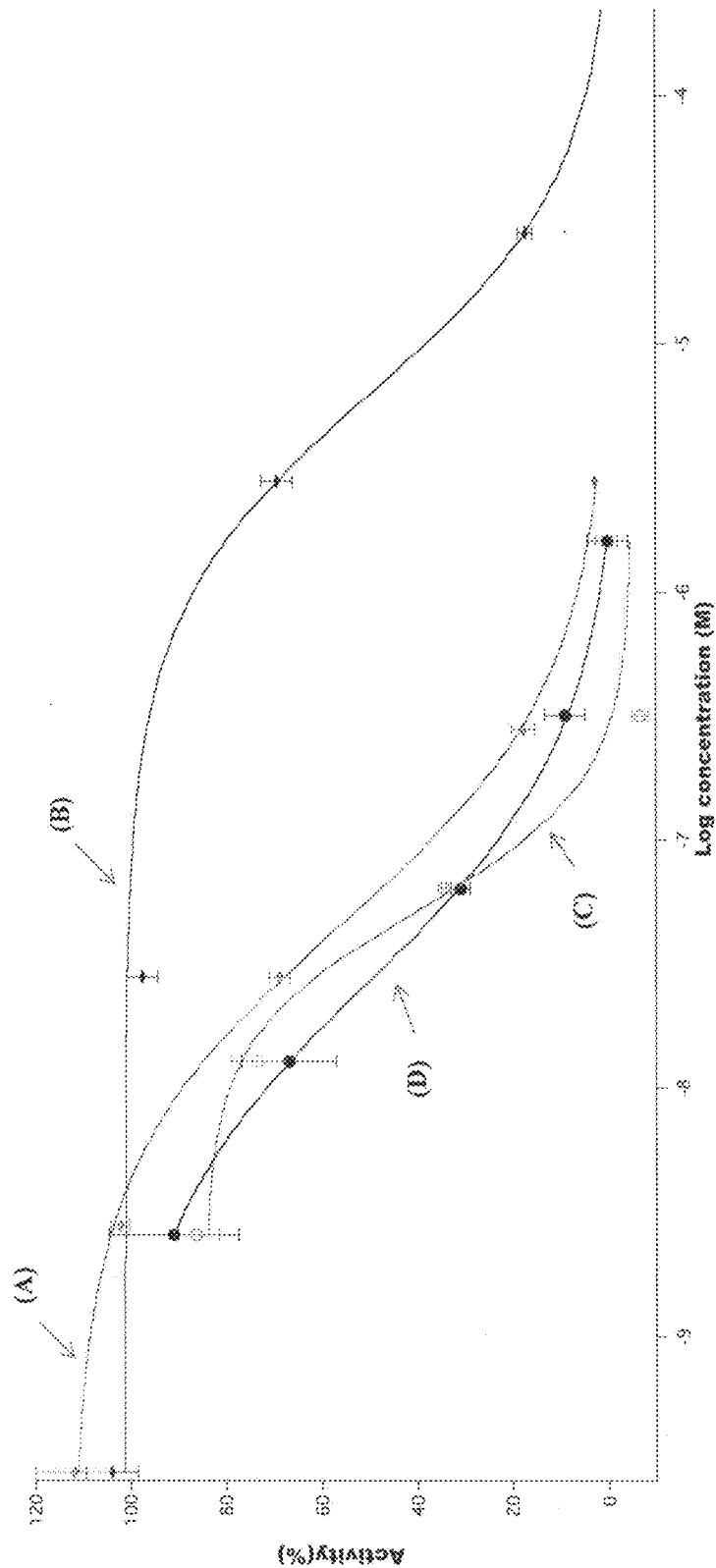

FIG. 20. IC$_{50}$ curves for Ru-caged inhibitor 2 of Example 10 ((A), with irradiation, and (B), without irradiation) and uncaged inhibitor 3 ((C), with irradiation, and (D), without irradiation) against human cathepsin K.

Figure 21:
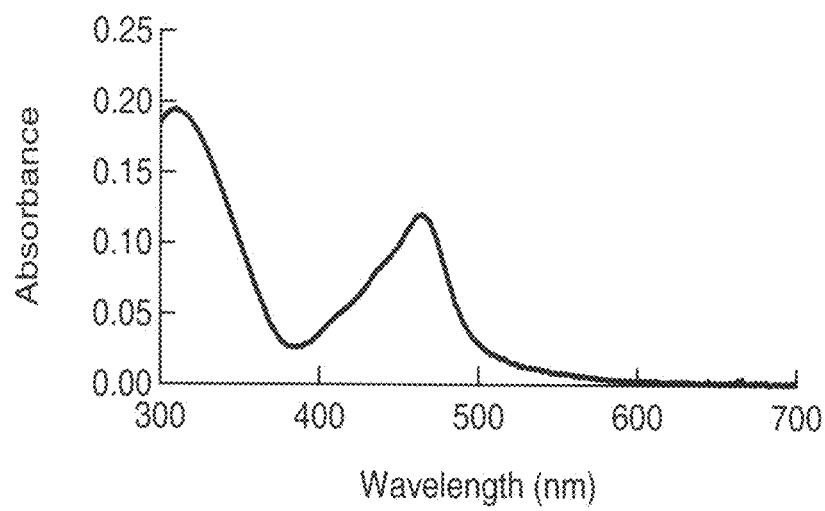

FIG. 21. Electronic Absorption in CH$_3$CN of cis-[Ru(PTPI)$_2$(CH$_3$CN)$_2$]$^{2+}$ showing the red-shift of the absorption and the tail that extends to 600 nm.

Figure 22:
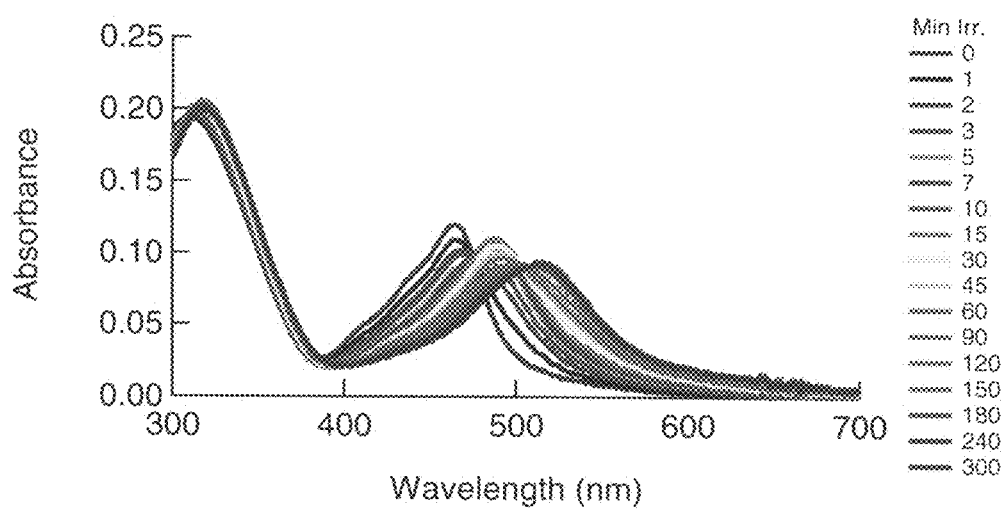

FIG. 22. Photolysis of cis-[Ru(PTPI)$_2$(CH$_3$CN)$_2$]$^{2+}$ in H$_2$O, $l_{irr}$≥495 nm showing the sequential exchange of the CH$_3$CN ligands bound to the metal for water molecules, thus releasing two equivalents of bound nitrile. The exchange of one ligand is complete after 10 minutes of irradiation (green curve) and the release of the second ligand is complete after ~2 hours (120 min) of irradiation.

Figure 23:
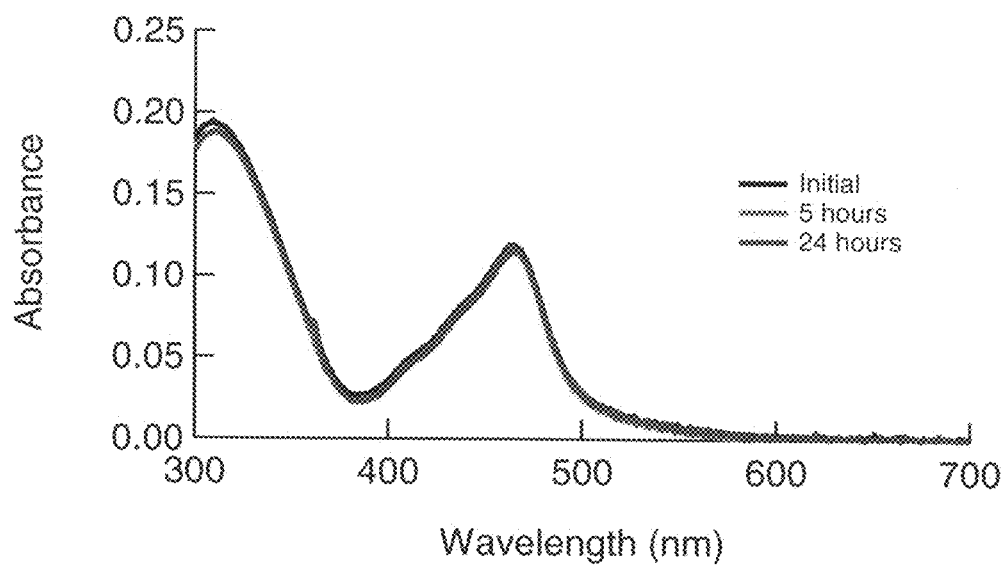

FIG. 23. Dark Control with respect to FIG. 22 showing that the nitrile ligands are not released under similar conditions in the absence of light for a period of 24 hours.

Figure 24:
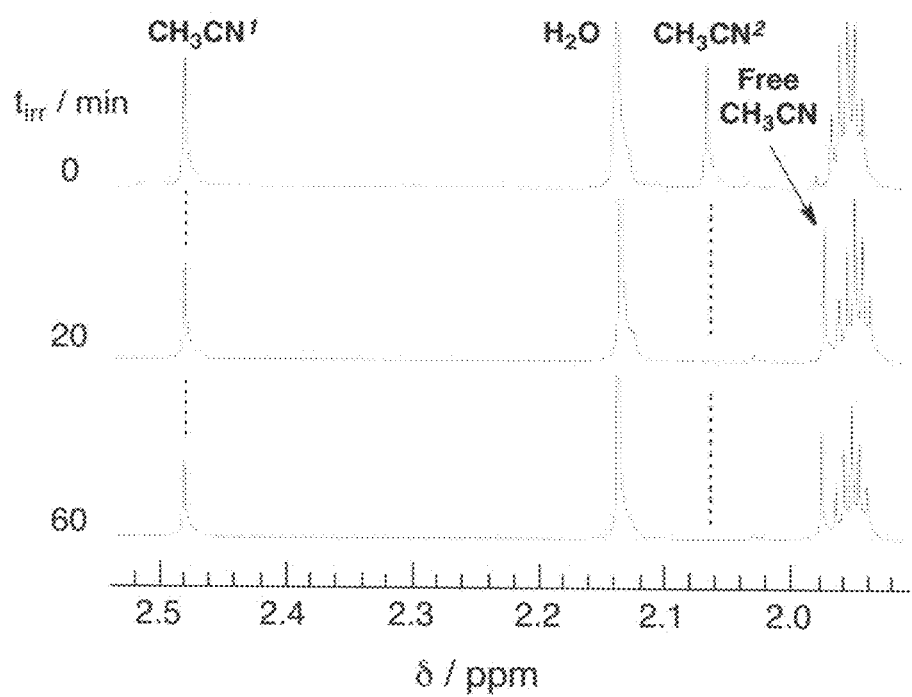

FIG. 24. Changes to the $^1$H NMR spectrum of 12.1 upon irradiation in CD$_3$CN using benzene as an internal integration standard.

Figure 25:
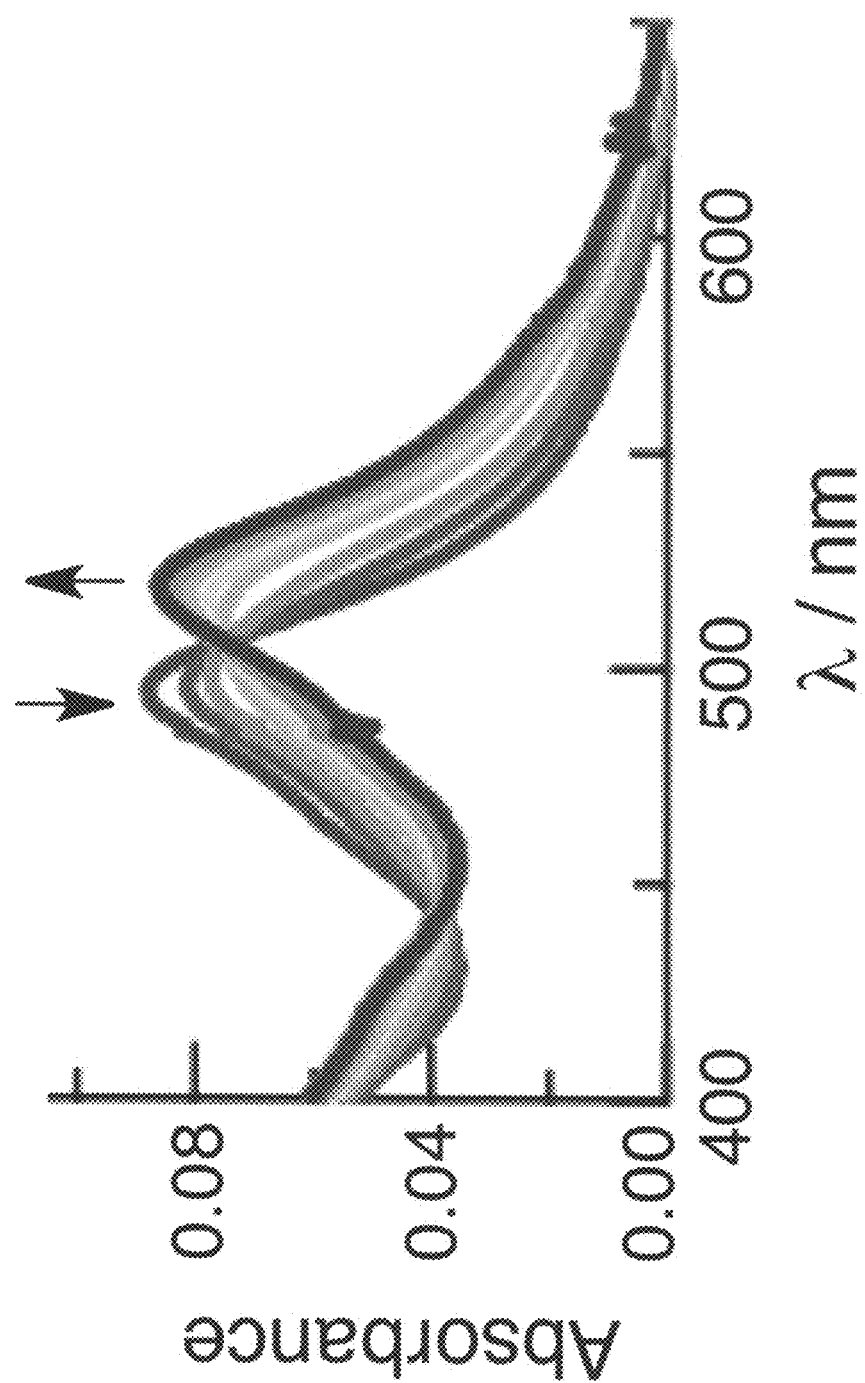

FIG. 25. Changes to the electronic absorption spectrum of 12.1 (10 µM) in H$_2$O upon irradiation for 0-20 min ($\lambda_{irr}$≥550 nm).

Figure 26:
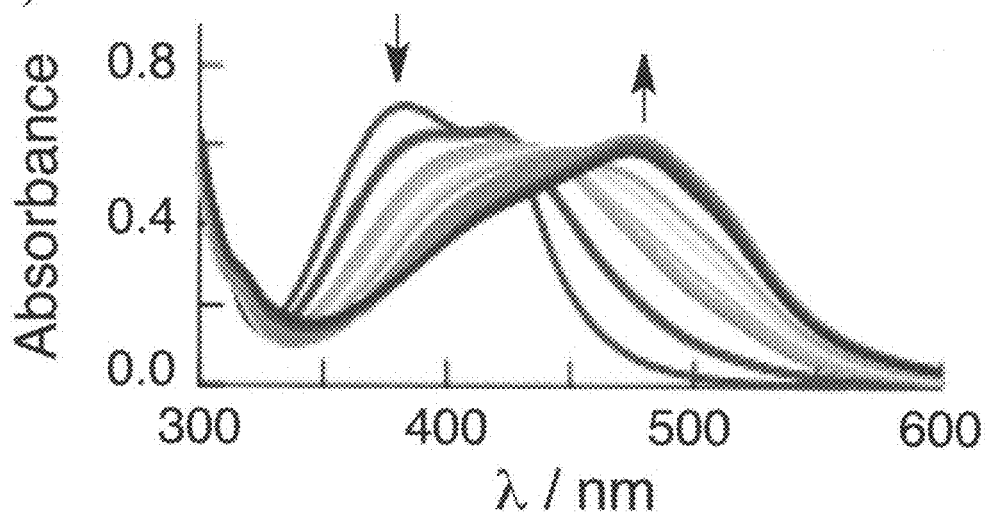
Figure 26:
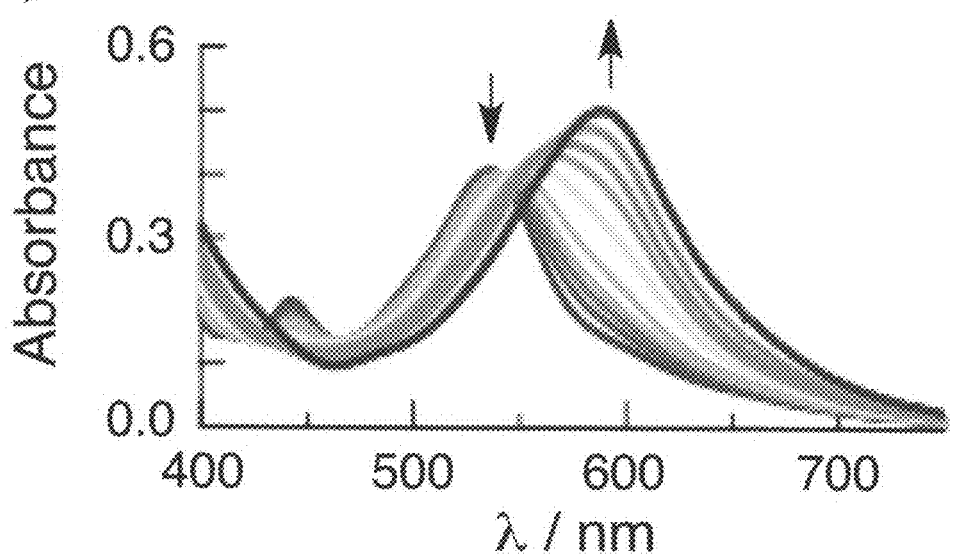

FIG. 26. Irradiation of (a) 50 µM 12.2 ($\lambda_{irr}$≥420 nm, 0-90 min) and (b) 60 µM 12.3 ($\lambda_{irr}$≥610 nm, 0-120 min) in H$_2$O.

Figure 27:
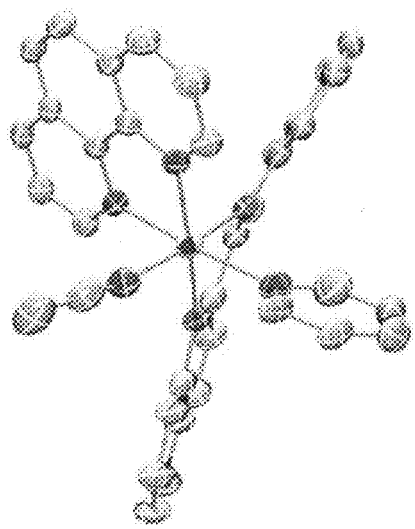
Figure 27:
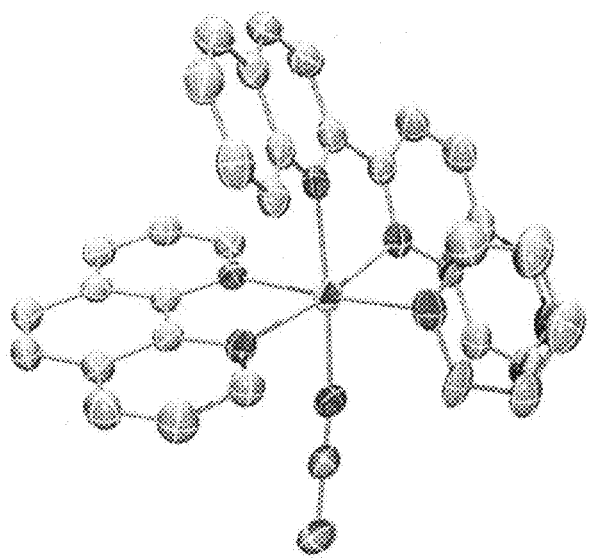

FIG. 27. ORTEP plots of two different perspectives ((a), perspective 1; (b), perspective 2) of PF$_6^-$ salt of the monosubstituted intermediate 12.6 (ellipsoids drawn at 50% probability).

Figure 28:
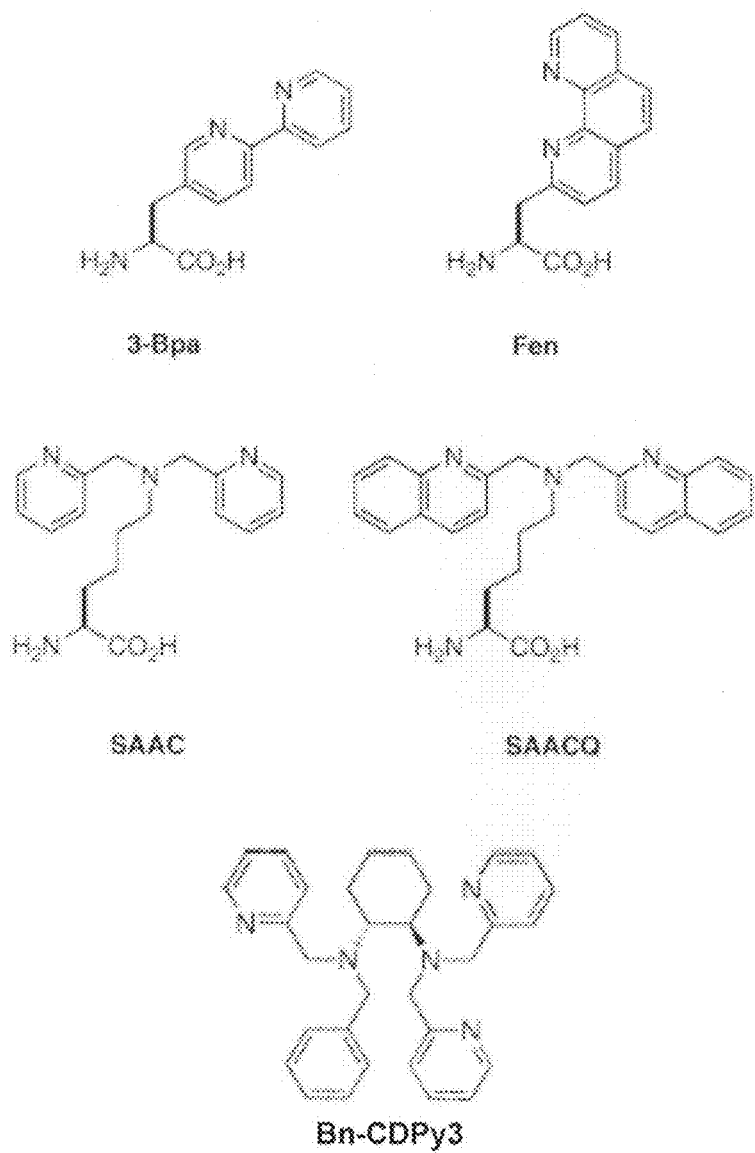
Figure 28:
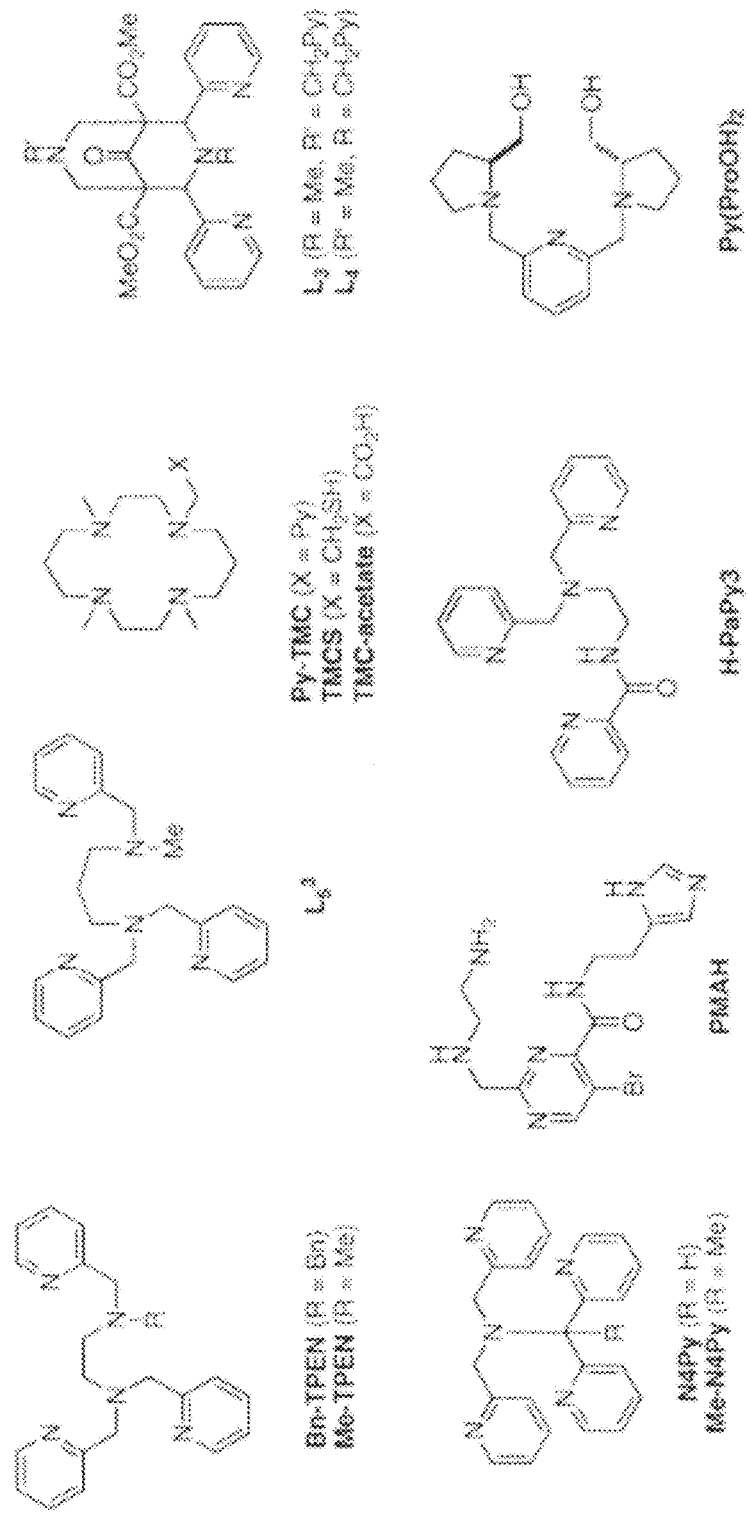

FIG. 28. Ruthenium ligands, according to various embodiments.

DETAILED DESCRIPTION

Serine and cysteine proteases are ubiquitous in nature and play major roles in many human disease states. Cysteine proteases play a major role in the physiology, growth and development. They are involved in senescence, protein accumulation and mobilization, cell signaling and programmed cell death (apoptosis), extracellular matrix remodeling, pro-hormone processing, and inflammation. Serine proteases evolved from their role in digestion in lower organisms to regulate blood clotting, the immune system, and inflammation in humans.

A method for ligating, or "caging", protease inhibitors, including cysteine and serine protease inhibitors is provided. Binding to a ruthenium center renders nitrile-based protease inhibitors inert and unable to react with active site cysteines or series of proteases, which diminishes the ability of caged inhibitors to bind to the enzyme target. Upon photoactivation, two molecules of the nitrile-based protease inhibitor are released from the ruthenium center, which makes the inhibitor able to bind to its target protein and inhibit proteolysis. This method therefore provides a general approach toward light activation of serine and cysteine protease inhibitors. Also, the released protease inhibitors (ligands) when released from the Ru$^{II}$ complex often have twice the activity of the protease inhibitors when administered without the Ru$^{II}$ complexing agent.

Enzyme inhibitors are extremely useful tools for chemical biology and are important clinical therapeutic agents. There are few known examples of light-activated enzyme inhibitors. A variety of techniques are available to block enzyme activity, but none of them can provide the level of spatial and kinetic control of light activation. Established methods such as RNA interference (RNAi) and the creation of transgenic animals do not allow for time-resolved studies to determine the effect of enzyme knockouts. Using even the most specific enzyme inhibitors, there is no way to control spatial activation in tissue or cell culture. The invention described herein thus fills this unmet need of allowing protease inhibitors to be activated with light in a temporally and spatially controlled fashion that exceeds the capabilities of microinjection or perfusion.

The disclosed compounds can also be used for the development and evaluation of biological reagents. For therapeutic applications, the compounds and methods allow for the localized activation of protease inhibitors within live animals, including humans. This is important because proteases are considered viable targets for cancer chemotherapy. However, proteases are necessary for normal cell function, so selective inhibition within cancerous tissue would be beneficial to achieve high levels of therapeutic selectivity and to avoid systemic toxicity issues typically found with protease inhibitors. As a biological research tool, the invention described herein allows for the selective inhibition of proteases wherever light can reach. The light activation methods described herein thus provide new avenues for experimentation and studying biological systems that are not currently available with traditional enzyme inhibitors, for example, those that are not light activated, such as selective enzyme inhibition in single cell types or groups of cells in a complex environment.

Because of the nature of the caging strategy, a ruthenium complex is released from the inhibitor upon photolysis. Ruthenium complexes have been used successfully and repeatedly in chemical biology experiments without causing toxic or deleterious side effects. Potency will typically be controlled by the nature of the nitrile-based protease inhibitor, rather than the ruthenium center. Thus, by selecting a suitable protease inhibitor, enzyme inhibition can be achieved at low concentrations where side effects from ruthenium are negligible. An added benefit that the compounds is that they can act as dual-action therapeutics when activities from the ruthenium complex and the protease inhibitor are desired, such as anticancer applications where cell death is the goal. In such cases, ruthenium-caged inhibitors could be used at relatively high concentrations (e.g., >1 µM).

Ligands having a cyano (CN, nitrile) group are suitable because while they are not highly electrophilic they are robust (e.g., easy to synthesize) and difficult to metabolize (stable in the body). The crystal structures suggest that CN group is much smaller than methyl group and can react with thiolates in the sterically congested environment. Finally, the nitrile groups undergo photo induced ligand exchange more efficiently than any other monodentate ligand when bound to $Ru^{II}$.

Accordingly, the invention provides compounds that are nitrile-containing protease inhibitors ligated to $Ru^{II}$ complexes. The compounds can be activated by exposure to light. Novel methods for caging protease inhibitors are also described. For example, the complex $[Ru^{II}(bpy)_2(1)_2](PF_6)_2$ (V), where bpy is 2,2'-bipyridine, can be prepared from the nitrile-based peptidomimetic inhibitor 2-acetylamino-N-cyanomethyl-3-phenyl-propionamide (1). $^1$H NMR, UV-Vis and IR spectroscopic and mass spectrometric data confirm that two equivalents of inhibitor 1 bind to $Ru^{II}$ through the nitrile functional group. Complex V shows excellent stability in aqueous solution in the dark and fast release of 1 upon irradiation with visible light. Due to binding to the $Ru^{II}$ center, the nitriles of complex V are caged, and V does not act as a potent enzyme inhibitor. However, when V is irradiated, it releases compound 1 that inhibits the cysteine proteases papain and cathepsins B, K and L, up to two times more potently than 1 alone. Ratios for $IC_{50}$ values for V range from about 6:1 to about 33:1 under dark vs. light conditions, against isolated enzymes and in human cell lysates, confirming a high level of photoinduced enzyme inhibition is obtained with this method.

Protease Inhibitors

A variety of protease inhibitors can be used to form compounds of the invention for use in the methods of the invention. Several nitrile-based peptidic inhibitors of cysteine cathepsins are described by Frizler et al. (*Curr. Top. Med. Chem.* 2010, 10, 294-322). These nitrile-based inhibitors can be complexed with ruthenium to form prodrug compounds and compositions as described herein. Other nitrile-based inhibitors that can be used include those described by Greenspan et al., *J. Med. Chem.* 2001, 44, 4524-4534; Altmann et al., *Bioorg. Med. Chem. Lett.* 2006, 16, 2549-2554; Loeser et al., *J Med. Chem.* 2005, 48, 7688-7707; Fleming et al., *J. Med. Chem.* 2010, 53(22): 7902-7917; and Gauthier et al., *Bioorg. Med. Chem. Lett.* 2008, 18, 923-928.

U.S. Patent Application Nos. 2007/0191392 (Missbach) and 2007/0197510 (Ohmoto et al.) provide additional nitrile compounds that can be used to form the compounds described herein.

Examples of nitrile-based inhibitors that can be caged by a ruthenium complex include the inhibitors below. Any nitrile-containing inhibitor can be ligated to a ruthenium complex and used according to the methods described herein. Additional examples of nitrile-based inhibitors include those described by Boxer et al. in *Chem Med Chem* 2010, 5, 730-738.

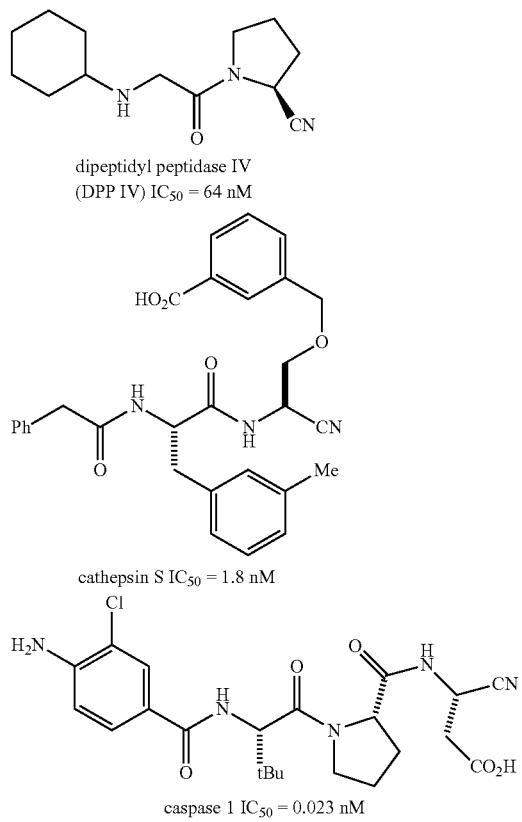

Other nitrile-containing compounds suitable for caging with ruthenium can be dipeptides, tripeptides, tetrapeptides, oligopeptides, or polypeptides, where compound can be optionally substituted and the nitrile is located on an amino acid, amino acid side chain, or on a substituent, or the nitrile is linked to the compound through a linker. Examples of linkers include a direct bond, an optionally functionalized $(C_1-C_{20})$alkyl group or $(C_3-C_{16})$cycloalkyl group, where the alkyl group or cycloalkyl group can optionally be a heteroalkyl group or a heterocycloalkyl group where one or more carbon atoms of an alkyl group or cycloalkyl group is replaced by nitrogen, oxygen, sulfur, or combinations thereof.

In some embodiments, the nitrile-containing inhibitor is a compound of Formula X:

where $R^x$ is an optionally protected amino acid, dipeptide, tripeptide, tetrapeptide, oligopeptide, or polypeptide. An amino acid of $R^x$ can be protected on nitrogen by an acetyl group or other nitrogen protecting group. An amino acid of $R^x$ can also be protected at a C-terminus by an oxygen or carboxylic acid protecting group. Suitable protecting groups are known to those skilled in the art (see for example, T. W. Greene, *Protecting Groups In Organic Synthesis*; Wiley: New York, Third Edition, 1999, and references cited therein; Philip J. Kocienski; *Protecting Groups* (Georg Thieme Verlag Stuttgart, New York, 1994),; D. Voet, *Biochemistry*, Wiley: New York, 1990; L. Stryer, *Biochemistry*, (3rd Ed.), W.H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein).

The nitrile-containing inhibitor can be an optionally protected amino acid, dipeptide, tripeptide, tetrapeptide, oligopeptide, or polypeptide that has a molecular weight of less than about 1200 Da, typically less than about 1000 Da, less than about 800 Da, less than about 750 Da, less than about 600 Da, or less than about 500 Da. The compound typically has a molecular weight of at least about 100 Da, at least about 200 Da, at least about 250 Da, at least about 300 Da, at least about 400 Da, or at least about 500 Da.

Examples of suitable amino acids that can be represented by $R^x$ include:

glycine;

aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

amino acid amides such as glutamine and asparagine;

polyamino- or polybasic-monocarboxylic acids such as arginine, lysine, β-aminoalanine, γ-aminobutyrine, ornithine, citrulline, homoarginine, homocitrulline, hydroxylysine, allohydroxylsine and diaminobutyric acid;

other basic amino acid residues such as histidine;

diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

imino acids such as proline, hydroxyproline, allohydroxyproline, γ-methylproline, pipecolic acid, 5-hydroxypipecolic acid, and azetidine-2-carboxylic acid;

a mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

aliphatic α-amino-β-hydroxy acids such as serine, β-hydroxyleucine, β-hydroxynorleucine, β-hydroxynorvaline, and α-amino-β-hydroxystearic acid;

α-amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-amino-β-thiols such as penicillamine, β-thiolnorvaline or β-thiolbutyrine;

other sulfur containing amino acid residues including cysteine; homocysteine, β-phenylmethionine, methionine, S-allyl-L-cysteine sulfoxide, 2-thiolhistidine, cystathionine, and thiol ethers of cysteine or homocysteine;

phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-hydroxy and substituted α-hydroxy amino acids including serine, threonine, allothreonine, phosphoserine and phosphothreonine.

$R^x$ can be substituted by a second amino acid to form a dipeptide, or $R^x$ can be substituted by two amino acids to form a tripeptide, etc. Examples of two amino acid units in the compounds include the dipeptidyl groups (designated by their single letter code) AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV. Combinations of $R^x$ and these groups can be used to form a variety of compounds of Formula X.

The nitrile group can be linked to $R^x$ through a direct bond, or a methylene group as in Formula X, or the nitrile group can be linked to $R^x$ through a linker L. The linker L can be connected to the nitrile group at one end and a nitrogen or carbonyl group of an amide-containing compound at the other end. The group L can be, for example, an optionally substituted, optionally interrupted, $C_1$-$C_{20}$ alkyl group, a $C_1$-$C_{16}$ cycloalkyl group, or a heteroatom such as O, N(H), or S. Two specific examples of -L-CN include —NH—$CH_2$—CN and —NH-(1,1-cyclopropyl)-CN.

Ruthenium Compounds

The invention provides compounds of Formula I:

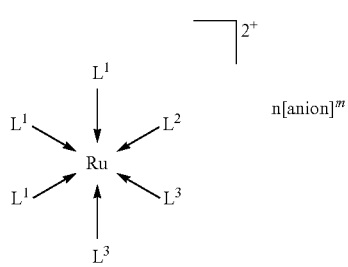
(I)

wherein each $L^1$ is independently a nitrogen-containing ruthenium ligand; each $L^2$ is a protease inhibitor having the formula R—CN or a solvent molecule coordinated to ruthenium; each $L^3$ is $L^1$ or $L^2$; and n[anion]$^m$ is a pharmaceutically acceptable anion where n is 2 and m is −1, or n is 1 and m is −2. In various embodiments, two $L^1$ groups can optionally form a bidentate ligand, three $L^1$ groups can optionally form a tridentate ligand, four $L^1$ groups optionally form a tetradentate ligand (e.g., where one $L^3$ group is an $L^1$ group), and/or or five $L^1$ groups optionally form a pentadentate ligand (e.g., where both $L^3$ groups are $L^1$ groups). Each $L^2$ can be a protease inhibitor having the formula R—CN, or one $L^2$ is a protease inhibitor and the other $L^2$, when present, can be a solvent molecule or anion coordinated to ruthenium, and when both $L^2$ are protease inhibitors, R—CN of each $L^2$ can be the same or different.

The also invention provides compounds of Formula IA:

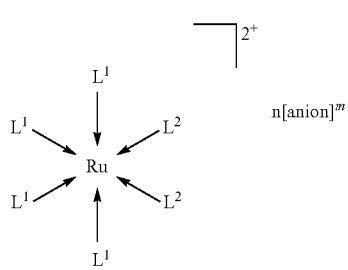
(IA)

wherein each $L^1$ is independently a nitrogen-containing ruthenium ligand, where two $L^1$ groups can optionally form a bidentate ligand and three $L^1$ groups can optionally form a tridentate ligand, each $L^2$ is independently a protease inhibitor having the formula R—CN, and wherein each $L^2$ is the same or different; and n[anion]$^m$ is a pharmaceutically acceptable anion where n is 2 and m is −1, or n is 1 and m is −2.

Figure 11A:
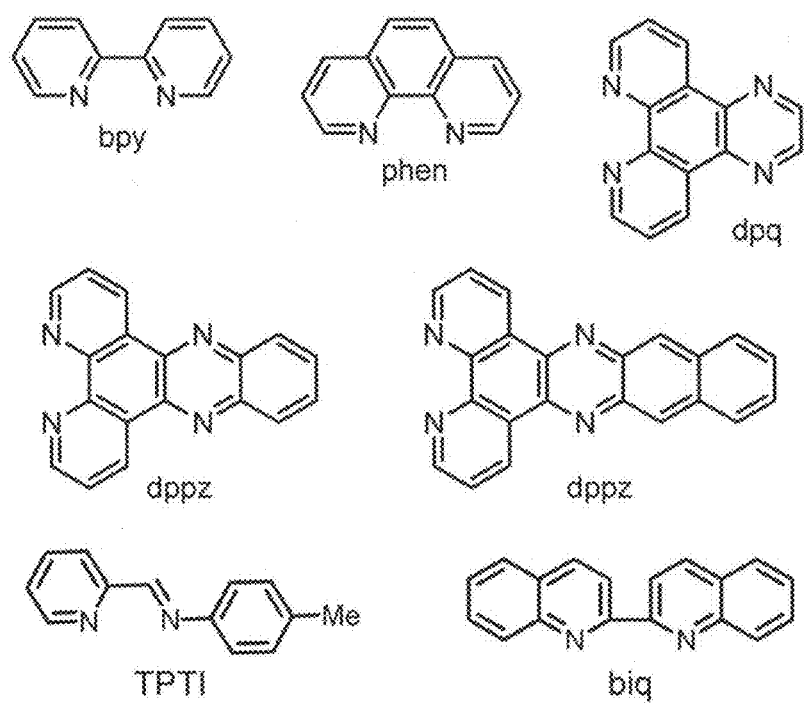
FIG. 11. The structures of several suitable ruthenium ligands. (A) bis-nitrogen bidentate ligands; (B) mono-nitrogen bidentate ligands; (C) tridentate, tetradentate, and pentadentate ligands; $R^1$ and $R^2$ can each independently be —CH$_2$-Ph-OH or —CH$_2$—NR$^a$R$^b$ where R$^a$ and R$^b$ can each independently be H, (C$_1$-C$_{10}$)alkyl, or (C$_6$-C$_{10}$)aryl, or another amine substituent group as defined herein.
Figure 11B:
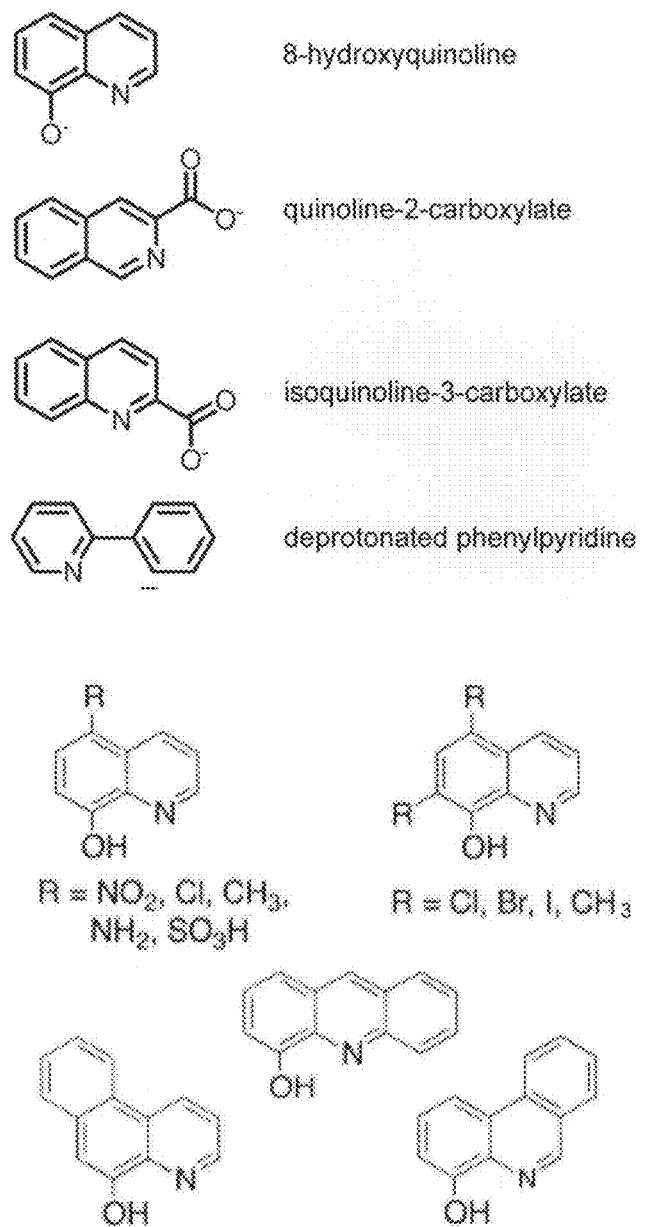
Figure 11C:
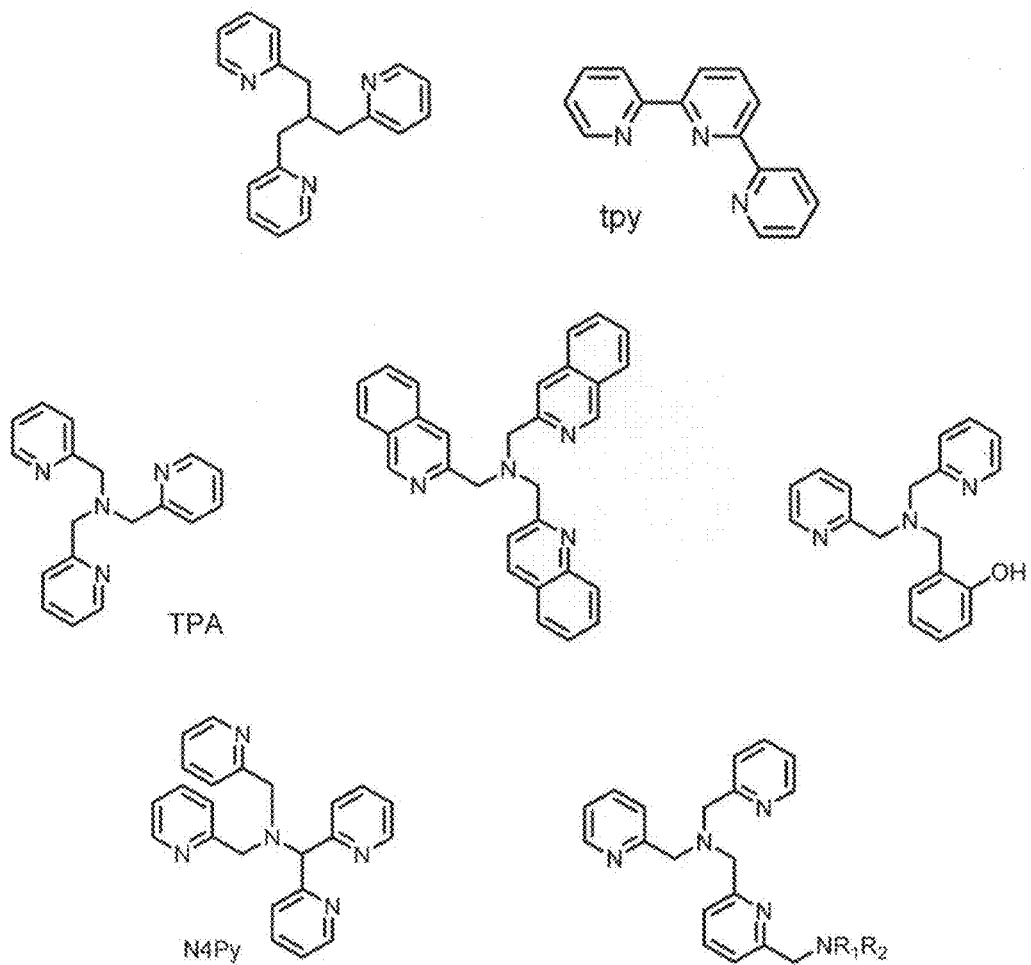

The ligands, $L^1$ can be monodentate ligands, such as pyridine or para-aminopyridine, or two or more $L^1$ groups can combine to form bidentate ligands, such as bipyridine (bpy) or 1,10-phenanthroline (phen), tridentate ligands, or tetradentate ligands. Examples of suitable bidentate ligands, tridentate ligands, and tetradentate ligands that can be formed by the combination of $L^1$ groups are illustrated in FIG. 11.

The compound of Formula I can be a compound of Formula II:

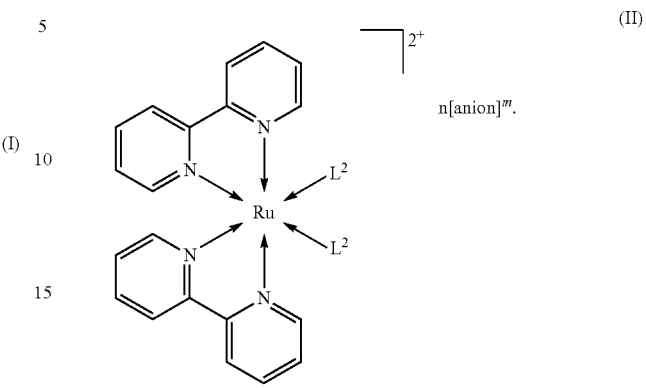
(II)

As discussed above, each $L^2$ can be a nitrile-containing protease inhibitor. Examples of specific $L^2$ groups include the nitrile compounds illustrated herein, as well as balicatib, L-006235, L-873724, MK-1256, nilvadipine, odanacatib, saxagliptin, or vildagliptin.

As would be recognized by one of skill in the art, a wide variety of ligands can be employed, including various aromatic N-donors, O-donors, and halides. The ligands can also be optionally substituted, for example, with a group recited below in the definition of the term substituent. In various embodiments, the pyridine or bipyridine ligands, or pyridine moieties of the ligands, can be substituted alkyl groups, halo groups, or other groups known to be used on ruthenium ligands, for example, as shown in FIG. 11B.

In some embodiments, the ligands on the ruthenium can include tridentate ligands such as terpyridine (tpy) or tris (pyrazolylmethane) (tpm). In such embodiments, the compound of Formula I can include one less R—CN group to provide a corresponding compound of Formula III. In some embodiments, a bidentate ligand of Formula III can be replaced by two R—CN groups. Alternatively, the compound can include one monodentate ligand and one tridentate ligand and two R—CN groups to provide a corresponding compound of Formula IV. In some embodiments, the monodentate ligand of Formula IV can be replaced by an R—CN group.

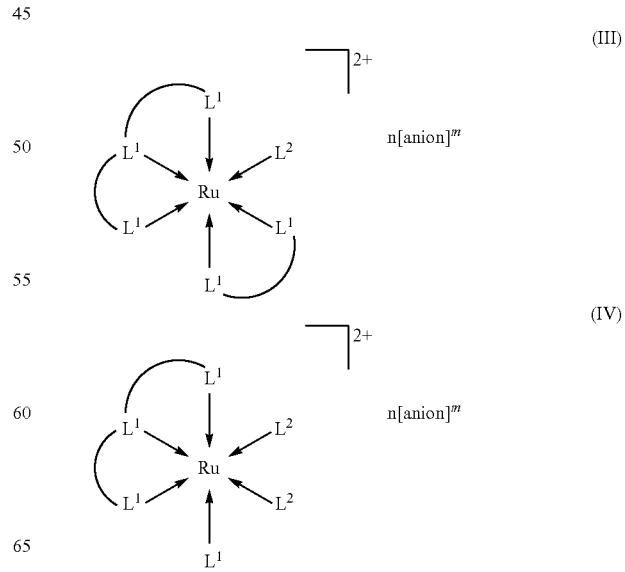
(III)

(IV)

Examples of bidentate ligands that can be used in the ruthenium compounds of the Formulas described include bipyridine (bpy), 1,10-phenanthroline (phen), dipyrido[3,2-f:2',3'-h]quinoxaline (dpq), dipyrido[3,2-a:2',3'-c]phenazine (dppz), and benzo[i]dipyrido[3,2-a:2',3'-h]quinoxaline (dppn), among others. Anionic ligands can also be used in the ruthenium compounds of the Formulas described herein. Examples include 8-hydroxyquinoline, quinoline-2-carboxylate, isoquinoline-3-carboxylate, and deprotonated phenylpyridine, among others. In various embodiments, the Formulas can be heteroleptic complexes with two different bidentate ligands. The structures of several useful bidentate ligands are shown in FIGS. 11A and 11B.

The useful bidentate, tridentate, tetradentate, and pentadentate ruthenium ligands, such as those described herein, can be either purchases from commercial vendors such as Sigma-Aldrich, Acros Organics, Alfa Aesar, or Strem Chemicals, Inc. Ligand preparation can be achieved by standard synthetic techniques well known in the art of organic synthesis. For example, the N4Py ligand can be prepared as shown in Scheme A using standard nucleophilic displacement conditions.

Scheme A. Preparation of N4Py Ligand.

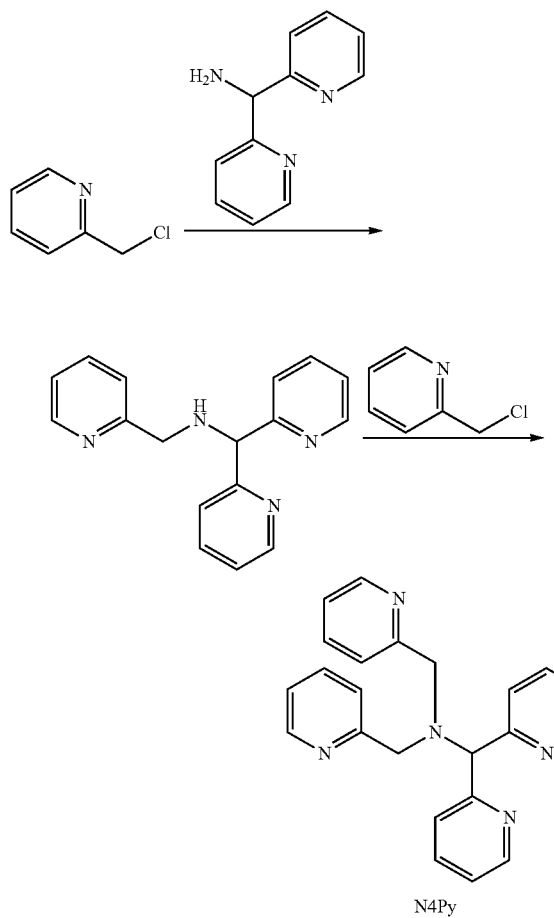

N4Py

Other useful ruthenium ligands and methods for their preparation are described in the literature, including the work of Kodanko and coworkers (*J. Org. Chem.* 2010, 75, 650-659; *Inorg. Chem.* 2010, 49, 5202-5211; and *J. Org. Chem.* 2011, 76, 2273-2276). These techniques can be used to prepare a wide variety of ligands as shown in Scheme B:

Scheme B.

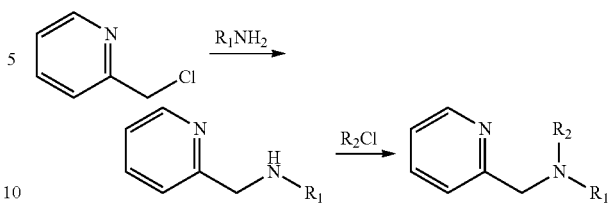

where $R^1$ and $R^2$ can be groups such as —$CH_2$-Ph-OH or —$CH_2$—$NR^aR^b$ where $R^a$ and $R^b$ can each independently be H, ($C_1$-$C_{10}$)alkyl, ($C_6$-$C_{10}$)aryl, —$CH_2$—$CO_2$H, —$(CH_2)$—$CO_2$H where n is 0 to about 10, ($C_1$-$C_{10}$)alkyl(aryl) or ($C_1$-$C_{10}$)alkyl(heteroaryl), for example, —$CH_2$-Py, —$(CH_2)_n$-Py where n is 0 to about 10, —$CH_2$—$CH_2$—NH(CO)-Py, —$(CH_2)_n$NH(CO)-Py where n is 0 to about 10. Other examples of suitable heteroaryl groups include pyrazine or pyrimidine; heterocycles can be attached to the carbon or carbon chain at any suitable carbon of the heterocycle. The aryl groups (e.g., phenyl or naphthyl) and the heteroaryl groups can be optionally substituted, as described herein. Additional suitable ruthenium ligands are illustrated in FIG. 28.

Thus, in some embodiments, the invention provides a complex of Formula XI:

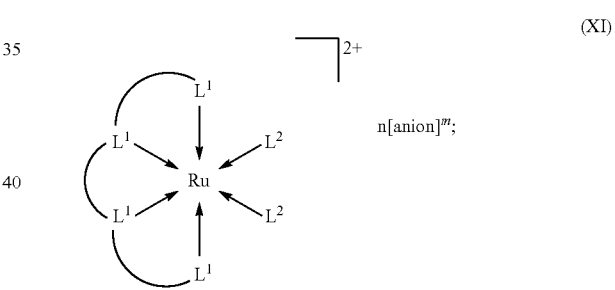

(XI)

wherein the variables are defined as described above for Formula I. In one embodiment, four $L^1$ groups of Formula XI combine to form a tetradentate ruthenium ligand, such as a TPA ligand, for example, the compound of Formula XI-A:

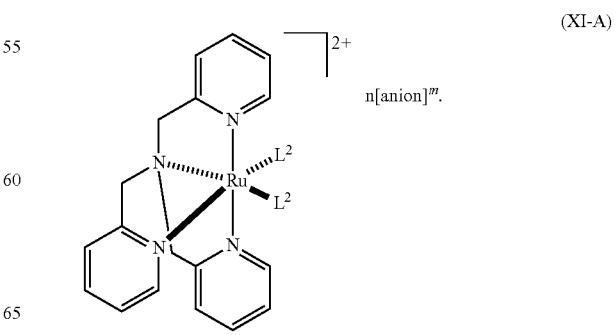

(XI-A)

In additional embodiments, the invention provides a complex of Formula XII:

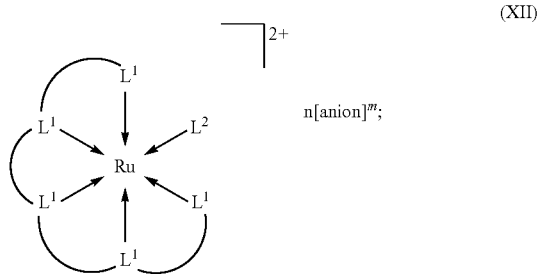

(XII)

wherein the variables are defined as described above for Formula I. In one embodiment, five $L^1$ groups of Formula XII combine to form a pentadentate ruthenium ligand, such as an N4Py ligand, for example, the compound of Formula XII-A:

$$[Ru(N4Py)(L^2)](n[anion]^m)$$  (XII-A).

Light Activation

The light activatable agents described herein can be selectively administered to specific treatment sites so that activation of the agents leads to treatment of cells at the treatment site but not surrounding tissue. This light activated drug therapy can therefore be used to treat cancers such as metastatic breast cancer, bone cancer, bladder cancer, lung carcinomas, esophageal cancer, basal cell carcinoma, malignant melanoma, ocular tumors, head and neck cancers, and other types of malignant tissue growths. The light activated agent can be preferentially absorbed by the abnormal tissue, and/or it can be infused into vasculature that supplies the abnormal tissue, so that the application of light releases the active inhibitory agent and leads to inhibition of the undesired cells. Because of the localized application of light, the light activated drug therapy can kill malignant tissue with less effect on surrounding benign tissue than standard treatment procedures.

Light can be administered to an internal treatment site by a variety of methods. One method includes administering the light through an optical fiber from an external source such as a laser. The light can be applied to a site exposed during a surgical procedure, or it can be administered using an implantable probe. Several implantable light emitting probes for administering light activated therapy to an internal site within a patient's body are described in U.S. Pat. No. 5,445,608 (Chen et al.). Flexible light emitting probes are described in U.S. Pat. No. 5,800,478 (Chen et al.), U.S. Pat. No. 5,766,234 (Chen et al.), and U.S. Pat. No. 5,876,427 (Chen et al.). The '608 patent describes an implantable probe containing a plurality of light sources that can be transcutaneously introduced to a desired treatment site through a surgical incision and then left in place for a period of time so that the light emitted by light emitting diodes (LEDs) or other types of light sources mounted in the probe can administer light to a light activatable compound described herein.

Flexible microcircuits can be introduced into the body through a natural opening or through a small incision, and can be positioned at the treatment site using conventional endoscopic techniques. Useful light emitting probes are described by, for example, U.S. Pat. No. 6,416,531 (Chen), and U.S. Patent Publication No. 2010/0145415 (Dahm et al.). Such implantable probes are merely exemplary rather than limiting in regard to the concepts disclosed herein.

The light applications can be provided once, or over a plurality of different times. The step of administering the light treatment can include administering a prodrug agent described herein (e.g., a compound of Formula I) to a treatment site. The agent can be selected for one or more characteristic wavebands of light absorption. Light having one or more emission wavebands substantially corresponding to at least one characteristic waveband of light absorption of the agent can be applied to the treatment site during each light therapy treatment. The light is then absorbed by the agent, which then releases the protease inhibitor. Light can be administered from a light source implanted within the abnormal tissue, or disposed adjacent to the abnormal tissue.

The methods may also include a step of imaging the treatment site to evaluate the effectiveness of the treatment in the abnormal tissue. Imaging may be accomplished using an ultrasound modality, a computer tomography modality, or a magnetic resonance imaging modality.

In various embodiments, an optical fiber can be used to administer light to a treatment site within a subject's body from an external light source such as a laser. Other types of light sources can be used, either in connection with implanted probes, or to provide light from outside the patient's body. The only significant requirement is that the light source produces light having a characteristic waveband corresponding to a light absorption waveband of the agent administered to the patient to implement the light activated therapy.

One light delivery system suitable for the delivery of light from a light source (such as a laser) to the targeted cells uses an optical fiber delivery system with special light-diffusing tips on the fibers. This type of light delivery system can further include optical fiber cylindrical diffusers, spherical diffusers, micro-lensing systems, an over-the-wire cylindrical diffusing multi-optical fiber catheter, and/or a light-diffusing optical fiber guide wire. This light delivery system can employ a remotely located high-powered laser, or solid-state laser diode array, coupled to optical fibers for delivery of the light to the targeted cells.

The light source for the light delivery system can also be light emitting diodes (LEDs) or solid-state laser diodes (LDs). LEDs or LDs can be arrayed in an elongated device to form a "light bar" for the light delivery system. The LEDs or LDs can be either wire bonded or electrically coupled utilizing a "flip chip" technique that is used in arranging other types of semiconductor chips on a conductive substrate. Various useful arrangements and configurations of LEDs or LDs are described in U.S. Pat. No. 5,445,608 (Chen et al.); U.S. Pat. No. 6,958,498 (Shelton et al.); U.S. Pat. No. 6,784,460 (Ng et al.); and U.S. Pat. No. 6,445,011 (Hirano et al.). Other small LEDs, LDs, and other light sources that are safe for use in the human body are described in U.S. Patent Publication No. 2009/0216300 (Leltner et al.).

Therapeutic Methods

The invention provides new methods for treating various conditions in mammals including cancers. Light of a specific wavelength or waveband can be directed toward a target cell or cells that have been contacted with a compound of Formula I. The compound can be administered to the patient by a variety of methods, including intravenous injection, oral administration, or by local delivery to the treatment site. A light source emitting certain wavelength or waveband can be used to irradiate the area to release the inhibitory agent, thereby allowing for the inhibition or death of cancer cells or tissue. The methods are therefore minimally invasive, less costly, and have lower risks of complications than standard surgical removal of cancerous tissue.

The methods described herein can be used to deliver and/or activate a protease inhibitor prodrug, such as a compound of Formula I. The location on a subject to be treated can be, for example, a tumor. The nitrile-containing inhibitor can be a selective protease inhibitor that can be released from the compound of Formula I by exposure to light, thereby converting a substantially non-toxic prodrug into a drug having substantial cytotoxicity and/or inhibitory activity.

The invention also provides methods of treating a localized entity comprising a group of cells in a human or animal body. The entity can be one that is distinguished from surrounding tissue by the presence of a specific determinant that is present in substantially higher concentration in the surrounding tissue, for example, overexpressed cysteine cathepsins. The methods can include:

a) administering to a human or animal body a compound of Formula I. The compound of Formula I includes two protease inhibitors that can be released in the presence of a sufficient amount of light. In other words, the two protease inhibitors are dissociable from the remainder of the ruthenium compound upon exposure to electromagnetic radiation of appropriate energy, to restore and/or enhance the activity of the protease inhibitors; and b) applying electromagnetic energy to the compound to effect dissociation of said inhibitors, the compound of Formula I being administered in amounts such that the protease inhibitors are generated in a therapeutically effective amount.

In some embodiments, the light has a wavelength of about 10 to about 380 nm. In other embodiments, the light has a wavelength of about 380 to about 500 nm, about 380 nm to about 1100 nm, about 400 nm to about 1100 nm, or about 500 nm to about 1100 nm. In various embodiments, the light has a wavelength of about 365 nm to about 425 nm, or about 395 nm. In other embodiments, the light has a wavelength of about 560 nm to about 700 nm, about 600 nm to about 660 nm, about 620 nm to about 640 nm, or about 632 nm, or about 635 nm, i.e., the output of a HeNe laser. In one embodiment, the light is produced from a flexible endoscopic light source or laser pointer.

An appropriate wavelength of light used for activating the prodrug ligands of various compounds can be obtained from any suitable and effective light source, e.g., a fluorescent lamp or an ordinary light bulb. The target cells or tissue is preferably illuminated with light at the time of or shortly after being contacted with the compound. One suitable light source is a laser or a light source having a lens that focuses the beam of light to a narrow area. In some embodiments, the light used for activating the compounds can be UV light (i.e., $\lambda=310$-380 nm) or blue light (i.e., $\lambda=380$-500 nm).

Cells in a particular area of the body can be reached by a light source using a variation of endoscopy. For example, a light source can be linked to a flexible instrument that can be inserted through an opening of the body such as the mouth, a cavity, or a surgical opening. In particular, the light source can be a lighted optical shaft or open tube. The optical shaft used can include bundles of fiber optic glass fibers that are bundled to together to form a flexible light source that can be easily bent and twisted around corners. Examples of endoscopic tools that can be adapted for use in the invention include the bronchoscope (for application of light to the bronchial tubes); gastroscope (for application to the stomach); proctosigmoidoscope (for application to the rectum or lower colon); and the cytoscope (for application of light to the bladder).

An incision may be required to insert the light source into the subject. Examples of endoscopic tools requiring an incision that can be adapted for use in the invention include the thoracoscope (for application of light to the chest cavity and surface of the lungs through a small incision between the ribs); peritoneoscope (for application of light to the abdominal cavity and lower surface of the liver and gallbladder through a small incision in the abdominal wall); and culdoscope (for application of light to the female pelvic organs through a small vaginal incision). Examples of organs that can be accessed by the flexible light source include the esophagus, stomach, lungs, bronchial tubes, duodenum, colon, liver, bladder, pancreas, gall bladder, and bones. One skilled in the art would recognize any organ or body tissue may be accessed by the appropriate technique.

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

Compositions and preparations of the compounds described herein typically contain at least 0.1% of active compound, often about 0.5% to about 60% by weight. The percentage of the compositions and preparations can vary and may conveniently be about 0.1% to about 60%, or about 2% to about 20% of the weight of a given unit dosage form. The amount of compound in such therapeutically useful compositions is such that an effective dosage level can be achieved.

Material used in preparing any unit dosage form should be pharmaceutically acceptable and substantially non-toxic in the amounts employed. In addition, the compound may be incorporated into sustained-release preparations and devices.

A compound described herein may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the compound in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form. However, it will generally be desirable to administer the compound to the skin as a composition or formulation, for example, in combination with a dermatologically acceptable excipient, diluent, or carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants including antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, and the like, for application directly to a surface or the skin of the subject.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing the in vitro activity, and in vivo activity of the corresponding inhibitors in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention thus provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, bone cancer, breast cancer, melanoma and leukemia, and in general is characterized by an undesirable cellular proliferation, e.g., unregulated growth, lack of differentiation, local tissue invasion, and metastasis.

The ability of a compound to treat cancer may be determined by using assays well known to the art. For example, the design of treatment protocols, toxicity evaluation, data analysis, quantification of tumor cell kill, and the biological significance of the use of transplantable tumor screens are known.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more can refer to one or two, one to three, one to four, one to five, or more than five.

The term "about" can refer to a variation off 5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

Specific values listed below for radicals, substituents, and ranges, are for illustration only; they do not exclude other defined values or other values within defined ranges for the radicals and substituents, for example, a substituent on an aryl moiety of a ruthenium ligand. However, certain values or ranges of values can optionally be excluded from certain embodiments in the form of negative limitations.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups when specifically noted. The alkyl can be a monovalent hydrocarbon radical, as described and exemplified above, or it can be a divalent hydrocarbon radical (i.e., an alkylene).

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, as described above in the definition of "substituted". Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto. The heteroaryl can be unsubstituted or optionally substituted, as described for alkyl groups.

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replace by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl (e.g., vinyl, or allyl), alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure; or combinations thereof. Additionally, suitable substituent groups can be, e.g., —X, —R, —O$^-$, —OR, —SR, —S$^-$, —NR$_2$, —NR$_3$, =NR, -CX$_3$, —CN, —OCN, —SCN, —N=C=O, —NCS, —NO, —NO$_2$, =N$_2$, —N$_3$, —NC(=O)R, —C(C=O)R, —C(C=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(C=O)R, —C(C=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, cycloalkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more substituents above can be excluded from the group of potential values for substituents on the substituted group. The various R groups in the schemes and figures of this disclosure can be one or more of the substituents recited above, thus the listing of certain variables for such R groups (including R$^1$, R$^2$, R$^a$, R$^b$, etc.) are representative and not exhaustive, and can be supplemented with one or more of the substituents above.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

A "solvent molecule coordinated to ruthenium" refers to any solvent that has a lone pair of electrons and that can form a complex with ruthenium, where the solvent molecule forms one of the ligands of the ruthenium. Examples of solvent molecules that can coordinate to ruthenium include acetonitrile (MeCN), water, and DMSO. A solvent molecule coordinated to ruthenium also refers to ions that can be present in solution that can coordinate to ruthenium, such as chloride, bromide, and the like.

Nitrile compounds can be release from the ruthenium complexes described herein at various wavelengths, including visible light having wavelengths of up to about 500 nm, and ultra violet (UV) light having wavelengths of about 350 nm to about 500 nm, or about 400 nm to about 500 nm. Other suitable and effective wavelengths of light for releasing nitrile compounds from ruthenium complexes are described in the Examples below. The nature of the specific ligand allows for wavelength tunable release of the nitrile ligands.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation and Characterization of Compounds 1 and V

General Experiments: All reagents were purchased from commercial suppliers and used as received. NMR spectra were recorded on a Varian FT-NMR Mercury-400 Spectrometer. Mass spectra were recorded on a Time-of-Flight Micromass LCT Premier XE Spectrometer or on a Waters ZQ2000 single quadrupole mass spectrometer using an electrospray ionization source. IR spectra were recorded on a Perkin Elmer Spectrum 2000 FT-IR Spectrometer. Enzymatic assays were conducted on a Tecan Infinite M200 or Tecan SPECTRAFluor Plus microplate reader. UV-Vis spectra (including time-dependent scans) were recorded on a Varian Cary 50 spectrophotometer. The photolysis experiments were conducted using a 250 W Tungsten Halogen lamp (Osram Xenophot HLX) powered by a 24 V power source. The irradiation wavelength was selected by placing a bandpass filter (395 nm cutoff) between the lamp and the sample, along with a 10 cm water cell to absorb infrared light. The confocal microscopy was performed with a Zeiss 510 Laser Scanning Microscope. All reactions were performed under ambient atmosphere unless otherwise noted. Anaerobic reactions were performed by purging the reaction solutions with Ar or N$_2$.

Experimental Procedures.

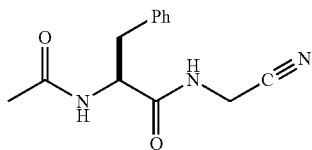

(S)-2-Acetamido-N-(cyanomethyl)-3-phenylpropanamide (1). Compound 1 was prepared by modification of published procedures (Loser et al., *J. Med. Chem.* 2005, 48, 7688-7707; Greenspan et al., *J. Med. Chem.* 2001, 44, 4524-4534). Boc-Phe-OH (20.0 mmol, 5.31 g) in dry DMF (110 mL) was treated with HBTU (24.0 mmol, 9.10 g), aminoacetonitrile hydrochloride (24.0 mmol, 2.22 g) and $Et_3N$ (48.0 mmol, 6.76 mL). The solution was maintained for 16 h. The crude reaction solution was combined with $CH_2Cl_2$ (150 mL) and the organic layer was washed with 0.1 M HCl (2×50 mL), sat. aqueous $NaHCO_3$ (2×50 mL) and brine (2×50 mL). The organic layer was dried ($Na_2SO_4$), filtered and concentrated. The crude product was analyzed by $^1H$ NMR spectroscopy (>90% purity) and was used without further purification.

The crude solid was dissolved in formic acid (100 mL) and maintained for 16 h. Excess formic acid was removed under reduced pressure and the resulting yellowish oil dissolved in $H_2O$ (100 mL), basified with sat. $NaHCO_3$ and extracted with EtOAc (3×100 mL). The organic layer was dried ($Na_2SO_4$), filtered and concentrated. The resulting solid was treated with $CH_2Cl_2$ (100 mL), $Et_3N$ (48.0 mmol, 6.75 mL) and acetic anhydride (24.0 mmol, 2.27 mL) and the solution was maintained for 12 h. The resulting slurry was partitioned between EtOAc (100 mL) and 0.1 M HCl (100 mL). The aqueous layer was extracted with EtOAc (3×100 mL). The organic layers were combined, dried ($Na_2SO_4$), filtered and concentrated. The crude product was recrystallized from hot EtOAc to give a white powder (2.42 g, 9.81 mmol, 49% over the 3 steps): $^1H$ NMR (400 MHz, DMSO-$d_6$) δ: 8.71 (t, J=5.7 Hz, NH), 8.22 (d, J=8.1 Hz, NH), 7.21 (m, 5H), 4.44 (dd, J=13.0, 4.9 Hz, 1H), 4.10 (d, J=5.7 Hz 2H), 2.97 (dd, J=13.8, 4.9 Hz, 1H), 2.73 (dd, J=13.9, 9.7 Hz, 1H), 1.75 (s, 3H); $[α]_D^{20}$ +6.4 (c=0.5, MeOH) $^{13}C$ NMR (100 MHz, DMSO-$d_6$) δ: 172.75, 169.93, 138.39, 129.74, 128.80, 127.04, 118.14, 54.50, 38.01, 27.74, 23.11; IR $ν_{max}$ (cm$^{-1}$): 3302, 3066, 3033, 2978, 2937, 2346, 2251, 1956, 1661, 1639, 1606, 1542, 1496, 1455, 1431, 1416, 1372, 1343, 1320, 1298, 1281, 1239, 1193, 1106, 1071, 1037, 966, 914, 893, 791, 747, 731, 702, 618, 600, 565, 519, 472; HRMS (ESMS) calculated for $C_{13}H_{15}N_3O_2Na$ [M+Na]$^+$: 268.1062, found: 268.1072.

Δ-cis-[Ru(bpy)$_2$(1)$_2$](PF$_6$)$_2$·2H$_2$O and Λ-cis-[Ru(bpy)$_2$(1)$_2$](PF$_6$)$_2$·2H$_2$O (V): A sealable tube was charged with cis-Ru(bpy)$_2$Cl$_2$ (0.20 mmol 97 mg), AgBF$_4$ (0.80 mmol, 156 mg) and (S)-2-acetamido-N-(cyanomethyl)-3-phenylpropanamide (1) (1.00 mmol, 245 mg) and freshly distilled EtOH (40 mL). The resulting solution was sealed under inert atmosphere in a glove box, wrapped in aluminum foil and heated to 80° C. for 12 h, during which it turned from dark violet to bright orange. After cooling the crude solution to rt (~23° C.), the reaction mixture was placed in the freezer at −20° C. for 16 h. The reaction mixture was filtered through Celite to remove precipitated silver salts and the filter cake was washed with cold EtOH. The solvents were removed under reduced pressure, resulting in formation of a yellow solid. The resulting yellow solid was dissolved in acetone (3 mL), layered with Et$_2$O (15 mL) and placed in the freezer at −20° C. for 16 h. The yellow solid was isolated by filtration and washed with cold Et$_2$O. The resulting solid was dissolved in $H_2O$ (25 mL) and the aqueous layer was extracted with EtOAc (3×20 mL) and MTBE (1×20 mL). The aqueous layer was treated with a saturated aqueous solution of NH$_4$PF$_6$ (5 mL), resulting in the formation of an orange precipitate that was isolated by centrifugation. The precipitate was washed with cold $CH_2Cl_2$, then dissolved in a mixture of $CH_2Cl_2$ and acetone (10:1). After storing this solution for 2 days at −20° C. the complex V precipitated and was obtained as a microcrystalline bright yellow-orange solid (45 mg, 37 μmol, 19% yield): mp=110° C. (decomp); $^1H$ NMR (400 MHz, acetone-$d_6$) δ: 9.55 (d, J=5.7 Hz, 1H), 9.51 (d, J=4.9 Hz, 1H), 8.81 (d, J=8.1 Hz, 2H), 8.68 (d, J=8.1 Hz, 2H), 8.43 (t, J=8.1 Hz, 2H, NH), 8.20 (t, J=5.7 Hz, NH), 8.11 (dt, J=7.7, 1.6 Hz, 2H), 8.03 (t, J=6.5 Hz, 2H), 7.87 (d, J=5.7 Hz, 2H), 7.80 (d, J=7.3 Hz, NH), 7.60 (d, J=7.3 Hz, NH), 7.45 (d, J=6.1 Hz, 2H), 7.23 (m, 10H), 4.56 (m, 5H), 4.32 (m, 1H), 3.12 (dd, J=9.72, 4.9 Hz, 1H), 3.09 (dd, 0.1=9.3, 5.3 Hz, 1H), 2.93 (dd, J=13.8, 7.3, Hz, 1H), 2.91 (dd, J=13.8, 6.5, Hz, 1H), 1.89 (s, 3H), 1.85 (s, 3H); IR (KBr) $ν_{max}$ (cm$^{-1}$): 3635, 3415, 3297, 3062, 3031, 2930, 2346, 2289, 1665, 1605, 1524, 1467, 1448, 1427, 1375, 1342, 1314, 1275, 1243, 1193, 1161, 1125, 1071, 1031, 961, 839, 766, 741, 731, 702, 663, 648, 558, 488; HRMS (ESMS) calculated for $C_{46}H_{46}N_{10}O_4Ru$ [M]$^{2+}$: 452.1380, found: 452.1366; Anal. Calcd for $C_{46}H_{50}F_{12}N_{10}O_6P_2Ru$ ([Ru(bpy)$_2$ (1)$_2$](PF$_6$)$_2$·2H$_2$O): C, 44.92; H, 4.10; N, 11.39. found: C, 44.79; H, 3.91; N, 11.33.

Part B. Synthesis of 2 and VI
Experimental Procedure:

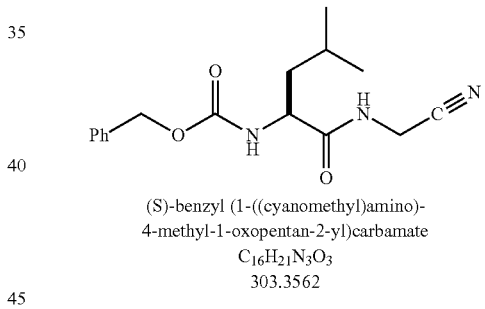

(S)-benzyl (1-((cyanomethyl)amino)-
4-methyl-1-oxopentan-2-yl)carbamate
$C_{16}H_{21}N_3O_3$
303.3562

(S)-benzyl (1-((cyanomethyl)amino)-4-methyl-1-oxopentan-2-yl)carbamate (2). (2) was prepared by a modification of published procedures ((Loser et al., *J. Med. Chem.* 2005, 48, 7688-7707; Greenspan et al., *J. Med. Chem.* 2001, 44, 4524-4534)). L-leucine (15.0 mmol, 1.97 g) was dissolved in 18.5 mL of 2.0 M NaOH cooled to 0° C. Benzyl chloroformate (17.3 mmol, 2.46 mL) was added in small portions over 30 min and the resulting solution stirred at RT for 12 h. The crude reaction solution was then acidified with 6.0 N HCl and extracted with EtOAc (3×30 mL). The organic layers were combined, dried ($Na_2SO_4$), filtered and concentrated to give 3.82 g of a sticky white solid. The crude product was analyzed by $^1H$ NMR spectroscopy (>90% purity) and was used without further purification.

Cbz-Leu-OH (7.00 mmol, 1.86 g) was dissolved in dry DMF (10.0 mL). Aminoacetonitrile HCl (8.40 mmol, 777 mg) was mixed with HBTU (8.4 mmol, 3.19 g) and $Et_3N$ (16.8 mmol, 2.36 mL) and dissolved in dry DMF (30.0 mL). Both solutions were combined and the resulting solution stirred under Argon was maintained for 16 h. The crude reaction solution was combined with $CH_2Cl_2$ (75 mL) and the organic layer was washed with 0.1 M HCl (2×30 mL), 1.0 M HCl (1×30 mL), sat. aqueous NaHCO$_3$ (2×30 mL) and brine (2×30 mL). The organic layer was dried (Na$_2$SO$_4$), filtered and concentrated. The crude product was recrystallized from hot EtOAc/Hexanes to give a white powder (950 mg, 45% from the first crop over the 2 steps). Mother liquors can be further recrystallized or purified by flash chromatography on silica.

$^1$H NMR (400 MHz CD$_2$Cl$_2$-d$_6$ δ) 7.33 (m, 5H), 7.06 (br, s, NH, 1H), 5.39 (br, s, NH, 1H), 5.0 (q, 2H), 4.21 (br, s, 1H), 4.05 (d, J=3.9 Hz, 2H), 1.63 (m, 2H), 1.52 (m, 1H), 0.91 (d, J=6.4 Hz, 3H), 0.89 (d, J=5.9 Hz, 3H). $^{13}$C NMR (100 MHz CD$_2$Cl$_2$-d$_6$ δ) 172.68, 156.48, 136.22, 128.52, 128.21, 127.89, 116.07, 67.20, 40.66, 27.48, 24.62, 22.63, 21.48. [α]$_D^{20}$ −33.9 (ϵ=1.0, CH$_2$Cl$_2$). mp 125.5-127°. IR ν$_{max}$ (thin film, cm$^{-1}$): 3306, 3065, 3036, 2958, 2872, 2258, 1693, 1673, 1531, 1537, 1469, 1455, 1411, 1388, 1369, 1342, 1261, 1238, 1172, 1121, 1043, 1028, 964, 909, 778, 739, 697. LRMS (ESMS) calculated for C$_{16}$H$_{22}$N$_3$O$_3$ [M+H]$^+$: 304.2, found: 304.5.

Synthesis of Δ- and Λ-cis [Ru(bpy)$_2$(2)$_2$]Cl$_2$ (VI): In the glove box, a sealable tube was charged with cis-Ru(bpy)$_2$Cl$_2$ (0.1 mmol 48.4 mg), AgBF$_4$ (0.4 mmol 77.9 mg) and (S)-benzyl (1-((cyanomethyl)amino)-4-methyl-1-oxopentan-2-yl)carbamate (2) (0.6 mmol 91.0 mg) and 20.0 mL of freshly distilled EtOH. The resulting solution was wrapped in aluminum foil and heated to 80° C. for 5 h during which it turned from dark violet to bright orange. After cooling the crude solution to RT, it was placed in the freezer at −20° C. for 16 h. The precipitated silver salts were filtered off using celite and the filter cake was washed with cold EtOH. The solvents were removed under reduced pressure and the crude mixture was analyzed by $^1$H NMR spectroscopy. The resulting yellow solid was dissolved in acetone (2 mL) and layered with Et$_2$O (10 mL) and placed in the freezer at −20° C. for 16 h. The reaction mixture was filtered and the filter cake washed with cold Et$_2$O. The resulting solid was dissolved in EtOAc (15 mL) and extracted 3 times with H$_2$O (15 mL). The organic layer was then precipitated (oily residue) with sat. n-Bu$_4$NCl in EtOAc (0.1 mL) at −20° C. The oily residue was isolated by centrifugation, the mixture was decanted and the residue was washed with cold EtOAc (3×5 mL), and then cold toluene (3×5 mL). The residue was dissolved in a minimum amount of acetone and layered with Et$_2$O. The resulting solid was washed with Et$_2$O to give the title compound as an orange solid in analytically pure form as a hydrate salt (21.0 mg, 0.019 mmol, 19%). $^1$H NMR (400 MHz CD$_2$Cl$_2$-d$_2$ δ) 9.93 (s, br, 2H), 9.54 (d, J=4.9 Hz, 1H), 9.51 (d, J=4.9 Hz, 1H), 8.53 (d, J=8.1 Hz, 1H), 8.45 (d, J=8.1 Hz, 2H), 8.36 (d, J=8.1 Hz, 1H), 8.15 (m, 2H), 8.02 (m, 2H), 7.93 (m, 2H), 7.54 (d, J=5.9 Hz, 2H), 7.32 (m, 8H), 7.25 (m, 2H), 6.86 (d, J=9.7 Hz, 1H, NH), 6.74 (d, J=8.1 Hz, 1H, NH), 5.04 (m, 3H), 4.16 (d, J=12.2 Hz, 1H), 4.28 (m, 6H), 1.08 (under the H$_2$O peak, m, 4H), 0.91 (m, 12H); IR (KBr) ν$_{max}$ (cm$^{-1}$): 3419, 3029, 2957, 2870, 2347, 2274, 1714, 1676, 1604, 1523, 1466, 1446, 1424, 1386, 1337, 1246, 1170, 1122, 1047, 917, 771, 731, 698, 670; LRMS (ESMS) calculated for C$_{52}$H$_{58}$N$_{10}$O$_6$Ru [M]$^{2+}$: 510.2, found: 510.1; Anal. Calcd for C$_{52}$H$_{65}$Cl$_2$N$_{10}$O$_{9.5}$Ru ([Ru(bpy)$_2$(2)$_2$]Cl$_2$0.3.5H$_2$O): C, 54.12; H, 5.68; N, 12.14. found: C, 54.16; H, 5.46; N, 12.13.

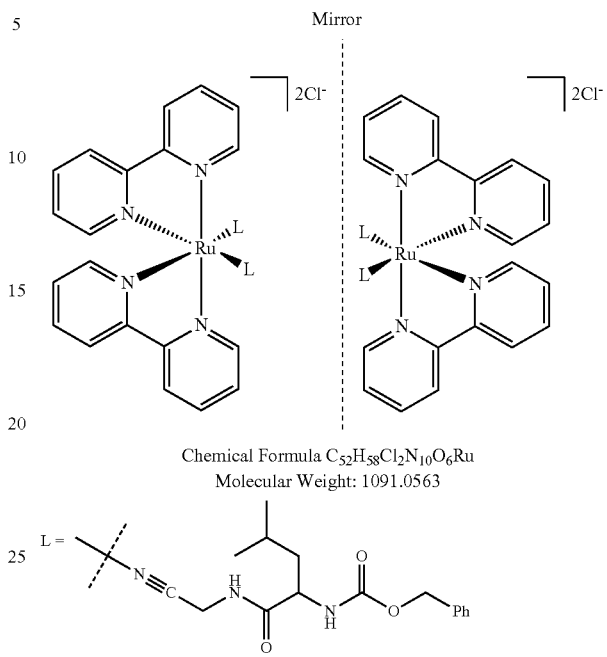

Scheme 1A. Δ-cis [Ru(bpy)$_2$(L$^2$)$_2$]Cl$_2$ (VI) and Λ-cis [Ru(bpy)$_2$(L$^2$)$_2$]Cl (VI').

Chemical Formula C$_{52}$H$_{58}$Cl$_2$N$_{10}$O$_6$Ru
Molecular Weight: 1091.0563

Stability of 3 in CatK assay buffer. A 50 μM solution of VI in a 400 mM sodium acetate, pH 5.5, 4 mM EDTA, 8 mM DTT buffer solution (0.5% DMSO) was placed in a cell, and UV-Vis spectra recorded for 6 hrs (the cell was shaken to help diffusion). Ln A was plotted vs. time and fitted to give a first order reaction rate r=0.00012802 min$^{-1}$. The half-life corresponding to this rate was approximately 5413 min~3.75 days (t$_{1/2}$=0.693/r).

Stability of in 0.1M pH 6.5.

Stability of VI in 0.1 M pH 6.5 phosphate buffer and Photochemical Quantum Yields. A 50 μM solution of VI in 0.1M pH 6.5 phosphate buffer (1.0% DMSO) was monitored by UV-Vis spectroscopy for 12 h. Ln A was plotted vs. time and the line was fit to give a first order reaction rate constant k$_{obs}$=1.0×10$^{-6}$s$^{-1}$, corresponding to a half-life >8.0 days (t$_{1/2}$=−0.693/k$_{obs}$). Photosubstitution quantum yields were determined using ferrioxalate actinometry as previously described in detail.[27] A 150 W Xe lamp housed in a Milliarc compact arc lamp housing (PTI) and powered by a PTI model LPS-220 power supply was used in the steady-state photolysis experiments; the wavelength of the light reaching the sample was controlled with colored glass long-pass and band-pass filters (Newport).

Cell Assays and Imaging. The live cell cathepsin K activity staining assays were performed following a method described previously (Tepel et al., J. Cell Sci. 2000, 113, 4487-4498). Briefly, osteoclasts were derived from FVBN mice as previously described. Cells were incubated for 30 min at 37° C. with 250 μL of reaction buffer (0.2 M sodium acetate, pH 6.0, 0.1 mM EDTA and 0.125 mM BME) containing 2 or 3 (1-1000 nM, +/−1 μM CA074, a cathepsin B inhibitor) in 1% DMSO. After 30 minutes, the cells were carefully washed with and left in PBS (phosphate buffered saline), the "dark" plate was wrapped in aluminum foil, whereas the "light" plate was exposed to visible light. The photolysis was conducted for 15 minutes (with gentle shaking of the plate every 2-3 min) using a 250 W tungsten halogen lamp (Osram Xenophot HLX) powered by a 24V power supply, using bandpass and water filters, as described previously. The cells were washed with PBS, and treated with 250 μL of substrate solution in reaction buffer consisting of 1.0 mM Z-Gly-Pro-Arg-4MβNA (cathepsin K substrate), and 1.0 mM nitrosalicylaldehyde (precipitating agent). The reaction was allowed to occur for 30 minutes at 37° C.

Controls were incubated in the same manner but without substrate (with or without 1.0 μM CA074). After 30 minutes, the cells were washed and fixed with 1% formaldehyde for 20 min minutes at RT. After being washed with PBS and distilled water, the coverslips were mounted on microscope slides and viewed with a confocal laser scanning microscope (Zeiss LSM 510). DAPI was used as the nuclear dye. For quantitative studies, cells were fixed and images captured with Zeiss 510 laser confocal microscope using a 40× oil immersion lens. Images of control and complex VI-treated osteoclasts (4 images/treatment) were analyzed using Meta-Morph software. Integrated intensities of green fluorescence were normalized to the number of nuclei (DAPI).

Example 2

Light Activation of a Cysteine Protease Inhibitor: Caging of a Peptidomimetic Nitrile with $Ru^{II}(bpy)_2$ This example describes general methods for caging cysteine protease inhibitors, wherein a peptidomimetic nitrile-based inhibitor is rendered inert through binding to a ruthenium center. Upon photolysis, the nitrile-based inhibitor is unleashed, providing high levels of selectivity for enzyme inhibition under light vs. dark conditions. This strategy was proven effective against purified enzymes and in lysates.

Many cysteine protease inhibitors contain electrophilic groups that react with nucleophilic thiolates of active site cysteines and anchor the inhibitor to the target enzyme, including epoxides, ketones, alkyl halides and nitriles. A series of potent and selective peptidomimetic inhibitors have been developed against cysteine cathepsins that contain C-terminal nitriles, including analogs targeting cathepsin K that have moved into Phase II clinical trials. Interaction between a nitrile and the active site cysteine of cathepsin B was confirmed through X-ray crystallographic analysis to generate a thioimidate, which forms in a reversible fashion upon inhibitor binding. The inventors recognized that if the nitrile functional group of a protease inhibitor could be bound in a stable fashion to a metal center, it would likely be inert toward attack by active site cysteines. Thus, metal binding would cage the inhibitor, which could be released upon photolysis to interact with the target enzyme (Scheme 1).

To investigate the caging of nitrile-based inhibitors, the moiety $Ru^{II}(bpy)_2$ was chosen, which displays excellent caging and photoreactive properties. The therapeutic use of caged nitrile-based inhibitors would provide multiple biologically active agents upon photoactivation from a single precursor, including two equiv of nitrile-based inhibitor and 1 equivalent of $[Ru^{II}(bpy)_2(H_2O)_2]^{2+}$. Possessing a dual mode of action would make this class of compounds useful for targeting cancer cells because cis-$[Ru(L)_2(H_2O)_2]^{2+}$ (L=bpy, phen) and cis-$Ru(phen)_2Cl_2$ covalently bind to DNA (phen=1,10-phenanthroline).

Preparation of Inhibitor Complexes. Synthesis of the $Ru^{II}$ inhibitor complex started from nitrile-based inhibitor 1 (Scheme 2). Reaction of $Ru^{II}(bpy)_2Cl_2$ with 5 equiv of 1 and excess $AgBF_4$ in EtOH for 12 hours resulted in a color change from dark violet to orange, consistent with displacement of the chloride groups on $Ru^{II}(bpy)_2$ by nitrile 1. After filtration, concentration and precipitation from acetone and ether, the residue was dissolved in $H_2O$ and the aqueous layer was washed with EtOAc to remove excess 1. Subsequent anion exchange, by treatment of the aqueous solution with excess $NH_4PF_6$, resulted in formation of an orange precipitate. The compound $[Ru^{II}(bpy)_2(1)_2](PF_6)_2$ (2) was obtained as a microcrystalline yellow solid in analytically pure form from this material by slow crystallization from a cold acetone and dichloromethane mixture.

Scheme 2. Synthesis of the ruthenium-based, caged protease inhibitor $[Ru^{II}(bpy)_2(1)_2](PF_6)_2$ (V).

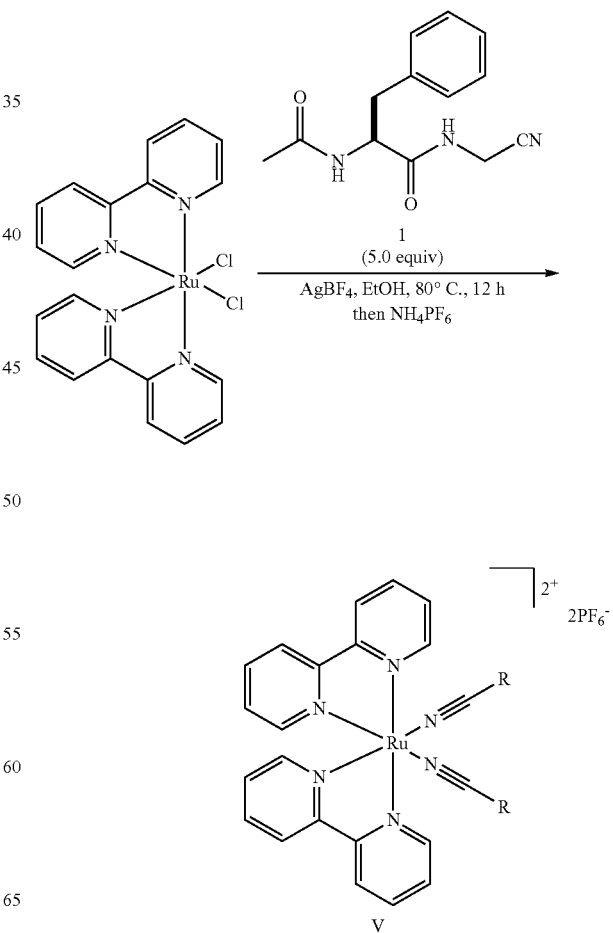

Scheme 1. Caging strategy for nitrile-based cysteine protease inhibitors.

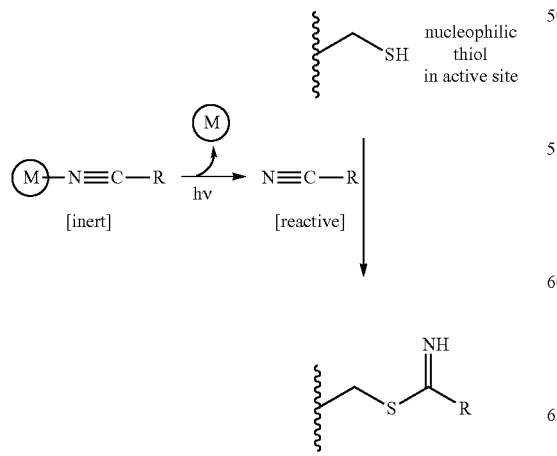

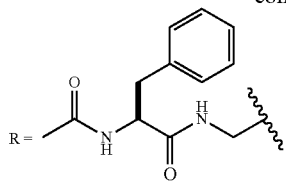

Complex V was characterized by $^1$H NMR, UV-Vis and IR spectroscopies, mass spectrometry, and elemental analysis. $^1$H NMR spectroscopic analysis confirmed that V was obtained as a 1:1 mixture of diastereoisomers. This was expected because 1 is chiral and enantioenriched, prepared from L-phenylalanine (S configuration), and $Ru^{II}(bpy)_2Cl_2$ is a racemic mixture of $\Lambda$ and $\Delta$ stereoisomers. Thus a mixture of ($\Lambda$, S, S) and ($\Delta$, S, S) is isolated (see Scheme 3). Obtaining a mixture of stereoisomers does not affect enzyme inhibition because 1 is released from V during photolysis and $[Ru^{II}(bpy)_2(H_2O)_2]^{2+}$ does not act as a potent protease inhibitor.

Scheme 3: $\Delta$-cis $[Ru(bpy)_2(1)_2](PF_6)_2$ and $\Lambda$-cis $[Ru(bpy)_2(1)_2]$ $(PF_6)_2$.

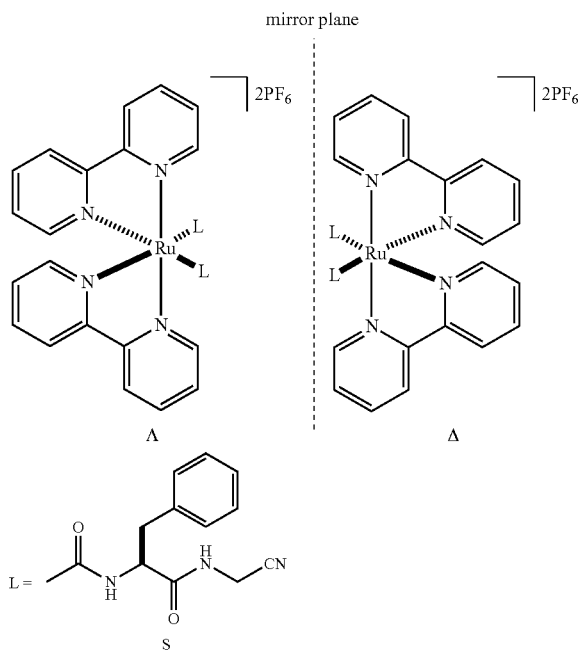

Figure 1:
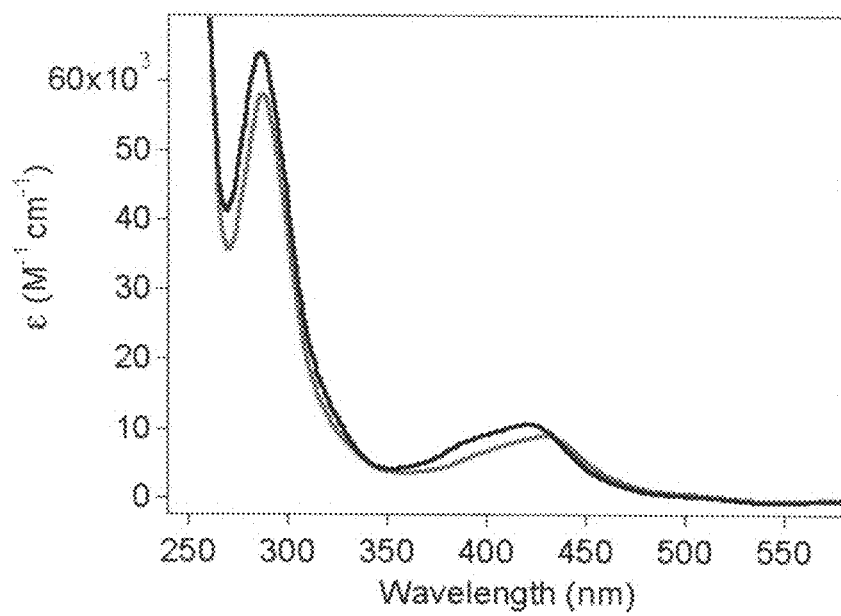
FIG. 1. UV-Vis spectrum of 2 (top) and [$Ru^{II}$(bpy)$_2$(MeCN)$_2$](PF$_6$)$_2$ (lower) in DMSO.

The $^1$H NMR spectrum of V in acetone-$d_6$- shows two acetyl peaks, one for each diastereomer of V. In turn, each diastereomer possesses two nitrile-based inhibitors that appear as one resonance because they are magnetically equivalent due to $C_2$ symmetry. Further analysis by $^1$H NMR spectroscopy verified that the methylene protons adjacent to the nitrile are shifted by about 0.6 ppm in $Ru^{II}$ complex V relative to 1, consistent with binding of the nitrile to the $Ru^{II}$ center. The IR spectrum of V shows a resonance at 2280 cm$^{-1}$, shifted by 30 cm$^{-1}$ relative to 1 ($\nu_{CN}$=2250 cm$^{-1}$), again consistent with nitrile binding to the $Ru^{II}$ center. The UV-Vis spectrum of V in DMSO (FIG. 1) agrees well with data for the related complex $[Ru^{II}(bpy)_2(MeCN)_2](PF_6)_2$, showing $\lambda_{max}$ at 281 nm ($\epsilon$=60,000 M$^{-1}$ cm$^{-1}$) and 422 nm ($\epsilon$=10,700 M$^{-1}$ cm$^{-1}$) (Liu et al., J. Am. Chem. Soc. 2009, 131, 26-27). The mass spectrum of V (ESI) shows a prominent peak at m/z=452.1366, along with a suitable isotope pattern, consistent with a predication of the formula $[Ru^{II}(bpy)_2(1)_2]^{2+}$.

Figure 2:
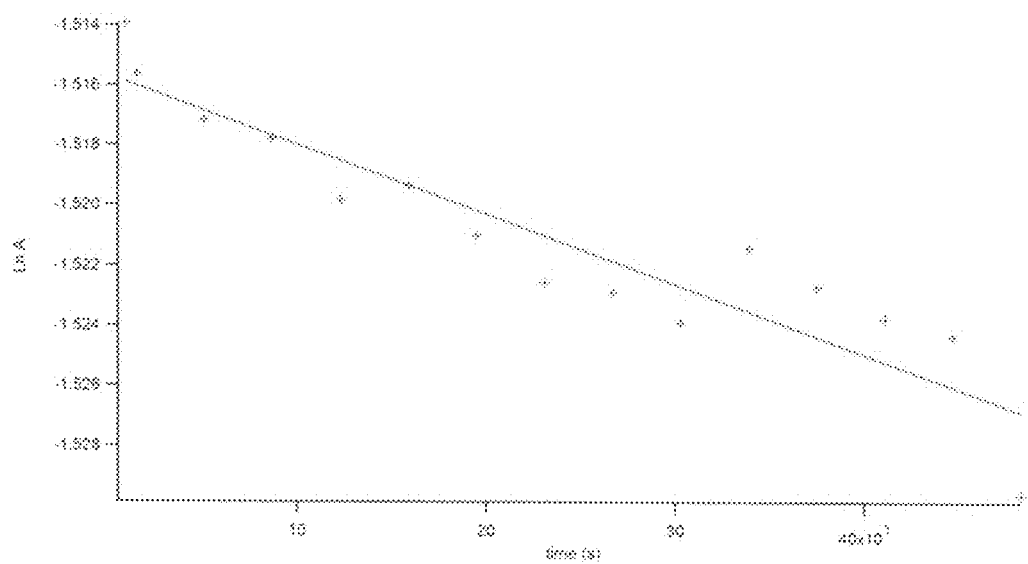
FIG. 2. Plot of ln A vs. t for 2 in 0.1M phosphate pH 6.5 buffer at rt.
Figure 3:
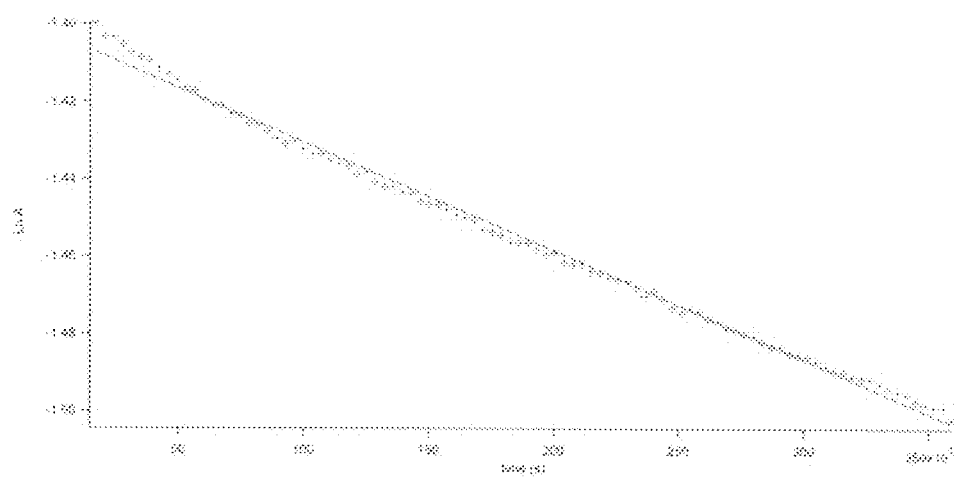
FIG. 3. Plot of ln A vs. t for 2 in DMSO at rt.
Figure 4:
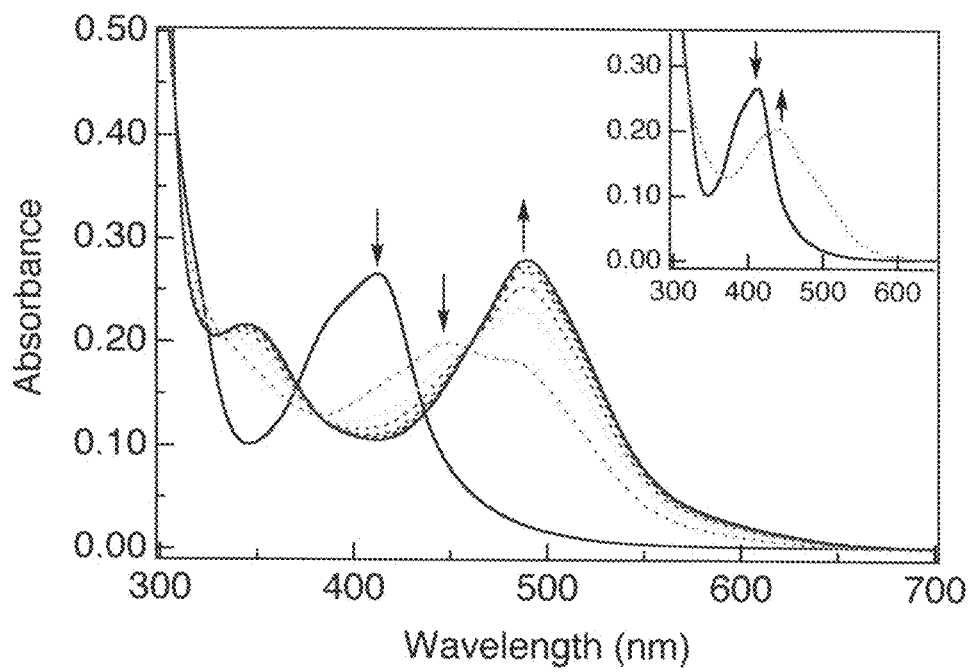
FIG. 4. Changes to the electronic absorption spectrum of 30 μM cis-[Ru(bpy)$_2$(1)$_2$](PF$_6$)$_2$ (2) in a 1% DMSO aqueous solution upon irradiation ($\lambda_{irr}$>395 nm) at $t_{irr}$=0, 2, 3, 4, 5, 6, and 7 min; inset: 0, 1 min.

Complex V shows excellent stability in solution in the dark and fast release of 1 upon irradiation with visible light. Rates of decomposition for V were determined spectrophotometrically in the dark in aqueous phosphate buffer and DMSO solutions. Plots of ln A vs. t were linear and provided rate constants of 2.3×10$^{-7}$ s$^{-1}$ and 2.8×10$^{-7}$ s$^{-1}$ in buffer and DMSO, respectively (FIGS. 2 and 3). These values prove that V has a $t_{1/2}$>28 days in solution. The changes in the electronic absorption spectrum of a 1% DMSO aqueous solution of V (30 μM) upon irradiation with visible light ($\lambda_{irr}$>395 nm) were used to monitor the progress of the photochemical reaction, as shown in FIG. 4. A decrease in the Metal to Ligand Charge Transfer (MLCT) absorption of the reactant at 414 nm is observed with a concomitant appearance of a new peak at 444 nm within 1 minute of irradiation (FIG. 4 inset). This peak is attributed to the Ru→bpy MLCT absorption of the mono-aqua complex, cis-$[Ru(bpy)_2(1)(H_2O)]^{2+}$.

With continued irradiation the absorption at 444 nm decreases, with an increase in the intensity of the peak at 490 nm ($\epsilon$=9,300 cm$^{-1}$) known to correspond to cis-$[Ru(bpy)_2(H_2O)_2]^{2+}$. Although not measured directly, facile release of 1 from V was implied in enzyme studies (described below). The photochemistry of V is similar to that of numerous related complexes, including cis-$[Ru(bpy)_2(MeCN)_2]^{2+}$ and cis-$[Ru(bpy)_2(5\text{-cyanouracil})_2]^{2+}$ (Liu et al., J. Am. Chem. Soc. 2009, 131, 26-27; Pinnick et al., Inorg. Chem. 1984, 23, 1440-1445). The quantum yield for the disappearance of the reactant 2 (R) to form the mono-aqua intermediate (I), $\Phi_{R \to I}$, was measured at early reaction times to be 0.080(4), whereas that determined for the formation of the product cis-$[Ru(bpy)_2(H_2O)_2]^{2+}$ (P) from V ($\Phi_{R \to P}$) was 0.00091(7). From these values, the quantum yield of the second step of the reaction, $\Phi_{I \to P}$, can be calculated to be 0.011(1). The overall photoaquation quantum yield, $\Phi_{R \to P}$, is significantly smaller than that reported for cis-$[Ru(bpy)_2(MeCN)_2]Cl_2$, 0.21 ($\lambda_{irr}$=400 nm), but similar to that measured for the formation of the mono-aqua species, $\Phi_{R \to I}$, upon irradiation of cis-$[Ru(bpy)_2(5\text{-cyanouracil})_2]Cl_2$, 0.16(4).

Figure 5:
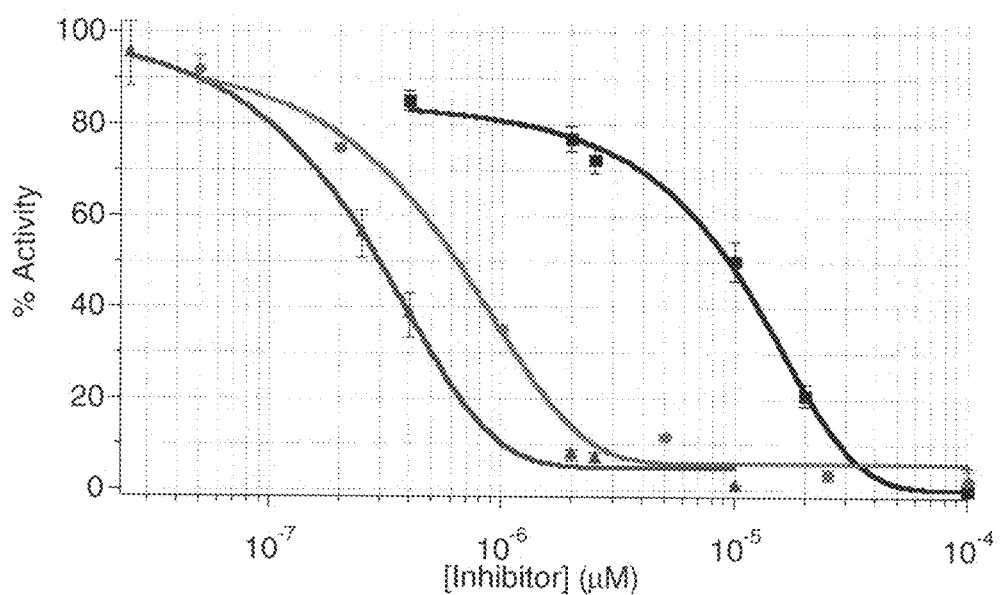
FIG. 5. IC$_{50}$ curves for 1 (middle) and 2 (with irradiation, left; without radiation, right) with the cysteine protease papain. Enzyme activity was determined with the chromogenic substrate BAPNA and is expressed as a percentage, with 100% equal to activity in the absence of inhibitor. Data points represent an average of three reactions and error bars are standard deviations. Data are representative of three independent experiments. Conditions: 0.1 M phosphate buffer, pH 6.5, 11% DMSO, [papain]=650 nM, [BAPNA]=1.0 mM, 10 min irradiation for 2 with a tungsten halogen lamp (>395 nm and H$_2$O filter, 250 W), see Example for more details.

Inhibitor 1 and complex V were evaluated for their ability to inhibit the cysteine protease papain. IC$_{50}$ values were determined for 1 and V (with and without irradiation) with enzyme (650 nM) in phosphate buffer at pH 6.5 (FIG. 5). Studies with 1 agree well with literature data (Loeser et al., J. Med. Chem. 2005, 48, 7688-7707), proving that 1 is a potent inhibitor of papain under these conditions (IC$_{50}$=638 nM; middle curve of FIG. 5). Ruthenium complex V showed more potent inhibition than 1 (IC$_{50}$=295 nM) upon irradiation with visible light for 10 minutes (FIG. 5, left curve), consistent with its release of >1 equiv of 1. Complex V in the dark was significantly less potent than 1, with an IC$_{50}$=9.5 μM, indicating that inhibition by V was enhanced 32 fold between light vs. dark conditions, and can be enhanced about 40 fold for various complexed nitriles. When TPA is used as the ligand, inhibition enhancement can be greater than more than twice that of the Ru(bpy)$_2$ complexes, up to about 89 fold enhancement.

Inhibition by V in the dark may indicate that a small amount of 1 (<5%) is released from V under the reaction conditions. Alternatively, these data may indicate that V acts as a weak inhibitor of papain using non-bonding interactions between the peptide and/or $Ru^{II}(bpy)_2$ groups and the enzyme. Control experiments proved that $[Ru^{II}(bpy)_2(MeCN)_2](PF_6)_2$ is not a potent inhibitor (IC$_{50}$>500 μM) and shows the same profile under light and dark conditions, which is consistent with released 1, rather than the ruthenium byproduct, being most responsible for the inhibition observed by V. Enzyme inhibition or inactivation due to $^1O_2$ is not likely due to the short lifetime of the excited state and the similar level of inhibition observed for [Ru$^{II}$(bpy)$_2$(MeCN)$_2$](PF$_6$)$_2$ under light and dark conditions. In conclusion, the level of enhancement observed under light and dark conditions indicates that the nitrile-based inhibitors are efficiently caged by the Ru$^{II}$ center in V, and are not susceptible to attack by the active site cysteine thiolate of papain.

Cathepsins B, K and L were then examined for photoinduced inhibition with V. IC$_{50}$ values for 1 and V (with and without irradiation) were determined in aqueous buffer at pH 5.5 for cathepsins L and K, and pH 6.0 for cathepsin B using fluorogenic substrates selective for each enzyme (Table 1). These data reveal that although inhibitor 1 is significantly less potent against cathepsins B, K and L compared to papain, in all cases a significant enhancement of inhibition was observed for V under light vs. dark conditions. Control experiments show some level of inhibition by [Ru$^{II}$(bpy)$_2$(MeCN)$_2$](PF$_6$)$_2$, which may explain the lower ratios for dark vs. light conditions observed with cathepsins vs. papain. Nonetheless, light-activated compound V was more potent than 1 under all conditions, which is again consistent with V releasing two equiv of inhibitor 1.

TABLE 1

IC$_{50}$ values (µM) for 1 and V (with and without irradiation) for human cathepsins B, L and K with ratios under light vs. dark conditions.

| human cathepsin | 1 | V (dark) | V (light) | dark/light ratio |
|---|---|---|---|---|
| B | 133 | 892 | 63 | 14 |
| K | 12 | 176 | 5.4 | 33 |
| L | 72 | 225 | 40 | 5.6 |

The IC$_{50}$ values represent the average from three independent experiments. Standard deviations for these assays were typically within 40% of the IC$_{50}$ values. Activities were plotted against log [inhibitor] and fit to a sigmoidal curve to calculate the IC$_{50}$ values, with 100% activity equal to the activity of the control reaction in the absence of inhibitor. Activities were determined with the fluorogenic substrates Z-Arg-Arg-AMC (cathepsin B), Z-Gly-Pro-Arg-AMC (cathepsin K) and Z-Phe-Arg-AMC (cathepsin L) (where AMC is aminomethylcoumarin). Substrate concentrations were 100 µM. Reactions were conducted in the dark or after 10 minutes irradiation for V with a tungsten halogen lamp (H$_2$O filter, 250 W). Cathepsin B conditions: 0.4 M acetate buffer, pH 6.0, 4 mM EDTA, 8 mM DTT, [cat B]=8 nM; Cathepsin K and L conditions: 0.4 M acetate buffer, pH 5.5, 4 mM EDTA, 8 mM DTT, [cat K or L]=20 nM. Final solutions contained 1% DMSO. See Example 3 for more details.

Light-triggered cathepsin inhibition with V was further extended to a series of human cell lysates. Specifically examined were lysates from DU145 prostate carcinoma cells derived from brain metastases, which exhibit significant cathepsin B activity, and lysates from primary human bone marrow stromal cells (hBMSC), an important source of cathepsin activity that modulates progression of metastatic cancer in bone (Podgorski et al., *Am. J. Pathol.* 2009, 175, 1255-1269). Activities associated with cathepsin K and L were significantly lower than those associated with cathepsin B. Therefore the cathepsin B selective substrate Z-Arg-Arg-AMC was used in all subsequent experiments, and cathepsin B activity was determined for DU145 and hBMSC lysates with 1 and V under light and dark conditions (Table 2).

TABLE 2

IC$_{50}$ values (µM) for 1 and V (with and without irradiation) for human cathepsins B in lysates with ratios under light vs. dark conditions.

| Lysate | 1 | V (dark) | V(light) | dark/light ratio |
|---|---|---|---|---|
| DU145 | 182 | 658 | 82 | 8.0 |
| hBMSC | 183 | 580 | 88 | 6.6 |

The IC$_{50}$ values observed for human cathepsin B in DU145 lysates were close to those observed for hMBSCs, indicating similar levels of cathepsin B activity. In addition, these values were in agreement with results observed for isolated enzymes (Table 1), confirming that inhibition with 2 can be activated efficiently with light in lysates. The experimental methods were analogous to those described above for Table 1. Activities were determined in DU145 and hBMSC lysates using the fluorogenic substrate Z-Arg-Arg-AMC. Reactions were conducted in the dark or after 10 minutes irradiation for V with a tungsten halogen lamp (>390 nm and H$_2$O filter, 250 W). See Example 3 for more details.

In conclusion, caging and light-activated release of a nitrile-based cysteine protease inhibitor with a ruthenium complex has been achieved. This method allows inhibitor activation with high levels of selectivity between light and dark conditions. This method can be extended to a variety of more potent nitrile-based inhibitors. This method thus provides novel methods to achieve kinetic control over protease activity that is useful for chemical biology and anticancer applications.

Example 3

Analysis of Cysteine Protease Inhibitors and Methods

A. Stability and Photoreactivity Studies.

Stability of 2 in 0.1M phosphate buffer pH 6.5 (0.5% DMSO) or DMSO. Solutions of 2 (25 µM) in 0.1 M phosphate buffer pH 6.5 (0.5% DMSO) or DMSO were monitored for decomposition by UV-Vis spectroscopy at rt (~23° C.) by following absorbance at 422 nm. First-order rate constants for decomposition of V were calculated using slopes of ln A$_{422}$ vs. time graphs. Rate constants were determined to be 2.3×10$^{-7}$ s$^{-1}$ (0.1 M phosphate buffer pH 6.5, FIG. 2) and 2.8×10$^{-7}$ s$^{-1}$ (DMSO, FIG. 3). These values correspond to t$_{1/2}$ of 35 and 29 days, respectively.

Quantum Yield and Time Dependent UV-Vis Spectra Upon Irradiation of V. Steady-state photolysis experiments for quantum yield determination were conducted using a 150 W Xe arc lamp in a PTI housing (Milliarc Compact Lamp Housing) powered by an LPS-220 power supply (PTI) with an LPS-221 igniter (PTI) as a source. The irradiation wavelength was selected by placing long-pass colored glass filters (Melles Griot) or bandpass filters (Newport) between the lamp and the sample, along with a 10 cm water cell to absorb infrared light. Electronic absorption spectra were collected on a diode array spectrometer (HP 8453) with HP 8453 Win System software.

Quantum yields were measured relative to ferrioxalate using a standard procedure (Montalti et al.; Editors, *Handbook of Photochemistry—Third Edition*; CRC Press LLC, 2006). The quantum yield of reactant (R) to intermediate (I), $\Phi_{R \to I}$, was determined by monitoring the decrease in the Metal to Ligand Charge Transfer (MLCT) absorption of the reactant at 414 nm up to 5% of the reaction. The quantum yield of reactant (R) to product (P), $\Phi_{R \to P}$, was determined by monitoring the increase in the absorption of the latter with maximum at 490 nm. The quantum yield of intermediate (I) to product (P), $\Phi_{I \to P}$, was calculated using the equation $\Phi_{R \to P} = \Phi_{R \to I} \cdot \Phi_{I \to P}$.

The electronic absorption spectrum of cis-[Ru(bpy)$_2$(1)$_2$] (PF$_6$)$_2$ exhibits ligand-centered (LC) bpy $\pi\pi^*$ and Ru→bpy MLCT absorption peaks at 281 nm ($\epsilon$=54430 M$^{-1}$ cm$^{-1}$) and 414 nm ($\epsilon$=8760 M$^{-1}$ cm$^{-1}$), respectively, in a 1% DMSO aqueous solution. Similar transition energies and intensities have been reported for the related complexes cis-[Ru(bpy)$_2$(CH$_3$CN)$_2$](PF)$_6$ and cis-[Ru(bpy)$_2$(5cnu)$_2$]Cl$_2$ (5cnu=5-cyanouracil). The former exhibits absorption maxima at 283 nm ($\epsilon$=52500 M$^{-1}$ cm$^{-1}$) and 425 nm ($\epsilon$=8590 M$^{-1}$ cm$^{-1}$) in CH$_3$CN (Brown et al., *Inorg. Chem.* 1975, 14, 1915-1921) and at 427 nm ($\epsilon$=8900 M$^{-1}$ cm$^{-1}$) in water (Liu et al., *J. Am. Chem. Soc.* 2009, 131, 26-27), and for the latter maxima were reported at 284 nm ($\epsilon$=48300 cm$^{-1}$) and 410 nm ($\epsilon$=7800 M$^{-1}$ cm$^{-1}$) in H$_2$O (Garner et al., *Inorg. Chem.* 2011, 50, 9213-9215).

B. Enzyme Inhibition Studies.

Papain Inhibition Studies. The inhibition studies with papain were carried out following a modified procedure by Gütschow and coworkers (Löser et al., *J. Med. Chem.* 2005, 48, 7688-7707). Enzyme activity was determined with the chromogenic substrate BAPNA (Z-Phe-Arg-NHNp) and is expressed as a percentage, with 100% equal to activity in the absence of inhibitor. A 0.25 mM papain stock solution was prepared in 0.1 mM HCl and kept frozen. For each experiment, the stock solution was diluted 250 times and activated for 45 min at 25° C. with a 0.1 M phosphate pH 6.5, 15 mM DTT and 2.5 mM EDTA buffer solution. A 10.0 mM solution of BAPNA in DMSO was prepared daily and plated (final concentration 1.0 mM). The inhibitor was plated as a 1% DMSO solution in the assay buffer. All three experiments in triplicates (1, V in the dark, and V photolyzed) were plated on the same 96 well plate. The wells containing 1 and V "dark" were carefully wrapped in aluminum foil and the plate exposed to visible light.

The photolysis was conducted for 10 minutes (with gentle shaking of the plate every 2-3 minutes) using a 250 W tungsten halogen lamp (Osram Xenophot HLX) powered by a 24 V power supply. The irradiation wavelength was selected by placing a bandpass filter (395 nm cutoff) between the lamp and the sample, along with a 10 cm water cell to absorb infrared light. After photolysis, the reaction was initiated by addition of 65 μL of enzyme (final volume 100 μL, final enzyme concentration 0.65 μM). The absorbance changes due to the hydrolysis product p-nitroaniline (pNA) were measured at 405 nm every 2 min for 14 min (8 measures) at 25° C.

Cathepsin Inhibition Studies. Cathepsin enzyme activity was determined from kinetic measurements performed by fluorometric detection of the hydrolysis product aminomethylcoumarin (AMC) at 37° C. every 2 min for 14 min (8 measures). The excitation and emission wavelengths were 360 and 485 nm respectively. Selective fluorescent substrate Z-Arg-Arg-AMC for cathepsin B, Z-Phe-Arg-AMC for cathepsin L, and Z-Gly-Pro-Arg-AMC for cathepsin K were used at a final concentration of 100 μM (all obtained from Bachem). Enzyme activities are expressed as a percentage, with 100% equal to activity in the absence of inhibitor.

Cathepsin B. Purified cathepsin B (human liver) was obtained from Enzo Life Sciences and a 5 μM stock solution was prepared in 50 mM sodium acetate, pH 5.0, 1 mM EDTA and kept at −80° C. For each experiment the stock solution was diluted 625 times and activated for 15 minutes at 37° C. with a 400 mM sodium acetate, pH 6.0, 4 mM EDTA, 8 mM DTT assay buffer solution. The inhibitor was prepared as a 1% DMSO solution in the activated enzyme buffer solution and plated (50 μL). All three experiments in triplicates (1, V in the dark, and V photolyzed) were plated on the same 96 well plate. The wells containing 1 and V "dark" were carefully wrapped in aluminum foil and the plate was exposed to visible light.

Figure 6:
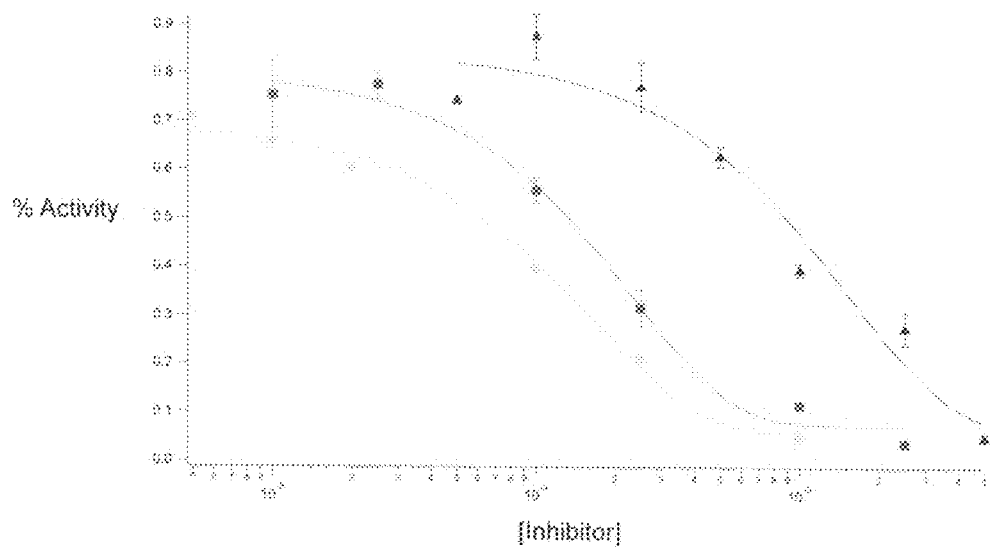
FIG. 6. IC$_{50}$ curve for cathepsin B with 1 (red; middle line), 2 light (yellow; left line), and 2 dark (blue; right-hand line).

The photolysis was conducted for 10 min (with gentle shaking of the plate every 2-3 min) using a 250 W tungsten halogen lamp (Osram Xenophot HLX) powered by a 24 V power supply. The irradiation wavelength was selected by placing a bandpass filter (395 nm cutoff) between the lamp and the sample, along with a 10 cm water cell to absorb infrared light. After photolysis, the reaction was initiated by addition of 50 μL of 200 μM Z-Arg-Arg-AMC solution in the assay buffer (final volume 100 μL, final enzyme concentration 4 nM). Cathepsin enzyme activity was determined from kinetic measurements performed by fluorometric detection of the hydrolysis product AMC at 37° C. every 2 min for 14 min (8 measures) and MAX RFU slope values used for plotting (FIG. 6).

Cathepsin K. Recombinant cathepsin K (human) was obtained from Enzo Life Sciences as a 880 nM stock solution in 50 mM sodium acetate, pH 5.5, 50 mM NaCl, 0.5 mM EDTA and 5 mM DTT and kept at −80° C. For each experiment the stock solution was diluted 44 times and activated for 15 minutes at 37° C. with 400 mM sodium acetate, pH 5.5, 4 mM EDTA, 8 mM DTT assay buffer solution. The inhibitor was prepared as a 1% DMSO solution in the activated enzyme buffer solution and plated (50 μL). All three experiments in triplicates (1, V in the dark, and V photolyzed) were plated on the same 96 well plate. The wells containing 1 and V "dark" were carefully wrapped in aluminum foil and the plate exposed to visible light.

Figure 7:
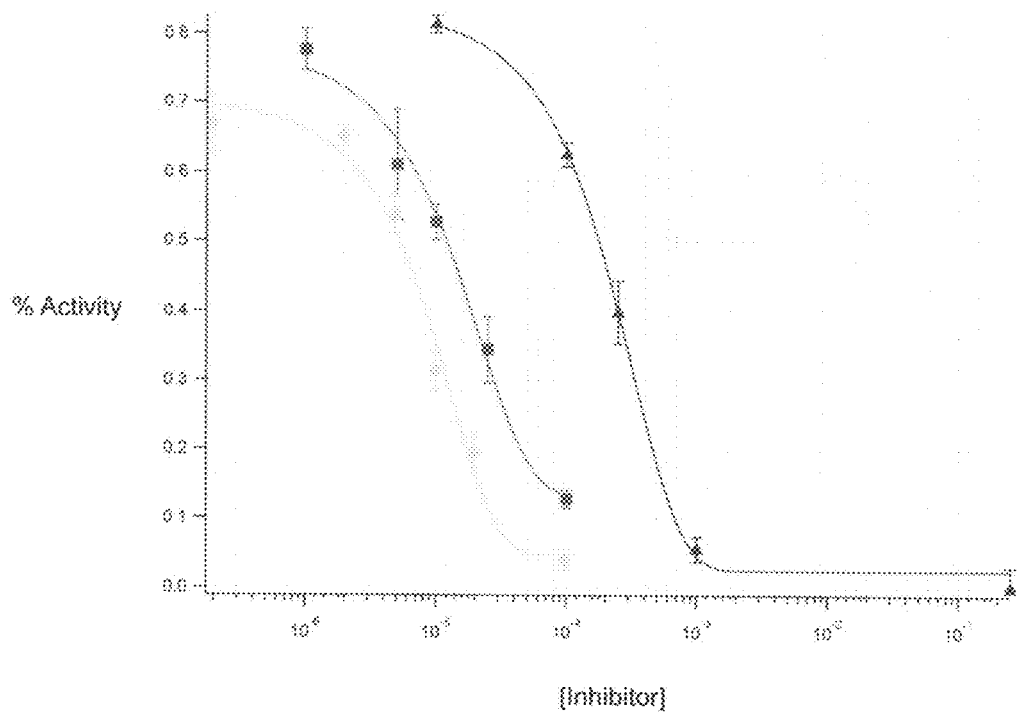
FIG. 7. IC$_{50}$ curve for cathepsin K with 1 (red; middle line), 2 light (yellow; left line), and 2 dark (blue; right-hand line).

The photolysis was conducted for 10 minutes (with gentle shaking of the plate every 2-3 min) using a 250 W tungsten halogen lamp (Osram Xenophot HLX) powered by a 24 V power supply. The irradiation wavelength was selected by placing a bandpass filter (395 nm cutoff) between the lamp and the sample, along with a 10 cm water cell to absorb infrared light. After photolysis, the reaction was initiated by addition of 50 μL of 200 μM Z-Gly-Pro-Arg-AMC solution in the assay buffer (final volume 100 μL, final enzyme concentration 10 nM). Cathepsin enzyme activity was determined from kinetic measurements performed by fluorometric detection of the hydrolysis product AMC at 37° C. every 2 min for 14 min (8 measures) and MAX RFU slope values used for plotting (FIG. 7).

Cathepsin L. Cathepsin L was obtained from Sigma as a 10 μM stock solution in 20 mM malonate, pH 5.5, 1 mM EDTA, 400 mM NaCl and kept at −80° C. For each experiment the stock solution was diluted 500 times and activated for 15 minutes at 25° C. with 400 mM sodium acetate, pH 5.5, 4 mM EDTA, 8 mM DTT assay buffer solution. The inhibitor was prepared as a 1% DMSO solution in the activated enzyme buffer solution and plated (50 μL). All three experiments in triplicates (1, V in the dark, and V photolyzed) were plated on the same 96 well plate. The wells containing 1 and V "dark" were carefully wrapped in aluminum foil and the plate exposed to visible light.

Figure 8:
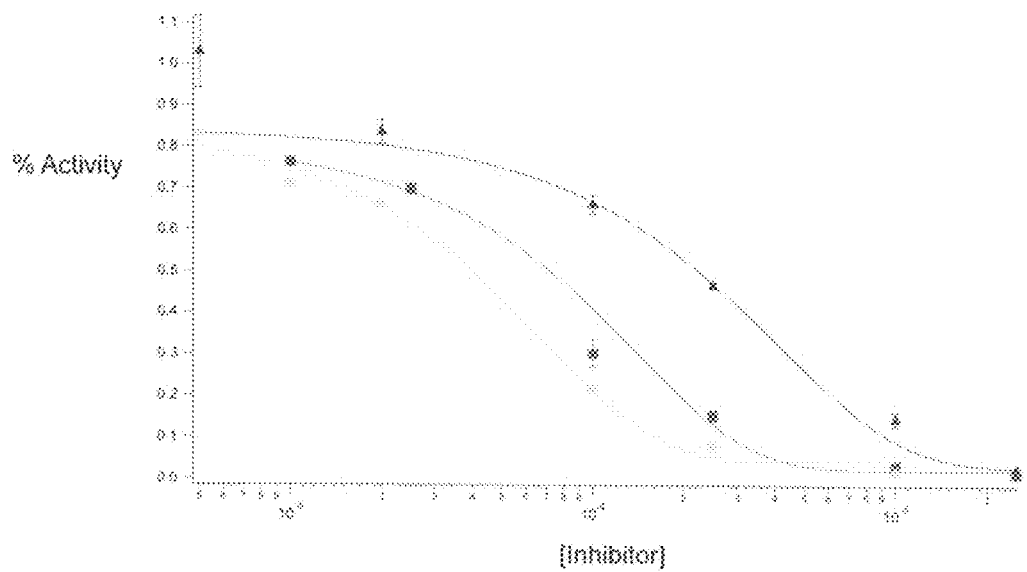
FIG. 8. IC$_{50}$ curve for cathepsin L with 1 (red; middle line), 2 light (yellow; left line), and 2 dark (blue; right-hand line).

The photolysis was conducted for 10 minutes (with gentle shaking of the plate every 2-3 min) using a 250 W tungsten halogen lamp (Osram Xenophot HLX) powered by a 24 V power supply. The irradiation wavelength was selected by placing a bandpass filter (395 nm cutoff) between the lamp and the sample, along with a 10 cm water cell to absorb infrared light. After photolysis, the reaction was initiated by addition of 50 μL of 200 μM Z-Phe-Arg-AMC solution in the assay buffer (final volume 100 μL, final enzyme concentration 10 nM). Cathepsin enzyme activity was determined from kinetic measurements performed by fluorometric detection of the hydrolysis product AMC at 37° C. every 2 min for 14 min (8 measures) and MAX RFU slope values used for plotting (FIG. 8).

Example 4

Inhibition Studies in Human Cell Lysates

DU145 lysates (an androgen-independent osteolytic line derived from a brain metastasis). DU145 cells were purchased from American Type Culture Collection (ATCC; Manassas, Va.) and were cultured in Dulbecco's modified Eagle's medium (DMEM) (Sigma; St. Louis, Mo.) supplemented with 10% fetal bovine serum (FBS) (Invitrogen; Carlsbad, TCA) according to ATCC guidelines. Cells were maintained in a 37° C. humidified incubator ventilated with 5% $CO_2$. Lysates were obtained by culturing cells to roughly 80% confluency on uncoated 100-$mm^2$ tissue culture dishes. Cells were then washed with phosphate-buffered saline (PBS), scraped and collected in 250 mM sucrose, 25 mM MES, 1 mM EDTA, pH 6.5, and 0.1% Triton X-100 (SME). Cells were lysed by gentle sonication followed by passing through a 26-gauge needle.

Figure 9:
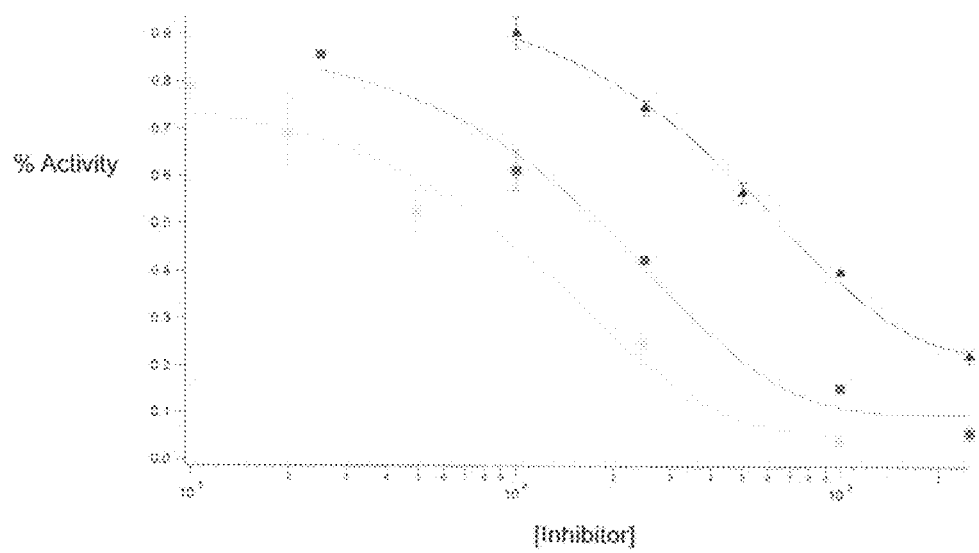
FIG. 9. IC$_{50}$ curve for cathepsin B activity from DU154 lysates with 1 (red; middle line), 2 light (yellow; left line), and 2 dark (blue; right-hand line).

For each experiment the lysates in SME were diluted 8 times with assay buffer solution containing 400 mM sodium acetate, pH 5.5, 4 mM EDTA, and 8 mM DTT. The inhibitor was prepared as a 1% DMSO solution in the activated lysates buffer solution and plated (50 µL). All three experiments in triplicates (1, V in the dark, and 2 photolyzed) were plated on the same 96 well plate. The wells containing 1 and V "dark" were carefully wrapped in aluminum foil and the plate exposed to visible light. The photolysis was conducted for 10 minutes (with gentle shaking of the plate every 2-3 min) using a 250 W tungsten halogen lamp (Osram Xenophot HLX) powered by a 24 V power supply. The irradiation wavelength was selected by placing a bandpass filter (395 nm cutoff) between the lamp and the sample, along with a 10 cm water cell to absorb infrared light. After photolysis, the reaction was initiated by addition of 50 µL of 200 µM Z-Arg-Arg-AMC solution in the assay buffer (final volume 100 µL). Cathepsin enzyme activity was determined from kinetic measurements performed by fluorometric detection of the hydrolysis product AMC at 37° C. every 2 min for 14 min (8 measures) and MAX slope values used for plotting (FIG. 9).

Example 5

Human Bone Marrow Stromal Cell (hBMSC) lysates

Human bone marrow stromal cells (hBMSC) were derived from human male fetal femurs as previously described (Podgorski et al., *Am. J. Pathol.* 2009, 175, 1255-1269). Cells were cultured in DMEM supplemented with 10% FBS, and maintained in a 37° C. humidified incubator ventilated with 5% $CO_2$. Lysates were obtained by culturing cells to roughly 80% confluency on uncoated 100-$mm^2$ tissue culture dishes. Cells were then washed with phosphate-buffered saline (PBS), scraped and collected in 250 mM sucrose, 25 mM MES, 1 mM EDTA, pH 6.5, and 0.1% Triton X-100 (SME). Cells were then lysed by sonication and by passing through a 26-gauge needle.

Figure 10:
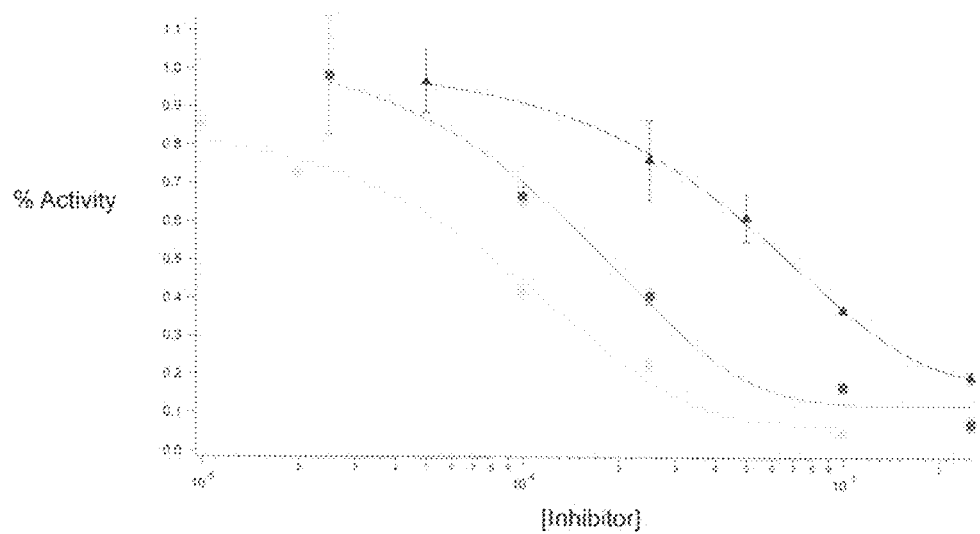
FIG. 10. IC$_{50}$ curve for cathepsin B activity from hBMSC lysates with 1 (red; middle line), 2 light (yellow; left line), and 2 dark (blue; right-hand line).

For each experiment the lysates in SME were diluted 8 times with assay buffer containing 400 mM sodium acetate, pH 5.5, 4 mM EDTA, and 8 mM DTT. The inhibitor was prepared as a 1% DMSO solution in the activated lysates buffer solution and plated (50 µL). All three experiments in triplicates (1, V in the dark, and V photolyzed) were plated on the same 96 well plate. The wells containing 1 and V "dark" were carefully wrapped in aluminum foil and the plate exposed to visible light. The photolysis was conducted for 10 minutes (with gentle shaking of the plate every 2-3 min) using a 250 W tungsten halogen lamp (Osram Xenophot HLX) powered by a 24 V power supply. The irradiation wavelength was selected by placing a bandpass filter (395 nm cutoff) between the lamp and the sample, along with a 10 cm water cell to absorb infrared light. After photolysis, the reaction was initiated by addition of 50 µL of 200 µM Z-Arg-Arg-AMC solution in the assay buffer (final volume 100 µL). Cathepsin enzyme activity was determined from kinetic measurements performed by fluorometric detection of the hydrolysis product AMC at 37° C. every 2 min for 14 min (8 measures) and MAX slope values used for plotting (FIG. 10).

Synthesis and Characterization. In order to translate the light-activated method to living cells, a more potent nitrile-based inhibitor for cathepsin K than compound 1 was located, which was caged the initial study (Scheme 4). Literature data confirmed that subtle modifications of the dipeptidyl inhibitor structure of 1 can lead to significant enhancements for inhibition of cathepsin K. Compound 2 was chosen, because replacing the N-protecting group and side chain in a straightforward manner gives an inhibitor with a $K_i$ for cathepsin K of 35 nM, almost three orders of magnitude lower than that of 1 ($K_i$=7.5 µM). Furthermore, compound 2 was shown previously to inhibit cathepsin K activity in a live cell assay, and 2 is available in one step from commercially available starting materials Cbz-Leu-OH and aminoacetonitrile hydrochloride.

Scheme 4.
Nitrile-based cathepsin K inhibitors from the literature with reported $K_i$ values

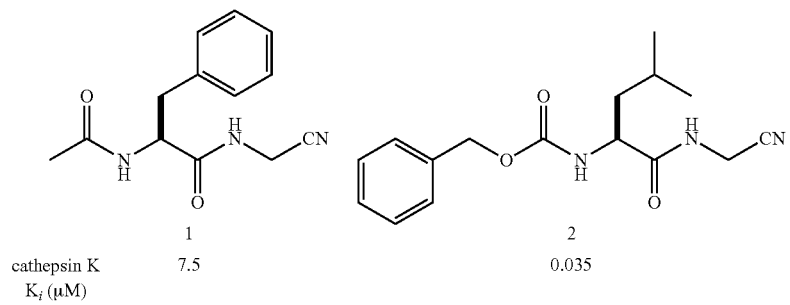

| | 1 | 2 |
|---|---|---|
| cathepsin K $K_i$ (µM) | 7.5 | 0.035 |

Synthesis of the caged inhibitor cis-[Ru(bpy)$_2$(2)$_2$]Cl$_2$ (VI), derived from 2, proceeded cleanly (Scheme 5). Treating cis-Ru(bpy)$_2$Cl$_2$ with 2 (6.0 equiv) and AgBF$_4$ (4.0 equiv) in EtOH at 80° C. for 5 h resulted in a color change from violet to orange. After cooling the reaction mixture to −20° C., filtering and concentrating, analysis of the crude mixture by $^1$H NMR spectroscopy confirmed that 2 was bound to ruthenium with high conversion, as there were no ruthenium byproducts evident. In order to remove excess 2 and purify the complex VI, the crude solid was dissolved in EtOAc saturated with n-Bu$_4$NCl. Upon cooling to −20° C., an orange oily residue formed that was washed with EtOAc and toluene. Subsequent precipitation from acetone and Et$_2$O, followed by drying in vacuo, supplied the caged inhibitor 3 in analytically pure form.

Scheme 5. Synthesis of caged inhibitor VI.

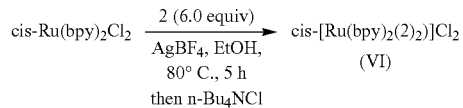

Figure 12:
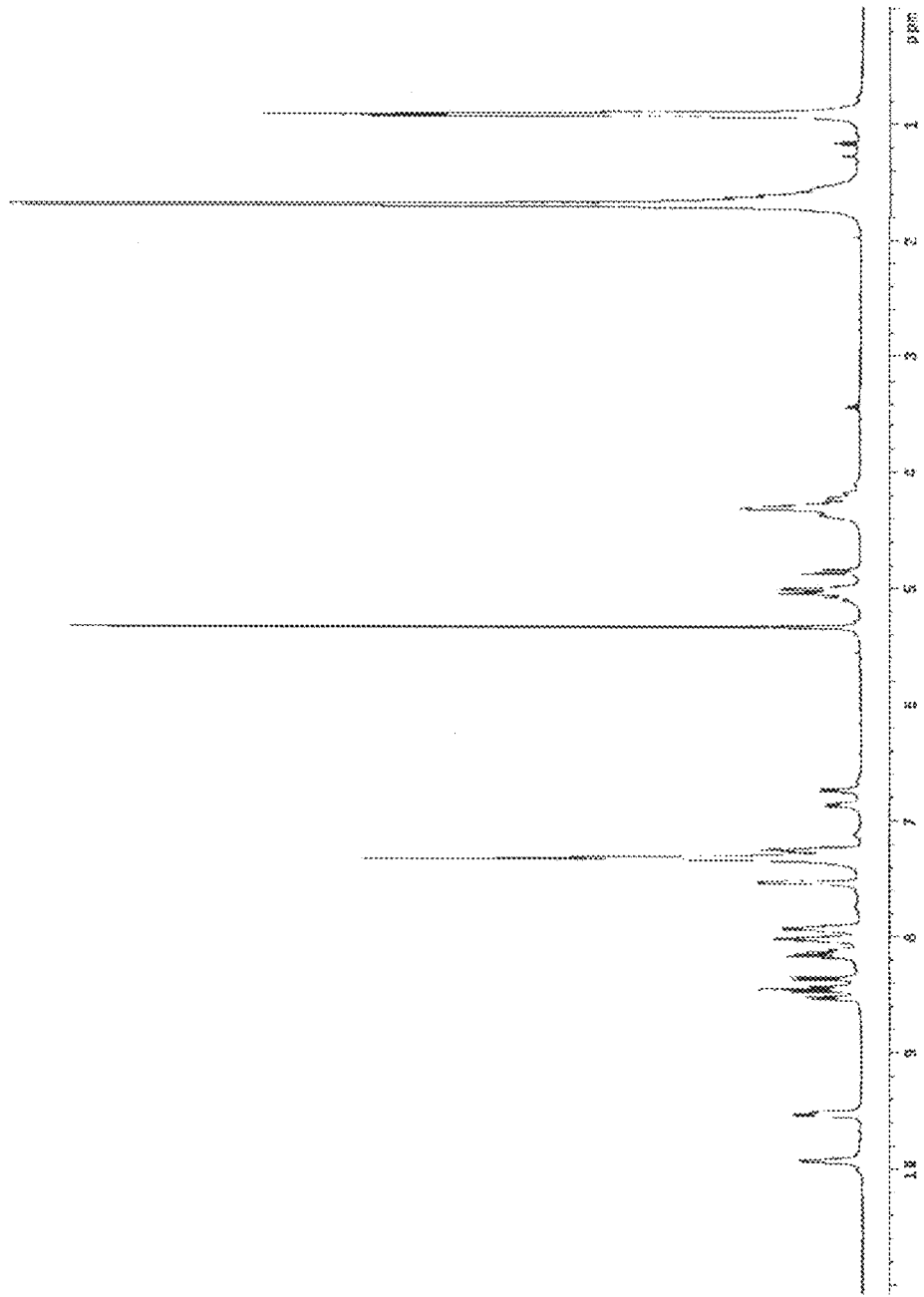
FIG. 12. 1H NMR spectrum of VI, including amide protons at 6.86 and 6.74 ppm.

Complex VI was characterized by $^1$H NMR, IR and UV-vis spectroscopies, mass spectrometry and elemental analysis. As expected, VI was isolated as a 1:1 mixture of (Λ, S, S) and (Δ, S, S) isomers, because cis-Ru(bpy)$_2$Cl$_2$ and 2 are both chiral. Shifts between 9.93 and 0.91 ppm were observed in the $^1$H NMR spectrum of VI, with splitting of select resonances due to the presence of diastereoisomeric complexes, including amide protons at 6.86 and 6.74 ppm (FIG. 12). The IR spectrum of VI shows a $\nu_{CN}$ stretch at 2274 cm$^{-1}$, which is shifted by ~20 cm$^{-1}$ relative to 2 ($\nu_{CN}$=2258 cm$^{-1}$), consistent with data for other nitriles bound to the ruthenium center of Ru(bpy)$_2$. The electrospray ionization mass spectrum of VI in H$_2$O shows a prominent peak at m/z=510.1, consistent with a predication of the formula [Ru(bpy)$_2$(2)$_2$]$^{2+}$. The electronic absorption spectrum of VI in water containing 1% DMSO (FIG. 13, reactant trace) exhibits maxima at 281 nm ($\epsilon$=55,600 M$^{-1}$ cm$^{-1}$) associated with the ligand-centered bpy $^1\pi\pi^*$ transitions and at 412 nm ($\epsilon$=9,600 M$^{-1}$ cm$^{-1}$) nm assigned as arising from Ru→bpy metal-to-ligand charge transfer ($^1$MLCT). These peak positions are in good agreement with those of related nitrile-bound ruthenium complexes, including cis-[Ru(bpy)$_2$(1)$_2$](PF$_6$)$_2$,[23] cis-[Ru(bpy)$_2$(MeCN)$_2$](PF$_6$)$_2$,[25] and cis-[Ru(bpy)$_2$(5-cyanouracil)$_2$]Cl$_2$. Irradiation into the $^1$MLCT band in these complexes results in ligand exchange in coordinating solvents.

Figure 13:
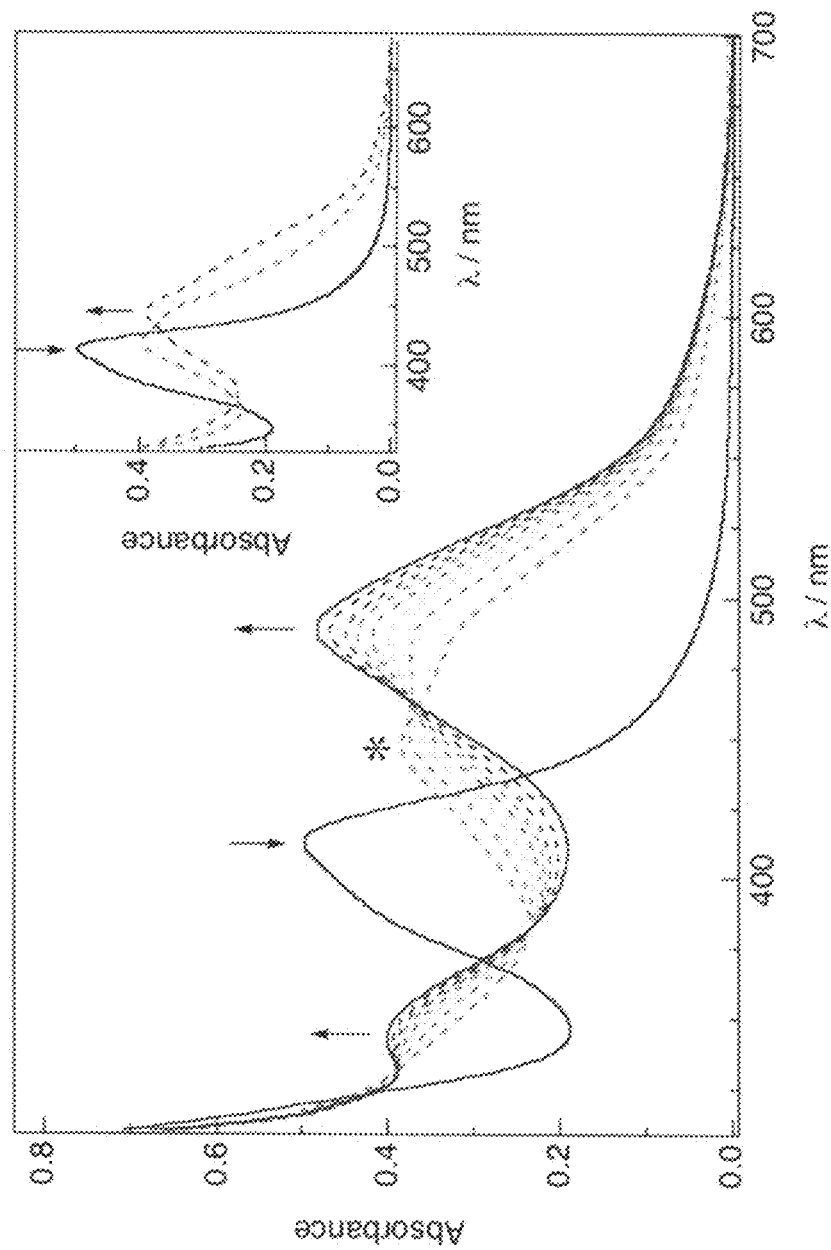
FIG. 13. Changes to the electronic absorption of 52 µM of VI in a 1% DMSO aqueous solution at irradiation times of 0, 3, 4, 5, 6, 7, 8, 10, and 15 min ($\lambda_{irr}$≥395 nm); * denotes the absorption maximum of the intermediate. Inset: 0, 1, and 2 min.

Complex VI shows properties ideal for acting as a biological tool, including high stability in buffer in the dark and fast release of inhibitor 2 upon irradiation with visible light. The half-life for VI was determined spectrophotometrically in phosphate (PBS) buffer (pH 6.5) to be ~8.0 days at 293±2K, as determined using the rate constant for decomposition of VI obtained from the slope of a ln A vs t graph ($k_{obs}$=1.0×10$^{-6}$ s$^{-1}$). Similar stability in the dark was recorded in pure water and in solutions containing 1% DMSO, which resemble the conditions used in the biological assays. Photolysis of VI in water (1% DMSO) results in the sequential exchange of the two monodentate ligands for solvent molecules, generating cis-[Ru(bpy)$_2$(H$_2$O)$_2$]$^{2+}$. The changes in the electronic absorption spectrum of VI (52 μM) as a function of irradiation time ($\lambda_{irr}$≥395 nm) show the decrease of the reactant peak at 412 nm and the formation of an intermediate species in t$_{irr}$=0-3 min with maximum at ~450 nm (FIG. 13, inset). During this time, two isosbestic points at 322 and 364 nm are apparent, as well as a pseudo-isosbestic point at 427 nm. The intermediate at t$_{irr}$=2-3 min has been shown to correspond to the product formed after the exchange of one CH$_3$CN ligand for a H$_2$O molecule in the CH$_3$CN complex, i.e. cis-[Ru(bpy)$_2$(CH$_3$CN)(H$_2$O)]$^{2+}$, and is denoted by * in FIG. 13. Further irradiation of VI from 3 min to 15 min leads to the formation of the final product, cis-[Ru(bpy)$_2$(H$_2$O)$_2$]$^{2+}$, with the known absorption maxima at 340 nm and 486.32 Three isosbestic points at 332, 384, and 463 nm are evident in FIG. 2 during the second step of the photolysis (t$_{irr}$=3-15 min).

The quantum yield for the conversion of the reactant (R) VI to the intermediate (II) cis-[Ru(bpy)$_2$(2)(H$_2$O)]$^{2+}$($\Phi_{R\to I}$) and to the product (P) cis-[Ru(bpy)$_2$(H$_2$O)$_2$]$^{2+}$($\Phi_{R\to P}$) were determined, as previously described for cis-[Ru(bpy)$_2$(1)$_2$] (PF$_6$)$_2$,23 to be 0.050(6) and 0.0067(4), respectively ($\lambda_{irr}$=400 nm). These values are significantly lower than those reported for the photoaquation of the related complex [Ru(bpy)$_2$(CH$_3$CN)$_2$]$^{2+}$,[25] but are similar to those measured for cis-[Ru(bpy)$_2$(1)$_2$](PF$_6$)$_2$.

Example 6

Light-Activated Inhibition of Cathepsin K

IC$_{50}$ values were determined for VI and the parent inhibitor 2 against purified human cathepsin K under light and dark conditions (FIG. 3). Solutions of cathepsin K (2 nM) in assay buffer solutions (400 mM sodium acetate, pH 6.0, 4 mM EDTA, 8 mM DTT) were treated with varying amounts of 2 or VI. Solutions were left in the dark or irradiated for 15 min with a tungsten halogen lamp (250 W, $\lambda_{irr}$>395 nm, H$_2$O filter). Enzyme activities were determined following addition of the fluorogenic substrate Z-Phe-Arg-AMC. Data indicate that 2 blocks enzyme activity in the nanomolar range under these conditions (IC$_{50}$=550 nM), and no differences were noted for inhibition under light vs. dark conditions. Compound VI, however acts as a more potent, light-activated inhibitor for human cathepsin K, with IC$_{50}$ values of 290 nM and 2.4 μM, respectively under light and dark conditions. As expected, under light conditions VI is more potent than the parent inhibitor 2, because it carries 2 equiv of inhibitor molecule per ruthenium complex. Inhibition is enhanced significantly in the presence of light, with a dark/light ratio of 8.3 for the IC$_{50}$ values. As previously noted with cis-[Ru(bpy)$_2$(1)$_2$](PF$_6$)$_2$, background inhibition by VI in the dark could be due to a small amount of inhibitor being released from its Ru(bpy)$_2$ cage, or alternatively it may be due to direct inhibition of cathepsin K by VI, presumably due to non-covalent interactions with the enzyme. Nonetheless, compound 3 represents a considerable improvement over light-activated inhibition by our previous compound cis-[Ru(bpy)$_2$(1)$_2$](PF$_6$)$_2$, which showed an IC$_{50}$ value of 5.4 μM, as compared to 290 nM for VI with cathepsin K.

Figure 14:
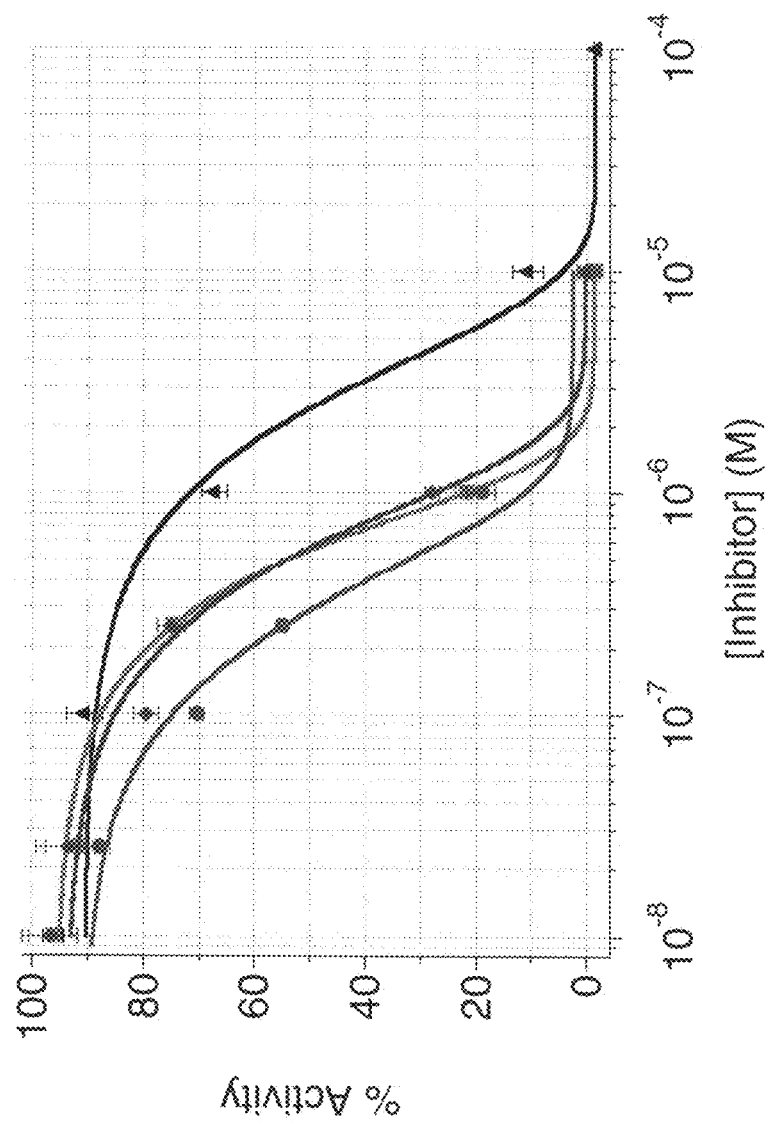
FIG. 14. IC$_{50}$ curves for inhibitor 2 (red, dark; green, light) and cis-[Ru(bpy)$_2$(2)$_2$]Cl$_2$ (VI) (black, dark; blue, light) with cathepsin K.

FIG. 14. IC$_{50}$ curves for inhibitor 2 (red, dark; green, light) and cis-[Ru(bpy)$_2$(2)$_2$]Cl$_2$ (VI) (black, dark; blue, light) with cathepsin K. Enzyme activity was determined with the fluorogenic substrate Z-Phe-Arg-AMC and is expressed as a percentage, with 100% equal to the cathepsin K activity in the absence of inhibitor. Data points represent the average of triplicate wells, and error bars are standard deviations of the mean. Data are representative of three independent experiments. Conditions: 400 mM sodium acetate, pH 6.0, 4 mM EDTA, 8 mM DTT, 1% DMSO, [cathepsin K]=1 nM, [Z-Phe-Arg-AMC]=100 μM, 15 min irradiation for 2 and VI with a tungsten halogen lamp (>395 nm and H$_2$O filter, 250 W). See Experimental Section for more details.

Example 7

Intracellular Knockdown of Cathepsin K Activity in Living Cells

Figure 15:
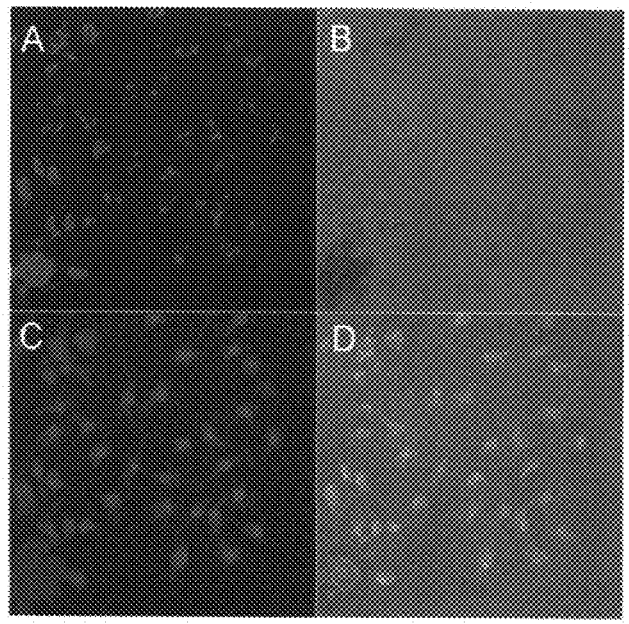
FIG. 15. Confocal microscopy images of murine osteoclasts treated with cis-[Ru(bpy)$_2$(2)$_2$]Cl$_2$ (VI). Conditions were as follows.
Figure 15:
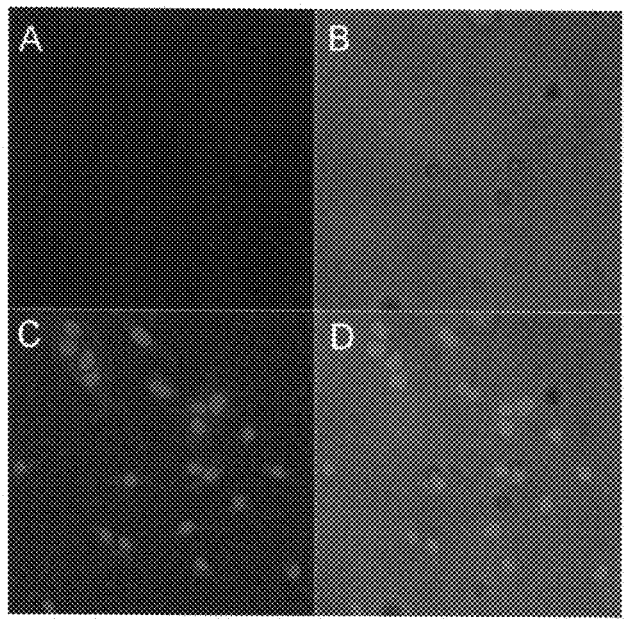
Figure 15:
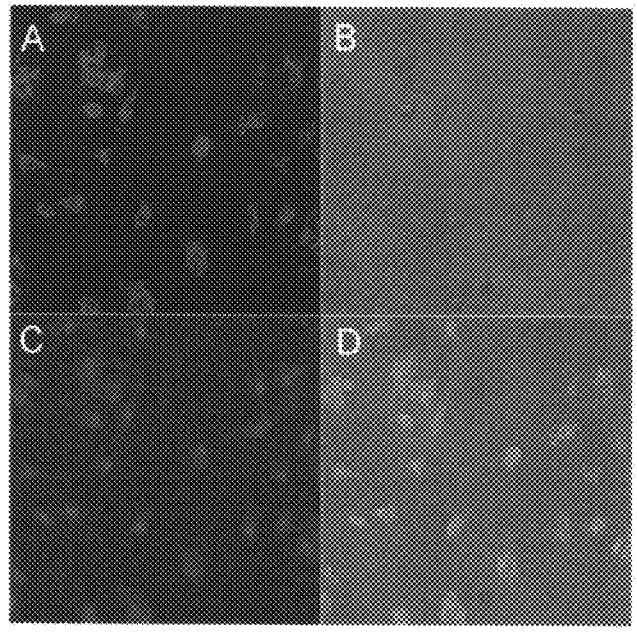
Figure 15:
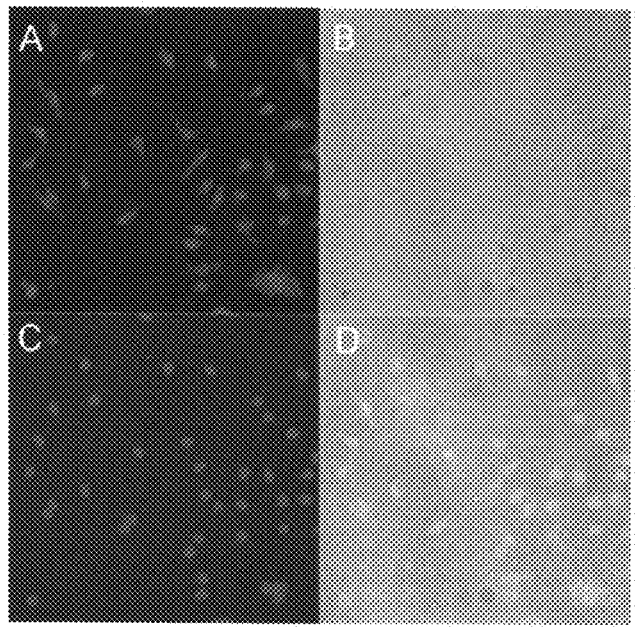

To extend our method to a live cell system, inhibition of cathepsin K by VI in murine osteoclasts was examined. Cells were preincubated with complex VI (1 nM to 1 µM), plus the epoxide-based inhibitor CA074 (1 µM) to knockdown cathepsin B activity, which enabled us to measure cathepsin K activity selectively with the fluorogenic substrate (see below). After 30 min, cells were washed to remove extracellular VI, then irradiated with visible light for 15 min or left in the dark. Cathepsin K activity was visualized by confocal microscopy using an established live cell assay, where hydrolysis of Z-Gly-Pro-Arg-4-methoxy-β-naphthylamide by this protease generates 4-methoxy-β-naphthylamine, which forms a precipitate with nitrosalicylaldehyde that can be detected and quantified by fluorescence measurements. Results in FIG. 15 show that light exposure knocked down all cathepsin K activity with 250 nM VI, whereas cells left in the dark showed similar levels of activity to controls with only buffer or the control complex cis-$[Ru(bpy)_2(MeCN)_2](PF_6)_2$ (1 µM) added. Importantly, merging green (cathepsin K activity) and blue (DAPI nuclear stain) fluorescence with DIC (differential interference contrast) images indicated that cathepsin K activity in dark cells was intracellular, and that under light conditions this activity was knocked down.

FIG. 15. Confocal microscopy images of murine osteoclasts treated with cis-$[Ru(bpy)_2(2)_2]Cl_2$ (VI). BMMs were preincubated with 250 nM complex 3 for 30 min at 37° C. in the presence of cathepsin B inhibitor CA074 (1 µM) for measuring of specific cathepsin K activity. Cells were washed and exposed to dark (no irradiation) or light (irradiation; 250 W, 395-750 nm) conditions for 15 min, followed by the addition of 1.0 mM cathepsin K substrate Z-GPR-4MβNA and 1.0 mM nitrosalicylaldehyde (precipitating agent), leading to the release of 4MβNA (green fluorescent precipitate indicative of cathepsin K activity). Cells were fixed and imaged. Conditions were as follows: 1) buffer control plus light, 2) 3 (250 nM) plus light, 3) 3 (250 nM), no light, 4) cis-$[Ru(bpy)_2(MeCN)_2](PF_6)_2$ (250 nM, ruthenium control) plus light. Panels are A) green fluorescence of cleaved substrate due to active cathepsin K; B) DIC image; C) blue fluorescence due to DAPI nuclear stain; and D) DIC image merged with green and blue fluorescence demonstrating the intracellular cathepsin K activity.

In order to make a more quantitative assessment of cathepsin K inhibition by VI in osteoclast cells, a larger data set was collected and intensities of green fluorescence were integrated under light and dark conditions. These data, expressed as fluorescence units per cell and represented in FIG. 16, were in good agreement with data against the isolated enzyme, and show generally more potent inhibition under light conditions than dark conditions. Furthermore, similar to data obtained for purified enzyme (FIG. 14), activity was abolished at higher concentrations of VI, even in the dark. Given these results, when VI was used at the optimal concentration of 250 nM, a maximum enhancement in inhibition of about 8 times was observed with light. Our results indicate that intracellular cathepsin K activity can be controlled with light, which indicates that 2, either in its caged or uncaged form, is cell permeable (see below). Future investigations will be directed towards improving dark/light ratios.

FIG. 16. Quantitative analysis of cathepsin K inhibition by cis-$[Ru(bpy)_2(2)_2]Cl_2$ (VI) in live osteoclasts under the dark and light conditions. Osteoclasts were treated with increasing concentrations of VI in the presence of 1 µM CA074 (to eliminate cathepsin B activity) for 30 min at 37° C. Controls were treated with 1 µM CA074 only. Cells were washed and exposed to dark (no irradiation) or light (irradiation; 250 W, 395-750 nm) conditions for 15 minutes, followed by the addition of 1.0 mM cathepsin K substrate Z-GPR-4MβNA and 1.0 mM nitrosalicylaldehyde (precipitating agent), leading to the release of 4βNA (green fluorescent precipitate indicative of cathepsin K activity). Cells were fixed and imaged. A: CTSK activity in osteoclasts in the absence (control) or presence of increasing concentrations of complex VI after exposure to light. Integrated intensity/nuclei values were normalized to controls and expressed as percent activity in the dark. Dose-dependent inhibition of cathepsin K activity is observed with increasing concentrations of complex VI and is completely abolished at 250 nM. B: Cathepsin K activity in osteoclasts treated with 250 nM and 1 µM complex 3 under dark and light conditions. Data are shown as percent activity under control conditions. At 250 nM complex VI completely inhibits cathepsin K activity with light but not dark exposure. At 1 µM concentration, inhibition of cathepsin K is observed at both, light and dark conditions. All data were analyzed using Graph Prizm software and are shown as mean±S.D. * indicates p=0.08;  indicates p=0.02; and * indicates p=0.003; p values <0.05 are considered statistically significant.

Example 8

Determination of Toxicity

In order to gain more insight into the biological behavior of the caged inhibitor, effects of VI and its byproducts on cell viability in BMM cells were determined under light and dark conditions. BMM cells were treated with either VI or cis-$[Ru(bpy)_2(MeCN)_2](PF_6)_2$ as a control (1 nM-100 µM), incubated for 30 min, left in the dark or irradiated with a tungsten halogen lamp for 15 min and then washed, using the same protocol as the confocal microscopy studies shown in FIG. 15. After 24 h viabilities were determined using the MTT assay (FIG. 17). Compounds VI and cis-$[Ru(bpy)_2(MeCN)_2](PF_6)_2$, which both release cis-$[Ru(bpy)_2(H_2O)_2]^{2+}$ upon irradiation, showed no effects on viability within error over the full concentration range, including up to 100 µM, which is 400 times greater than the concentration where complete enzyme knockdown was realized.

FIG. 6. Cytotoxicity of cis-$[Ru(bpy)_2(2)_2]Cl_2$ (3) and the control compound cis-$[Ru(bpy)_2(MeCN)_2](PF_6)_2$ on BMM cells (A-B) and prostate cancer PC3 cells (C-D). Cells were incubated in the presence of VI or cis-$[Ru(bpy)_2(MeCN)_2](PF_6)_2$ (1 nM-100 µM) for 30 min, left in the dark (black) or irradiated (red) with a tungsten halogen lamp (250 W, $\lambda_{irr}$>395 nm, $H_2O$ filter) for 15 min and washed. Cell viability was determined using the MTT assay after 24 h for BMM cells and 72 h for PC3 cells, and is reported relative to control with only buffer added. Error bars represent the standard deviations of triplicate wells, and data are representative of three independent experiments.

Literature data confirm that ruthenium complexes show a wide range of effects on cell viability, with some compounds showing potent toxicity while others are non-toxic. These effects are highly dependent on the nature of ligands bound to ruthenium, and with some compounds treatment for up to 72 h is necessary to observe growth inhibitory effects. Later time points were not examined with BMM cells due to complications in maintaining these cells in culture over long periods of time, with or without VI. However, repeating the treatments and viability measurements in prostate cancer PC3 cells revealed that growth inhibitory effects are also not observed for VI or cis-$[Ru(bpy)_2(MeCN)_2](PF_6)_2$ under light or dark conditions, over the full concentration range (1 nM-100 μM) for time periods up to 72 h. With data across two cell lines taken together, these results strongly suggest that caging nitrile-based inhibitors with Ru(bpy)$_2$ can furnish a powerful method for controlling enzyme inhibition spatially with light, without toxic side effects from ruthenium complexes or byproducts.

Example 9

Preparation of a 5CNU Complex

Materials. The ligand 2,2':6',2"-terpyridine (tpy), (prepared according to the description in Sgambellone et al., *J. Am. Chem. Soc.* 2013, 135 (30), pp 11274-11282), sodium phosphate, gel loading buffer (0.05% (w/v) bromophenol blue, 40% (w/v) sucrose, 0.1 M EDTA (pH=8.0), 0.5% (w/v) sodium lauryl sulfate), Tris base, Tris/HCl, and ethidium bromide were purchased from Sigma and used as received. The 5-cyanouracil (5CNU) reagent was purchased from Alfa Aesar, and pUC 19 plasmid was purchased from Bayou Biolabs and purified using the QIAprep miniprep spin system from Qiagen. Cell culture reagents, SmaI, React 4 buffer reagents, and Sytox Green were purchased from Invitrogen. The removal of SmaI was performed with the QIAquick gel extraction kit from Qiagen. Ru(tpy)Cl$_3$, [Ru (tpy)(CH3CN)3]$^{2+}$ (1), and cis-[Ru(tpy)-(CH$_3$CN)$_2$Cl]$^+$ (2) were prepared by procedures previously reported.

[Ru(tpy)(5CNU)$_3$]Cl$_2$ (3). A sample of Ru(tpy)Cl$_3$ (0.114 mmol, 50 mg) was suspended in 10 mL of ethanol, resulting in a brown mixture to which Ag(CF$_3$SO$_3$) (0.341 mmol, 88 mg) was added. The solution quickly turned purple and was filtered to remove AgCl after which time 5CNU (1.14 mmol, 156 mg) and 2 mL of H$_2$O were added. The mixture was refluxed under N$_2$ for 24 h, and the solvent was removed by evaporation. The crude product was dissolved in 10 mL of boiling H$_2$O, and a 5 mL aliquot of a saturated solution of NH$_4$PF$_6$ was added. The solution was placed in the freezer overnight to aid in precipitation of the product. The [Ru (tpy)(5CNU)$_3$](PF$_6$)$_2$ solid was collected and washed with cold H$_2$O and diethyl ether. The [PF$_6$]$^{-1}$ anion was exchanged for Cl$^-$ using an Amberlite column and eluted with methanol. Anal. Calcd for [Ru(C$_{15}$H$_{11}$N$_3$)(C$_5$H$_3$N$_3$O$_2$)$_3$] Cl$_2$.6.5H$_2$O: C, 39.0%; H, 2.9%; N, 18.2%. found: C, 39.3%; H, 3.3%; N, 18.1%. $^1$H NMR (400 MHz) in D$_2$O δ ppm (splitting, integration): 7.80 (t, 2H) tpy, 7.97 (s, 2H) 5CNU axial, 8.24 (m, 3H) tpy, 8.50 (d, 4H) tpy, 8.69 (s, 1H) 5CNU equatorial, 9.10 (d, 2H) tpy.

A schematic representation (a) of the molecular structures of 1-3 of this example, tpy, and 5CNU, and (b) photorelease of a metal complex able to bind DNA and of the biologically active 5CNU molecule through irradiation with visible light in water, are illustrated in FIG. 18.

Example 10

Photocaging Groups for Nitriles: Ruthenium tri(2-pyridylmethyl)amines

Caging molecules with photolabile protecting groups has revolutionized our ability to interrogate spatial and temporal aspects of biological activity. The caging approach involves bonding biologically active molecules to organic or metal-based protecting groups that are cleaved with light. To date, the most widely used inorganic protecting group for photocaging has been Ru(bpy)$_2$. Pioneering work demonstrated that Ru(bpy)$_2$ can be used to cage neurotransmitters; later examples were applied to anticancer agents by Garner, Turro, and coworkers (*Inorg. Chem.* 2011, 50, 9213), and to enzyme inhibitors by Turro, Kodanko, and coworkers (*J. Am. Chem. Soc.* 2011, 133, 17164). By in large, the development of Ru-based caging groups has focused on planar, chelating heteroaromatic ligands similar to bpy (see Sgambellone et al., *J. Am. Chem. Soc.* 2013, 135, 11274). In this example, we report that ruthenium (II) tri(2-pyridylmethyl) amine, distinct from the established Ru(bpy)$_2$ class, is an effective caging group for nitriles that provides high levels of control over enzyme activity with light.

Two caged nitriles of the general formula [Ru(TPA) (RCN)$_2$](PF$_6$)$_2$ were prepared for this study (Scheme 10.1). Complex 10.1 contains two caged MeCN ligands, whereas complex 10.2 contains two equivalents of the cysteine protease inhibitor Cbz-Leu-NHCH$_2$CN (3), a potent and selective inhibitor of human cathepsin K. Complex 10.1 was prepared as a yellow solid by heating [Ru(TPA)Cl(Me$_2$SO)] Cl in 1:1 H$_2$O:MeCN, followed by precipitation with NH$_4$PF$_6$ (see Whiteoak et al., C. J.; *Inorg. Chem.* 2013, 52, 7000, for additional synthetic techniques). Complex 10.2 was prepared by heating [Ru(TPA)(H$_2$O)$_2$](OTf)$_2$ (*Inorg. Chem.* 2011, 50, 10564) in the presence of 5 equiv of the protease inhibitor 10.3 in EtOH. Concentration, aqueous workup and precipitation as the dihexafluorophosphate salt from 1:1 H$_2$O:MeOH furnished [Ru(TPA)(10.3)$_2$](PF$_6$)$_2$ (10.2) as a pale yellow solid.

Scheme 10.1. Caged nitriles [Ru(TPA)(MeCN)$_2$](PF$_6$)$_2$ (10.1) and [Ru(TPA)(10.3)$_2$](PF$_6$)$_2$(10.2).

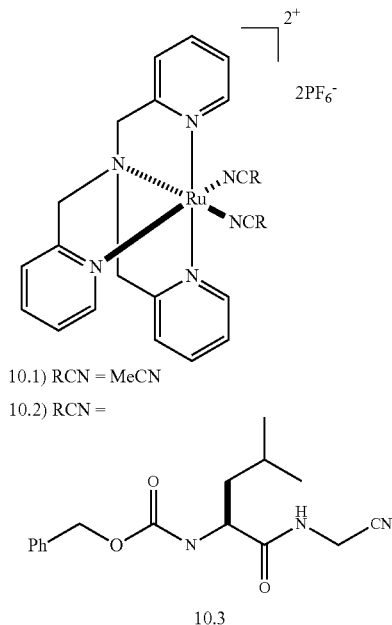

10.1) RCN = MeCN 10.2) RCN =

10.3

Complexes 10.1 and 10.2 were characterized by a suite of methods, including UV-vis, NMR and IR spectroscopies and ESMS. UV-vis spectra for 10.1 and 10.2 are highly consistent between these related complexes, with bands shown at 380 nm (ε=11,200 M$^{-1}$ cm$^{-1}$) and 375 nm (ε=12,000 M$^{-1}$ cm$^{-1}$), respectively. $^1$H NMR spectroscopic analysis of 10.1 indicated the presence of two distinct MeCN ligands, with singlets at 2.88 and 2.47 ppm, consistent with the expected structure with one MeCN ligand trans to the basic nitrogen donor of TPA and one cis. Likewise the NMR spectrum of 10.2 showed two sets of AB doublets assigned to the α-CN methylene unit of ligand 10.3, which were separated by approximately 0.5 ppm. IR spectra for 10.1 and 10.2 showed resonances for $v_{CN}$ at 2276 and 2269 cm$^{-1}$, respectively, consistent with nitrile binding to Ru(II). Mass spectra of 10.1 and 10.2 showed prominent ion clusters with major peaks at m/z 619.1 and 499.2, along with suitable isotopic distributions, which match that expected for the cation [Ru(TPA)(MeCN)$_2$](PF$_6$)$^+$ and dication [Ru(TPA)(10.3)$_2$]$^{2+}$.

Complex 10.1 was characterized further by X-ray crystallography. Diffusion of Et$_2$O into a solution of 10.1 in MeCN furnished small yellow blocks of 10.1 suitable for X-ray crystallographic analysis. Select data for 10.1 are described in the X-ray Crystallographic Analysis section below. Ru1-N5 and Ru1-N6 bond lengths are identical within error. Structural parameters for 10.1 are similar to that reported recently for [Ru(TPA)(MeCN)$_2$](SbF$_6$)$_2$. In the ORTEP diagram of the dication [Ru(TPA)(MeCN)$_2$]$^{2+}$, thermal ellipsoids were shown at 50% probability. Selected bond lengths (Å) and angles (deg): Ru—N1, 2.070(4); Ru—N2, 2.054(5); Ru—N3, 2.067(4); Ru—N1r1, 2.054(5); Ru—N5, 2.036(5); Ru—N6, 2.034(5); N5-Ru—N6, 88.9(2).

Complexes 10.1 and 10.2 show fast release of a single nitrile upon irradiation with 365 nm light. Decreases for absorbances at 380 and 375 nm, tentatively assigned as metal-to-ligand charge transfer (MLCT) bands, are observed within 15 minutes of irradiation with a low power (8 W) light source in acetone:H$_2$O solutions (10:1), with concomitant appearance of new bands (FIG. 19). When the same photochemical reactions are followed in deuterated solvents by $^1$H NMR spectroscopy, data indicate that only one of two possible nitriles are released from Ru(II). Intensity of downfield resonances assigned to methyl and methylene protons α to nitrile of 10.1 and 10.2 decrease with increases in free MeCN and free ligand 10.3. Released nitriles are assigned as cis to the basic nitrogen of the TPA ligand, based on $^1$H COSY and NOESY data. This structural assignment is further supported by the fact that downfield shifts for resonances of α-CN protons in 10.1 and 10.2 would be expected, due to shielding by two cis pyridine rings of the TPA ligand, whose π-systems are orthogonal to the Ru—N vector of the nitrile that is released upon photolysis.

Complex 10.2 acts as a potent, photoactivated inhibitor of human cathepsin K. IC$_{50}$ values were determined for 10.2 and 10.3 under dark conditions, and upon irradiation with 365 nm light (FIG. 20). Enzyme inhibition for 10.2 was enhanced by a factor of 89 upon exposure to light, with IC$_{50}$ values of 63 nM and 5.6 μM, for light and dark conditions, respectively. In contrast, inhibition by the free inhibitor 3 was identical within error under light and dark conditions, confirming that irradiation has no effect on inhibition under the assay conditions. Control experiments with 10.1 showed no inhibition of cathepsin K under light and dark conditions at 500 μM, the highest concentration surveyed, confirming that neither the Ru complex, nor its photochemical byproduct, are responsible for the inhibition observed for 10.2 upon irradiation. Taken together, these data confirm that Ru(TPA) is an effective caging group.

FIG. 20 shows the IC$_{50}$ curves for Ru-caged inhibitor 10.2 ((A), with irradiation, and (B), without irradiation) and uncaged inhibitor 10.3 ((C), with irradiation, and (D), without irradiation) against human cathepsin K. Enzyme activity was determined with the fluorogenic substrate Z-Gly-Pro-Arg-AMC, and is expressed as a percentage, with 100% equal to activity in absence of inhibitor. Individual data points are the average of three wells, and error bars are standard deviations. Data are representative of three independent experiments. Conditions: 0.1 M acetate buffer, pH 5.5, 1% DMSO, [cathepsin K]=2 nM, [Z-Gly-Pro-Arg-AMC]=20 mM, DTT=8 mM, 15 minutes irradiation with a 365 nm light source (8 W).

In conclusion, this example establishes Ru(TPA) as a new caging group for bioactive nitriles. Efficient photoactivated enzyme inhibition against human cathepsin K was demonstrated with the caged inhibitor complex 10.2.

Experimental procedure for preparation of 10.1 and 10.2, characterization data for 10.1 and 10.2, experimental procedures for photochemical and enzyme inhibition studies are as follows.

General Considerations. Reagents were purchased from commercial suppliers and used as received. NMR spectra were recorded on a Varian FT-NMR Mercury-400 MHz Spectrometer. Mass spectra were recorded on a Time-of-Flight Micromass LCT Premier XE Spectrometer. IR spectra were recorded on a Nicolet FT-IR spectrophotometer (KBr pellet). UV-vis spectra were recorded on a Varian Cary 50 spectrophotometer. All reactions were performed under ambient atmosphere unless otherwise noted. Anaerobic reactions were performed by purging the reaction solutions with Ar or N$_2$. Bpy=2,2'-bipyridine; TPA=tri(2-methylpyridyl)amine.

Experimental Procedures.

Synthesis of [Ru(TPA)(CH$_3$CN)$_2$](PF$_6$)$_2$ (10.1). [Ru(TPA)(DMSO)Cl]Cl (200.0 mg, 0.370 mmol) as a 2:1 mixture of stereoisomers, was dissolved in a 1:1 mixture of H$_2$0 and CH$_3$CN (20 mL) under argon atmosphere and the resulting solution was refluxed for 2 hours under inert atmosphere. Ice cold water (20 mL) was added to the reaction mixture followed by a saturated solution of aqueous NH$_4$PF$_6$ (5 mL), resulting in a pale yellow precipitate that was isolated by filtration, washed with ice-cold H$_2$O and dried under reduced pressure to get the title complex as a yellow solid (136 mg, 48%). Crystals suitable for X-ray crystallographic analysis were obtained by diffusing Et$_2$O into a solution of 10.1 in MeCN: mp=190° C. (decomp); $^1$H NMR (400 MHz C$_3$D$_6$O:D$_2$O-9:1) δ 9.18 (d, 1H, J=5.9 Hz), 8.83 (d, 2H, J=5.9 Hz), 7.85 (t, 2H, J=7.8 Hz), 7.68-7.56 (m, 3H), 7.41 (t, 2H, J=6.8 Hz), 7.25 (t, 1H, J=6.8 Hz), 7.18 (d, 1H, J=7.8 Hz), 5.25 (d, 2H, J=15.6 Hz), 5.15 (d, 2H, J=15.6 Hz), 4.86 (s, 2H), 2.88 (s, 3H), 2.47 (s, 3H); IR (KBr) ν$_{max}$ (cm$^{-1}$) 3666, 3592, 3418, 3119, 2935, 2856, 2276, 1729, 1609, 1481, 1461, 1448, 1311, 1289, 1160, 992, 838, 767, 739. ESMS calcd for C$_{22}$H$_{24}$F$_6$N$_6$PRu (M$^{+1}$) 619.075, found 619.073; UV-vis λ$_{max}$=380 (ε=11200 M$^{-1}$ cm$^{-1}$); Anal. Calcd for C$_{22}$H$_{24}$F$_{12}$N$_6$P$_2$Ru: C, 34.61; H, 3.17; N, 11.01. Found: C, 34.70; H, 3.20; N, 10.82.

Synthesis of [Ru(TPA)(RCN)$_2$](PF$_6$)$_2$ (10.2). A solution of [Ru(TPA)(H$_2$O)$_2$](CF$_3$SO$_3$)$_2$ (540 mg, 0.72 mmol) and dry EtOH (40 mL) was deoxygenated by bubbling Ar through a submerged needle for 10 minutes. Cbz-Leu-NHCH$_2$CN (1.09 g, 3.6 mmol) was added and the reaction mixture was refluxed for 24 hours at 80° C. under an Ar atmosphere. The reaction mixture was cooled to room temperature and concentrated under reduced pressure. The green oil was extracted with Et$_2$O (3×20 mL) to get a dark green solid, which was dissolved in minimum amount of CH$_2$Cl$_2$ and washed with water (3×30 mL). The organic layer was dried (NaSO$_4$) and concentrated under reduced pressure to get a dark green solid (501 mg). The dark green solid was dissolved in MeOH (10 mL) and H$_2$O (10 mL) was added. The insoluble green oil was removed by centrifugation. A saturated solution aqueous solution of NH$_4$PF$_6$ (2 mL) was added to the clear pale green supernatant solution, resulting in formation of a precipitate that was isolated by filtration, washed with water (3×20 mL) and dried under reduced pressure to get the title compound as a pale yellow solid in analytically pure form (290 mg, 53%): mp=210° C. (decomp); $^1$H NMR (400 MHz C$_3$D$_6$O) δ 9.19 (d, 1H, J=5.6 Hz), 8.85 (d, 1H, J=6.1 Hz), 8.84 (d, 1H, J=6.1 Hz), 8.50 (t, 1H, J=5.1 Hz), 8.16 (t, 1H, J=4.7 Hz), 7.92-7.87 (m, 2H), 7.71-7.62 (m, 3H), 7.43-7.22 (m, 14H), 6.96 (d, 1H, J=7.3 Hz), 6.79 (d, 1H, J=7.1 Hz), 5.32 (d, 1H, J=15.7 Hz), 5.31 (d, 1H, J=15.7 Hz), 5.20-5.14 (m, 3H), 5.07-4.96 (m, 4H), 4.90-4.88 (m, 2H), 4.81 (d, 1H, J=12.7 Hz), 4.57-4.45 (m, 2H), 4.36-4.32 (m, 1H), 4.16-4.11 (m, 1H), 1.86-1.65 (m, 3H), 1.61-1.42 (m, 3H), 0.97-0.84 (m, 12H); IR (KBr) $\nu_{max}$ (cm$^{-1}$) 3417, 3319, 2959, 2873, 2265, 1717, 1684, 1608, 1519, 1451, 1406, 1340, 1312, 1254, 1160, 1121, 1044, 844, 769, 740, 699; ESMS calcd for $C_{50}H_{60}N_{10}O_6Ru$ (M$^{+2}$) 499.18, found 499.19; UV-vis $\lambda_{max}$=375 ($\epsilon$=12000 M$^{-1}$ cm$^{-1}$); Anal. Calcd for $C_{50}H_{61}F_{12}N_{10}O_{6.5}P_2Ru$ (2.0.5 H$_2$O): C, 46.30; H, 4.74; N, 10.80. Found: C, 46.21; H, 4.79; N, 10.78.

X-ray Crystallographic Analysis. A clear light yellow Coxcomb-like specimen of $C_{46}H_{51}F_{36}N_{17}P_6Ru_2$, approximate dimensions 0.220 mm×0.230 mm×0.480 mm, was used for the X-ray crystallographic analysis. The X-ray intensity data were measured.

A total of 3399 frames were collected. The total exposure time was 56.65 hours. The frames were integrated with the Bruker SAINT software package using a narrow-frame algorithm. The integration of the data using a triclinic unit cell yielded a total of 67668 reflections to a maximum θ angle of 27.45° (0.77 Å resolution), of which 13752 were independent (average redundancy 4.921, completeness=93.5%, R$_{int}$=3.63%, R$_{sig}$=5.00%) and 10647 (77.42%) were greater than 2σ(F$^2$). The final cell constants of a=12.1132(7) Å, b=12.2926(8) Å, c=21.8487(13) Å, α=94.436(3)°, β=97.004(3)°, γ=91.322(3)°, volume=3217.6 (3) Å$^3$, are based upon the refinement of the XYZ-centroids of 9865 reflections above 20 σ(I) with 4.67°<2θ<54.57°. Data were corrected for absorption effects using the multi-scan method (SADABS). The ratio of minimum to maximum apparent transmission was 0.918. The calculated minimum and maximum transmission coefficients (based on crystal size) are 0.7056 and 0.8478.

The structure was solved and refined using the Bruker SHELXTL Software Package, using the space group P -1, with Z=2 for the formula unit, $C_{46}H_{51}F_{36}N_{17}P_6Ru_2$. The final anisotropic full-matrix least-squares refinement on F$^2$ with 808 variables converged at R1=6.58%, for the observed data and wR2=21.82% for all data. The goodness-of-fit was 1.548. The largest peak in the final difference electron density synthesis was 2.311 e$^-$/Å$^3$ and the largest hole was −1.500 e$^-$/Å$^3$ with an RMS deviation of 0.149 e$^-$/Å$^3$. On the basis of the final model, the calculated density was 1.976 g/cm$^3$ and F(000), 1896 e$^-$.

Example 11

Photocaging Groups for Nitriles: Ruthenium 2-p-tolylpyridinecarboxaldimine

A new ligand for the complexes described herein includes the bidentate ligand 2-p-tolylpyridinecarboxaldimine (PTPI). As illustrated by FIGS. 21-23, the ligands depart from ruthenium at lower energy than many known ligands. PTPI can be prepared as illustrated below in Scheme 11.1.

Scheme 11.1. Preparation of PTPI and PTPI Ruthenium complexes.

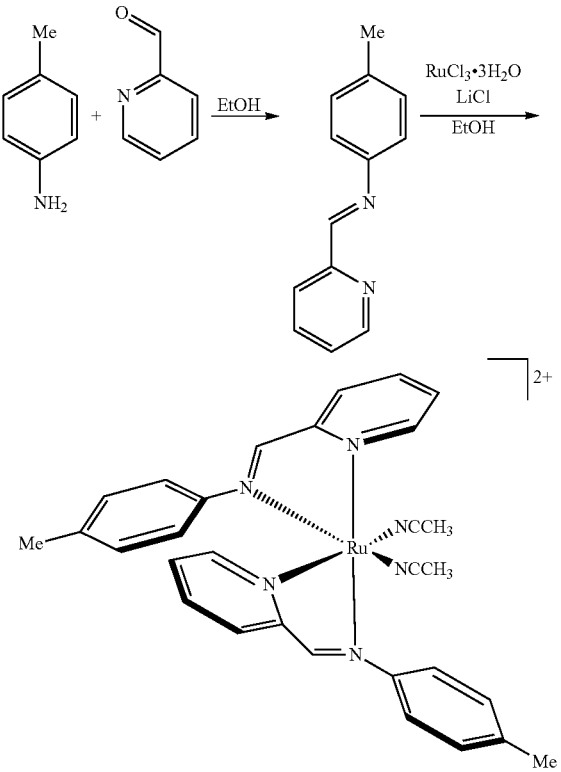

Ruthenium complexes such that the complex of Scheme 11.1 can be used to prepare caged nitrile compounds, including caged protease inhibitors. For example, PTPI ligands can be used alone, or in combination with other ligands described herein to form caged compounds where one or more nitrile ligands (e.g., one, two, or three nitrile ligands) are coordinated to the ruthenium metal. The nitrile ligands, such as protease inhibitors, can have the formula R—CN, as described above.

Example 12

Selective Photoinduced Ligand Exchange in a New Tris-Heteroleptic Ru(II) Complex The complex cis-[Ru(biq)(phen)(CH$_3$CN)$_2$]$^{2+}$ (12.1, biq=2,2'-biquinoline, phen=1,10-phenathroline) displays selective photosubstitution of only one CH$_3$CN ligand with a solvent molecule upon irradiation with low energy light ($\lambda_{irr}$≥550 nm), whereas both ligands exchange with $\lambda_{irr}$≥420 nm. In contrast, [Ru(phen)$_2$(CH$_3$CN)$_2$]$^{2+}$ (12.2) and [Ru(biq)(CH$_3$CN)$_2$]$^{2+}$ (12.3) exchange both CH$_3$CN ligands with similar rates upon irradiation with a broad range of wavelengths. The photolysis of 12.1 in the presence of pyridine, py, results in the formation of the intermediate cis-[Ru(biq)(phen)(py)(MeCN)]$^{2+}$, which was isolated and characterized by X-ray crystallography, revealing that the CH$_3$CN positioned trans to the phen ligand is more photolabile than that positioned trans to the biq ligand when irradiated with low energy light. These results are explained using the calculated stabilities of the two possible products, together with the molecular orbitals involved in the lowest energy excited state.

Understanding the photochemistry of transition metal complexes is essential to the development of areas that include solar energy conversion, photocatalysis, and photochemotherapy (PCT). These processes are initiated by the absorption of a photon by the molecule, placing it in an excited state that is able to undergo reactions that are not accessible from the ground state. Ruthenium(II) complexes are of particular interest due to their success as sensitizers in dye sensitized solar cells, as well as their potential as PCT agents. In addition, many of these Ru(II) complexes have the ability to undergo excited state ligand substitution.

The broadly accepted model for the mechanism of photoinduced ligand exchange in complexes with lowest-energy $^3$MLCT (metal-to-ligand charge transfer) relies on the thermal population of the reactive $^3$LF (ligand field) dd state(s) from the lower-lying $^3$MLCT state(s). The population of the $^3$LF state(s) places electron density on the $e_g$-type orbitals with Ru-Lσ* character, thus resulting in ligand dissociation. Accordingly, the energy gap between the $^3$MLCT and the $^3$LF states has been shown to have a pronounced effect on the quantum yield of ligand exchange when the low-lying MLCT state is excited selectively. Moreover, direct excitation of the LF state(s) with higher energy light results in a significant increase in the photoreactivity.

The exploration of the photochemistry of Ru(II) complexes possessing monodentate $CH_3CN$ ligands such as $[Ru(bpy)(CH_3CN)_4]^{2+}$ (bpy=2,2'-bipyridine) and $[Ru(bpy)_2(CH_3CN)_2]^{2+}$ revealed efficient ligand exchange of the $CH_3CN$ ligand with a coordinating solvent or with excess halide upon irradiation with visible light. It was shown that ligand exchange occurred in a stepwise manner and that the quantum yield for the exchange of the second $CH_3CN$ ligand is ~2-fold lower than that of the first $CH_3CN$ ligand. Moreover in $[Ru(bpy)(CH_3CN)_4]^{2+}$, which possesses four potential sites for exchange, only the axial $CH_3CN$ ligands undergo stepwise substitution with water upon irradiation. This reactivity provides an important synthetic tool for the preparation of new trans tris-heteroleptic Ru(II) complexes, as well as PCT agents with photolabile ligands that can function in hypoxic environments without the need for oxygen.

In the present work, the asymmetric complex $[Ru(biq)(phen)(CH_3CN)_2]^{2+}$ (1, Scheme 12.1) (biq=2,2'-biquinoline, phen=1,10-phenathroline) was synthesized and characterized, and its photochemical properties were investigated. The results were compared to those of the symmetric complexes $[Ru(phen)_2(CH_3CN)_2]^{2+}$ (2, Scheme 12.1) and $[Ru(biq)(CH_3CN)_2]^{2+}$ (3, Scheme 12.1). Each of the complexes 12.1-12.3 possesses two potentially photolabile $CH_3CN$ ligands, however, unlike 12.2 and 12.3, one $CH_3CN$ ligand of 12.1 is preferentially substituted upon irradiation. The monosubstituted intermediate generated following photolysis in pyridine was isolated and characterized to ascertain which $CH_3CN$ ligand was exchanging. The work described in this example provides an understanding of photoinduced ligand exchange, which can be applied to other systems described herein. For example, nitrile-based enzyme inhibitors can be complexed to the ruthenium complexes described herein in place of acetonitrile and used for the therapeutic treatment of the conditions described above.

Scheme 12.1. Schematic representation of the molecular structures of 12.1-12.3.

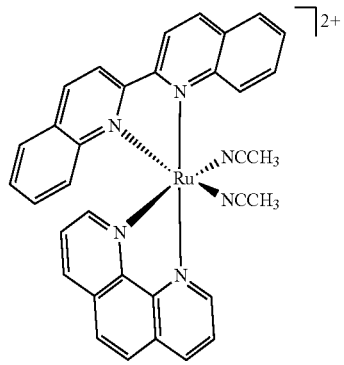

12.1

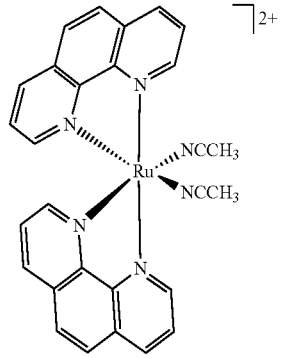

12.2

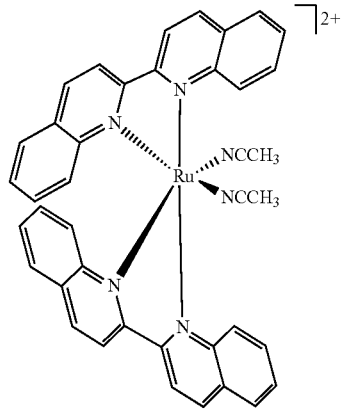

12.3

Experimental Section

Materials. $RuCl_3 \cdot 3H_2O$ and 2,2'-biquinoline (biq) were purchased from CP Labs and Acros Organic, respectively, and were used without further purification. Ascorbic acid, 1,10'-phenanthroline (phen), potassium hexafluorophosphate, and ammonium hexafluorophosphate were purchased from Sigma Aldrich and used as received. All solvents used were purchased from commercial sources and used without further purification unless otherwise specified. The complexes $Ru(phen)Cl_4$, $[Ru(phen)(CH_3CN)_4](PF_6)_2$, and $Ru(phen)_2Cl_2$ were prepared according to literature procedures.

Instrumentation. The $^1$H NMR spectra of all complexes were recorded using a Bruker 400 MHz DPX ultrashield system. Electronic absorption spectroscopy was carried out using a Hewlett Packard 8453 diode array spectrometer, emission spectra were obtained on a Horiba Fluormax-4 spectrometer, and electrochemical studies were performed on a BAS CV-50 W voltammetric analyzer. Photolysis and quantum yield experiments were carried out using a 150 W Xe short arc lamp (USHIO) in a Milliarc lamp housing unit (PTI) powered by a LPS-220 power supply (PTI) equipped with a LPS-221 igniter (PTI). The desired wavelength range was attained using bandpass filters (Thorlabs, fwhm~10 nm) or 3 mm thick (2 mm for 610 nm) long-pass filters (CVI Melles Griot).

[Ru(biq)(phen)(CH$_3$CN)$_2$](PF$_6$)$_2$ (12.1). [Ru(phen)(CH$_3$CN)$_4$](PF$_6$)$_2$ (0.040 mg, 0.0544 mmol) and 2,2'-biquinoline (0.014 mg, 0.0542 mmol) were dissolved in 6 mL of DMF:CH$_3$CN (5:1). The yellow solution was stirred and degassed for 5 minutes with N$_2$, and was then refluxed for 15 hours during which time a gradual color change from yellow to orange, then to light red was observed. The reddish orange solid was precipitated by the addition of 100 mL of H$_2$O and was filtered on a glass fit by vacuum filtration. The solid was dissolved in 20 mL of a CH$_3$CN:H$_2$O mixture (50:50) and heated under reflux for 4 hours, and 5 mL of a concentrated solution of NH$_4$PF$_6$ was added to the solution while still hot. The mixture was slowly cooled to room temperature then placed in an ice bath. A reddish orange solid precipitated and was filtered on a glass frit by vacuum filtration (0.015 mg, 31% yield). $^1$H NMR (400 MHz, (CD$_3$)$_2$CO) δ 10.36 (dd, 1H, $^3$J=5.2 Hz, $^4$J=1.2 Hz) 9.25 (d, 1H, $^3$J=8.9 Hz), 9.08 (m, 2H), 8.96 (dd, 1H, $^3$J=8.2 Hz, $^4$J=1.2 Hz), 8.79 (d, 1H, $^3$J=8.8 Hz), 8.57 (m, 2H), 8.42 (m, 2H), 8.2 (m, 3H), 8.03 (t, 1H, $^3$J=7.4 Hz), 7.87 Hz (m, 3H), 7.73 (m, 1H), 7.57 (t, 1H, $^3$J=3.5 Hz), 7.34 (t, 1H, $^3$J=4.2 Hz) 2.71 (s, 3H), 2.30 (s, 3H). Elem. anal. calcd. for [Ru(biq)(phen)(CH$_3$CN)$_2$](PF$_6$)$_2$.(C$_5$H$_5$)$_2$O.2 H$_2$O: C, 48.4%; N, 9.34%; H, 3.70%. Found: C, 48.10%; N, 6.62%; H, 4.25%.

[Ru(phen)$_2$(CH$_3$CN)$_2$](PF$_6$)$_2$ (12.2). Ru(phen)$_2$Cl$_2$ (0.055 g, 0.10 mmol) was dissolved in 20 mL of a mixture of CH$_3$CN and H$_2$O (50:50, v:v) and was refluxed for 4 hours. The solution was slowly cooled to room temperature and the solvent was evaporated to dryness by blowing with air. The remaining yellow solid was dissolved in 15 mL of H$_2$O washed with 5 aliquots of 20 mL CH$_2$Cl$_2$ until the organic layer was clear. CH$_3$CN (10 mL) was added to the aqueous layer and the mixture was refluxed for 1 hour. A saturated solution of NH$_4$PF$_6$ in water (5 mL) was added to the solution while hot, the mixture was allowed to cool slowly to room temperature, and was then placed in an ice bath. A yellow solid precipitated and the powder was collected by vacuum filtrations and washed with 20 mL of diethyl ether (0.053 mg, 62% yield). $^1$H NMR (400 MHz, (CD$_3$)$_2$CO) δ 10.05 (dd, 2H, $^3$J=5.3 Hz, $^4$J=1.2 Hz), 9.05 (dd, 2H, $^3$J=8.3 Hz, $^4$J=1.3 Hz), 8.64 (dd, 2H, $^3$J=7.1 Hz, $^4$J=1.4 Hz), 8.46 (d, 2H, $^3$J=9.1 Hz), 8.37 (m, 2H) 8.32 (d, 2H, $^3$J=9.0 Hz), 8.09 (dd, 2H, $^3$J=5.3 Hz, $^4$J=1.2 Hz) 2.45 (s, 6H). Elem. anal. calcd. for [Ru(phen)$_2$(CH$_3$CN)$_2$](PF$_6$)$_2$: C, 40.3%; N, 10.1%; H, 2.66%. Found: C, 40.3%; N, 9.96%; H, 2.74%.

Ru(biq)$_2$Cl$_2$. Ru(biq)$_2$Cl$_2$ was prepared using a modification of the synthesis reported by Kubow et. al. RuCl$_3$.H$_2$O (0.18 g, 0.67 mmol), 2,2'-biquinoline (0.37 g, 1.5 mmol), and LiCl (0.087 g, 2.1 mmol) were dissolved in 7 mL of N,N-dimethylformamide. The solution was stirred until all solids dissolved, was degassed with N$_2$ for 5 min, and was then refluxed for 6 hours turning a dark green color. The reaction mixture was slowly cooled to room temperature and pipetted dropwise into 500 mL of stirring H$_2$O, forming a green/blue precipitate that was collected by vacuum filtration. The solid was dissolved in CH$_2$Cl$_2$ forming a dark green solution, and then filtered to get rid of any remaining solid that did not dissolve. The green filtrate was washed 5 times with 20 mL of H$_2$O and then evaporated to a minimal amount of CH$_2$Cl$_2$. An excess of diethyl ether was added to the green CH$_2$Cl$_2$ solution, resulting in the formation of a green precipitate that was collected by vacuum filtration (0.22 g, 48% yield).

[Ru(biq)$_2$(CH$_3$CN)$_2$](PF$_6$)$_2$ (12.3). A procedure analogous to that for 2 was followed but using Ru(biq)$_2$Cl$_2$ (0.055 g, 0.080 mmol) as the starting material, which resulted in the isolation of a maroon powder (0.043 g, 54% yield). $^1$H NMR (400 MHz, (CD$_3$)$_2$CO) δ 8.75 (d, 2H $^3$J=8.7 Hz), 8.42 (d, 2H, $^3$J=8.2 Hz), 8.34 (d, 2H, $^3$J=8.1 Hz), 8.20 (m, 4H), 8.01 (m, 4H), 7.92 (d, 2H, $^3$J=8.0 Hz), 7.46 (t, 2H, 7.1 Hz), 6.80 (m, 4H), 2.46 (s, 6H). Elem. anal. calcd. for [Ru(biq)$_2$(CH$_3$CN)$_2$](PF$_6$)$_2$.C$_2$H$_6$O: C, 48.7%; N, 8.52%; H, 3.07%. Found: C, 48.9%; N, 8.15%; H, 3.52%.

Methods. $^1$H NMR spectroscopy was performed in (CD$_3$)$_2$CO (acetone-d$_6$), CD$_3$CN, or C$_5$D$_5$N (py-d$_5$) and all resonances were referenced to the residual protonated solvent peak. In the photolysis experiments monitored by $^1$H NMR spectroscopy in CD$_3$CN or py-d$_5$, the relative intensities of the peaks were integrated relative to an internal standard of benzene (25 µL). The chloride salt of each complex was used for experiments performed in H$_2$O, which were obtained using an ion exchange column. The stationery phase was composed of Amberlite IRA-410 ion exchange resin prepared by soaking in a 1 M HCl at 50° C. for 3 days and methanol was used as the eluent. Emission was measured at both room temperature and 77K in CH$_3$CN in a 1×1 cm quartz cuvettes using an excitation wavelength corresponding to the maximum of the MLCT absorption for each complex. Cyclic voltammetry experiments were performed in a three-electrode cell with a Pt working electrode, a Pt wire auxiliary electrode, and a saturated Ag/AgCl reference electrode. The samples were dissolved in distilled CH$_3$CN containing 0.1 M tetrabutylammonium hexafluorophosphate as the supporting electrolyte, and bubbled with N$_2$ for 10 minutes prior each measurement. The cyclic voltammetry data was recorded at a scan rate of 100 mV/s, and ferrocene was added to each sample after the measurement as an internal standard (+0.40 V vs SCE in CH$_3$CN). Elemental Analysis was performed by Atlantic Microlab Inc.

The quantum yields (Φ) for photoinduced ligand exchange of the first CH$_3$CN in H$_2$O were measured for complexes 12.1 and 12.3 with 500 nm and 550 nm irradiation wavelengths using the appropriate bandpass filters. The moles of complex reacted was quantitated using electronic absorption spectroscopy by monitoring the decrease in MLCT absorption maximum of each complex as a function of irradiation time (moles reacted/s) at early irradiation times, and Reinecke's salt was used as an actinometer to determine the intensity (Einstein/s) of the Xe arc lamp at the corresponding wavelengths. The Φ for the photoinduced ligand exchange of the second CH$_3$CN ligand was measured for 12.1 using 400 nm and 550 nm irradiation wavelengths using the appropriate bandpass filters monitoring the decrease in the MLCT absorption peak of the mono-aqua intermediate, 12.4.

Crystals suitable for single X-ray diffraction were grown for 12.1 by slow vapor diffusion. A ~2 mg sample was dissolved in a mixture of CH$_3$CN, THF, and acetone (0.25 mL, 0.10 mL, and 0.25 mL, respectively) in a small vial and inserted into a larger vial partially filled with ether, which was sealed and placed in the freezer resulting in red rods over a period of 2 weeks.

Single crystals of both 12.1 and the intermediate generated following irradiation of 12.1 in 50:50, v:v CH$_3$CN: pyridine (py) with visible light, [Ru(biq)(phen)(CH$_3$CN)(py)]$^{2+}$ (12.6) were isolated as block-like dark red crystals and handled under a pool of fluorinated oil. Examination of the diffraction pattern was done on a Nonius Kappa CCD diffractometer with Mo Kα radiation. All work was done at 150 K using an Oxford Cryosystems Cryostream Cooler.

Data integration was done with Denzo, and scaling and merging of the data was done with Scalepack. The structures were solved by the direct methods program in SHELXS-97. Full-matrix least-squares refinements based on $F^2$ were performed in SHELXL-97, as incorporated in the WinGX package. For each methyl group, the hydrogen atoms were added at calculated positions using a riding model with U(H)=1.5Ueq (bonded carbon atom). The rest of the hydrogen atoms were included in the model at calculated positions using a riding model with U(H)=1.2Ueq (bonded atom). Neutral atom scattering factors were used and include terms for anomalous dispersion. Compound 12.6 was disordered in several locations, and was composed of a mixture of compounds.

Calculations were performed with density functional theory (DFT) using the Gaussian 09 program. The B3LYP functional along with the 6-31G* basis set for H, C, and N and the SDD energy consistent pseudopotentials were used for Ru. Methyl groups were replaced with hydrogen atoms on the acetonitrile groups to decrease the calculation time. Optimization of full geometries was carried out with the respective programs and orbital analysis was performed in Gaussview. Following optimization of the molecular structures, frequency analysis was performed to ensure the existence of local minima on the potential energy surfaces. Electronic absorption singlet to singlet transitions were calculated using time-dependent DFT (TD-DFT) methods with the polarizable continuum model (PCM) that mimicked the solvation effect of $CH_3CN$ in Gaussian 09. Singlet-triplet transitions were also calculated to generate difference density plots of the lowest energy triplet excited states.

Results Discussion

Electronic Absorption, Emission, and Electrochemistry. The $^1$MLCT absorption maxima of 12.1, 12.2, and 12.3 in $CH_3CN$ are observed at 497 nm ($\epsilon$=7,800 $M^{-1}$ $cm^{-1}$), 420 nm ($\epsilon$=10,200 $M^{-1}$ $cm^{-1}$), and 535 nm ($\epsilon$=7,900 $M^{-1}$ $cm^{-1}$), respectively. As expected, the sequential replacement of the phen ligands in 12.2 for biq in 12.1 and 12.3 results in a stepwise red shift in the lowest energy MLCT absorption maximum. A similar trend is observed in the polypyridyl complexes $[Ru(phen)_3]^{2+}$, $[Ru(phen)_2(biq)]^{2+}$, and $[Ru(phen)(biq)_2]^{2+}$ with $^1$MLCT maxima at 450 nm, 523 nm, and 551 nm in methanol, respectively. In addition to the Ru→biq $^1$MLCT absorption in 12.1, a shoulder at ~410 nm arising from the Ru→phen $^1$MLCT transition in the complex is apparent, which is at a position similar to that of 12.2. Very weak emission is observed for 12.1 ($\lambda_{exc}$=500 nm) and 12.3 ($\lambda_{exc}$=535 nm) at room temperature and 12.2 is not emissive ($\lambda_{exc}$=420 nm), however, relatively strong luminescence was detected for all three complexes at 77 K, as is typical for such complexes.

Cyclic voltammetry reveals quasi-reversible oxidation events, $E_{1/2}(Ru^{3+/2+})$, at +1.51 V, +1.45 V, and +1.55 V vs SCE for 12.1, 12.2, and 12.3, respectively, in $CH_3CN$. The similarity among the three potentials points at a metal-centered process, as is typical of Ru(II) polypyridyl complexes. Quasi-reversible reduction waves in 12.2 are observed at −1.39 V and −1.55 V vs. SCE, at potentials similar to the ligand-centered reduction processes reported previously for the complex. As expected, these waves are shifted to −0.77 V and −1.04 V vs SCE in 12.3, since the electrons are localized on the biq ligands with a more extend π-system as compared to phen. The reduction potentials measured for 12.3 are comparable to those published for related Ru(II) complexes containing the same ligand, including $[Ru(biq)(bpy)_2](PF_6)_2$ and $[Ru(biq)_2(bpy)](PF_6)_2$ with $E_{1/2}(Ru^{2+/+})$=−0.97 V and −089 V vs SCE, respectively. In the asymmetric complex 12.1, the two reversible reduction waves are observed at −0.91 V and −1.45 V vs. SSCE, assigned to reduction of the biq ligand at the more positive potential, followed by reduction the phen ligand.

Photochemistry. The photoreactivity of 12.1-12.3 was evaluated by monitoring the changes to the electronic absorption and $^1$H NMR spectra as a function of irradiation time. All three complexes possess photolabile $CH_3CN$ ligands with photochemistry that can be accessed with $\lambda_{irr}$≥550 nm for 12.1, $\lambda_{irr}$≥455 nm for 12.2, and $\lambda_{irr}$≥610 nm for 12.3. Complexes 12.1-12.3 are inert to ligand substitution in the dark at room temperature under similar experimental conditions. For the symmetrical complexes 12.2 and 12.3, one resonance is observed in $CD_3CN$ corresponding to the methyl protons of both bound acetonitrile ligands at 2.22 ppm and 2.28 ppm, respectively. During the photolysis of 12.2 in $CD_3CN$ with $\lambda_{irr}$≥455 nm, the resonance at 2.22 ppm decreases with increasing irradiation time, while a peak at 1.96 ppm corresponding to free $CH_3CN$ in $CD_3CN$ increases in intensity at the same rate. The photolysis of 12.3 in $CD_3CN$ with $\lambda_{irr}$≥610 nm yields similar results with the decrease of the peak at 2.28 ppm with the concomitant increase of the free $CH_3CN$ resonance at 1.96 ppm. The intensity of the peak corresponding to free $CH_3CN$ at 1.96 ppm integrates to two ligands at the end of the photolysis for both 12.2 and 12.3 in $CD_3CN$, indicative that that both $CH_3CN$ ligands in 12.2 and 12.3 are exchanged. It should be noted that because of the electronic equivalence of $CH_3CN$ and $CD_3CN$, the $^1$H NMR resonance of bound $CH_3CN$ ligands does not shift from those in 12.2 and 12.3 to that in the corresponding mono-substituted intermediate. Moreover, no shifts are observed in the aromatic region as the reaction progresses.

The changes to the $^1$H NMR spectrum of 12.1 upon irradiation in $CD_3CN$ using benzene as an internal integration standard are shown in FIG. 24 ($\lambda_{irr}$≥455 nm). The $CH_3CN$ ligands of 12.1 are inequivalent, resulting in two resonances of equal integration at 2.53 ppm and 2.12 ppm, labeled $CH_3CN^1$ and $CH_3CN^2$ in Scheme 12.2, respectively. FIG. 24 shows that the resonance corresponding to $CH_3CN^2$ decreases at a faster rate than that of $CH_3CN^1$ upon irradiation in $CD_3CN$; the former disappears within 20 min of photolysis while a significant (~75%) of the latter is still present after 60 min of irradiation. Because the disappearance of the peaks corresponding to bound $CH_3CN$ ligands are concomitant with the increase of that associated with free $CH_3CN$ at 1.96 ppm, the observed reactivity can be ascribed to the photoinduced ligand exchange with the $CD_3CN$ solvent. The differences in photoinduced ligand exchange among 12.1-12.3 show that the substitution of the two $CH_3CN$ ligands in 12.2 and 12.3 is complete in 5-60 minutes. In contrast, the photosubstitution of one $CH_3CN$ ligand for $CD_3CN$ in 12.1 is accomplished in ≤5 minutes, but the second $CH_3CN$ ligand does not exchange up to 180 minutes of irradiation.

Scheme 12.2. Molecular structure of 12.1 with labeled CH₃CN ligands.

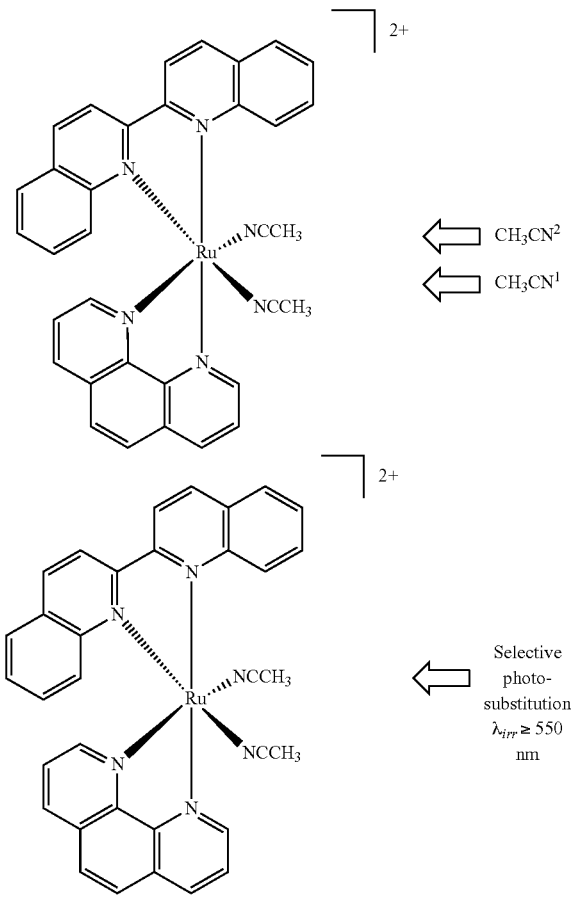

The photolysis of 12.1 in H$_2$O ($\lambda_{irr} \geq 550$ nm) results in a decrease of the $^1$MLCT band at 494 nm and the appearance of a peak with maximum at 518 nm (FIG. 25). The isosbestic points observed at 444 and 506 nm for the process are indicative of the formation of a single species, assigned as the mono-aqua complex, cis-[Ru(bpy)(biq)(CH$_3$CN)(H$_2$O)]$^{2+}$, 12.4. The red shift of the MLCT maximum from 12.1 to 12.4 is similar to that previously reported between [Ru(bpy)$_2$(CH$_3$CN)$_2$]$^{2+}$ and [Ru(bpy)$_2$(CH$_3$CN)(H$_2$O)]$^{2+}$. Continued irradiation with $\lambda_{irr} \geq 550$ nm results in negligible spectral changes and only at very long irradiation times, with the growth of a small shoulder at ~560 nm apparent after 3 hr associated with the formation of a small amount of [Ru(biq)(phen)(H$_2$O)$_2$]$^{2+}$ (12.5). In contrast, when 12.1 is irradiated in H$_2$O with higher energy light, $\lambda_{irr} \geq 420$ nm, the formation of the 12.5 is complete within 6 hours. The 2,192 cm$^{-1}$ red-shift of the MLCT band observed from 12.1 to 12.5 is of the same magnitude as that reported between [Ru(bpy)$_2$(CH$_3$CN)$_2$]$^{2+}$ and [Ru(bpy)$_2$(H$_2$O)$_2$]$^{2+}$, 3,121 cm$^{-1}$.

It is evident in FIG. 25 that irradiation of complex 12.1 in H$_2$O for 20 min ($\lambda_{irr} \geq 550$ nm) results in a well-defined absorption peak with maximum at 518 nm, attributed to the mono-aqua intermediate 12.4, with negligible spectral changes with continued irradiation with this wavelength. However, when 12.4 is further irradiated with higher energy light ($\lambda_{irr} \geq 420$ nm), the bis-aqua species, 12.5, is formed after 3 hours. The mono-aqua intermediate 12.4, produced by the photolysis of 12.1 in H$_2$O ($\lambda_{irr} \geq 550$ nm, FIG. 25) is stable in the dark for up to 6 hours at room temperature (~22° C.).

In contrast to the results described 12.1, irradiation of 12.2 ($\lambda_{irr} \geq 455$ nm, FIG. 26a) and 3 ($\lambda_{irr} \geq 610$ nm, FIG. 26b) results in complete conversion to the corresponding bis-aqua species. The intermediate peak corresponding the mono-aqua species associated with each complex is nearly unidentifiable (FIG. 26), in agreement with the $^1$H NMR photolysis data in CD$_3$CN. These results indicate that in 12.2 and 12.3 both CH$_3$CN ligands exchange relatively easily, whereas in 12.1 one of the CH$_3$CN ligands is significantly more photolabile than the other.

The quantum yields for the first ligand exchange of 12.1 in H$_2$O to generate 12.4 with 500 nm and 550 nm irradiation, $\Phi_{500}^{12.1 \rightarrow 12.4}$ and $\Phi_{550}^{12.1 \rightarrow 12.4}$, were measured to be 0.26(1) and 0.140(5), respectively. These values are similar to those obtained for the formation of the mono-aqua species from 12.3, $\Phi_{500}$=0.24(1) and $\Phi_{550}$=0.150(8), as well as from 12.2, $\Phi_{400}$=0.22(1). However, the quantum yield measured for the exchange of the remaining CH$_3$CN ligand from 12.4 to generate the bis-aqua complex 12.5 were significantly lower, $\Phi_{400}^{12.4 \rightarrow 12.5}$=0.0045(1) and $\Phi_{550}^{12.4 \rightarrow 12.5}$ 0.0014(5). These results differ from those for systems, such as [Ru(bpy)(CH$_3$CN)$_4$]$^{2+}$ and [Ru(bpy)$_2$(CH$_3$CN)$_2$]$^{2+}$, for which the quantum yield of the second photoinduced CH$_3$CN ligand exchange is approximately half the value of the first. This comparison points to a selective ligand exchange in 12.1 that is not present in the symmetric complexes 12.2 and 12.3.

In order to unequivocally assign which CH$_3$CN ligand of 12.1 is more photolabile, a photolysis intermediate was isolated and its structure was determined by X-ray crystallography. A mixture of pyridine (py) and CH$_3$CN (50:50, v:v) was used as the solvent rather than H$_2$O because py is a stronger coordinating ligand than H$_2$O, such that a more stable photolysis product was expected. In order to ensure the formation of the mono-substituted intermediate, a 550 nm bandpass filter was used, and the sample was irradiated until no additional changes in the absorption spectrum were apparent following the shift of the MLCT peak from 497 nm to 523 nm accompanied by a change in color from orange to red. After the photolysis was complete, the solution was concentrated and the [Ru(phen)(biq)(CH$_3$CN)(py)]$^{2+}$ (12.6) product was precipitated by the addition of ether. Slow evaporation of a solvent mixture of acetone, THF, and CH$_3$CN and diethyl ether resulted in red crystals suitable for X-ray diffraction. The single crystals of the intermediate were suitable for X-ray structure determination and the resulting ORTEP diagram is shown in FIG. 27. It is evident from the two different views of the structure of 12.6 shown in FIG. 27 that the py exchanged with the CH$_3$CN ligand positioned trans to the phen ligand (CH$_3$CN$^2$ in Scheme 12.2) with 80% occupancy, clearly indicated that this is more photolabile ligand in complex 12.1. For the remaining 20% occupancy, both CH$_3$CN ligands were solved to be replaced by pyridine and the overall structure is a result of co-crystallization.

In order to confirm that the crystal structure of 12.6 accurately depicts the intermediate in solution, the photolysis ($\lambda_{irr} \geq 550$ nm) of complex 12.1 was carried out in deuterated pyridine (py-d$_5$) and was followed by $^1$H NMR spectroscopy. Upon irradiation up to 20 minutes, the two resonances corresponding each bound CH$_3$CN ligands at 2.35 and 2.75 ppm decrease in intensity, with the concomitant growth of resonances at 2.95 and 1.84 ppm which integrate to 3H each. The former correspond to the remaining bound CH$_3$CN ligand in the mono-substituted intermediate, [Ru(biq)(phen)(CH$_3$CN)(py-d$_5$)]$^{2+}$, and the latter to free CH$_3$CN in py-d$_5$. Further irradiation results in a decrease in the 2.95 ppm peak of the intermediate and an increase in free CH$_3$CN resonance to form the bis-substituted product, [Ru(biq)(phen)(py-d$_5$)$_2$]$^{2+}$. The appearance of only one resonance associated with the intermediate indicates that only one of the bound $CH_3CN$ ligands exchanges first, followed by the second, making the crystal structure of 12.6 shown in FIG. 27 an accurate representation of the mono-substituted species.

Calculations. In order gain further understanding on the selective ligand photosubstitution of 12.1, density functional theory (DFT) calculations were performed. The highest occupied molecular orbitals (HOMOs) of all three complexes, 12.1-12.3, are calculated to be localized on the d-orbitals of the metal, as is typical of Ru(II) diimine complexes. The LUMO (lowest unoccupied molecular orbital) of 12.1 exhibits electron density on the biq ligand and the LUMO+1 is localized on phen, as expected from the ease of reduction of biq relative to phen. When analyzing the unoccupied orbitals in 12.2 and 12.3, the LUMOs are delocalized over both equivalent aromatic ligands of each complex, phen and biq, respectively.

Time-dependent DFT (TD-DFT) calculations reveal that the lowest vertical singlet excited states of 12.1 and 12.3 possess significant contribution, ~95%, from HOMO→LUMO transitions, but low oscillator strengths, with maxima at 476 nm (f=0.0002) and 496 nm (f=0.0008), respectively. More intense absorption bands are predicted at 443 nm (f=0.0646) for 12.1 and at 475 nm (f=0.1015) for 12.3, calculated to possess 67% and 94% contribution from HOMO-1→LUMO transitions, respectively. The lowest energy vertical singlet excited states of 12.2 are calculated at 396 nm (81% HOMO→LUMO+1, f=0.0024) and at 395 nm (91% HOMO→LUMO, f=0.0093). It should be noted that the lowest energy electronic transitions predicted are slightly blue shifted relative to the experimental MLCT maxima, as is typical for DFT calculations.

In order to understand the selective ligand exchange in 12.1, the electron density of the orbitals with greatest contribution to the lowest energy excited state need to be considered, the HOMO and the LUMO. In the lowest energy singlet excited state, electron density is removed from the HOMO, which possesses a bonding interaction between the metal d-orbital and the $CH_3CN$ ligand positioned trans to the phen ligand. Therefore, the HOMO is involved in π-back bonding with $CH_3CN$, and removal of an electron from this MO is expected to weaken the bond. The LUMO of 12.1 is localized on the π* orbital of the biq ligand; placing electron density in this orbital is expected to strengthen the π-bond to the $CH_3CN$ positioned trans to biq.

Moreover, it has been reported that placing additional electron density on the bidentate ligand in the MLCT state of Re(I) carbonyl complexes, such as in $[Re(bpy)(CO)_3(PR_3)]^+$ results in photoinduced ligand dissociation of the CO ligand positioned cis to bpy. Similarly, selective photoinduced ligand exchange of the axial ligands in $[Ru(bpy)(CH_3CN)_4]^{2+}$ and $[Ru(tpy)(CH_3CN)_3]^{2+}$ was observed, where the $CH_3CN$ ligands trans to the diimine, for which the π-backbonding is strengthen, do not exchange, but those positioned cis to the bpy or tpy ligand, respectively, are photolabile. Since the LUMOs of 12.2 and 12.3 are delocalized equally over both diimine ligands in 12.2 and 12.3 ligands, this selectivity is not observed. Furthermore, a greater amount of energy is required to populate the $Ru(t_{2g}) \rightarrow phen(\pi^*)$ MLCT singlet excited state in 12.1 than the $Ru(t_{2g}) \rightarrow biq(\pi^*)$ MLCT singlet excited state. This could be a factor in the enhanced selectivity using lower energy light in which only the $Ru(t_{2g}) \rightarrow biq(\pi^*)$ state is accessed yielding ligand loss of the $CH_3CN$ trans to the phen ligand while higher energy light results in an increased rate for both $CH_3CN$ ligands due to the direct population of the $Ru(t_{2g}) \rightarrow phen(\pi^*)$ state.

It should also be noted that the lowest energy triplet state of 12.1 resulting from the vertical transition from the minimized singlet ground state was calculated to be $^3$MLCT Ru→biq in nature, similar to the lowest energy singlet excited state.

Additionally, the photoinduced ligand exchange is expected to occur via a dissociative mechanism, such that the ligand exchange in 12.1 is expected to proceed through a five-coordinate intermediate to produce the monosubstituted product, 12.4. Optimization of the five coordinate species, $[Ru(biq)(phen)(CH_3CN)]^{2+}$, starting from a trigonal bipyramidal geometry results in a distorted square pyramidal geometry with an open site for coordination positioned trans to the phen ligand. This result is consistent with the observation of the intermediate 12.6 (FIG. 27), where the $CH_3CN$ ligand trans to phen was photosubstituted. In addition, both possible monosubstituted products were optimized, with py trans to phen and trans to biq. When the py replaced the $CH_3CN$ trans to the phen ligand, the overall energy is more stable by 11 kJ/mol relative that trans to the biq, such that the former is thermodynamically favored.

Conclusions. The series of Ru(II) complexes 12.1-12.3 possess two $CH_3CN$ ligands in a cis-disposition and undergo photodinduced ligand exchange with solvent or coordinating molecules in solution when irradiated with visible light. Selective $CH_3CN$ ligand exchange takes place in the asymmetric complex 12.1 with low energy irradiation ($\lambda_{irr} \geq 550$ nm), where only one of the ligands is photolabile. This selectivity is not observed in the symmetric complexes 12.2 and 12.3. A crystal structure of the $PF_6^{-1}$ salt of the mono-substituted intermediate $[Ru(biq)(phen)(CH_3CN)(py)]^{2+}$ (12.6), was obtained as the product of the photolysis of 12.1 in a py:$CH_3CN$ solvent mixture, showing the selective exchange of the $CH_3CN$ ligand trans to phen. DFT calculations show that the lowest energy $^1$MLCT and $^3$MLCT states of 12.1 are characterized by a decrease of electron density in a Ru—$CH_3CN$ π-bonding orbital, thus weakening the bond to the $CH_3CN$ ligand trans to phen. The promoted electron is localized on the LUMO with biq(π*) character, strengthening the Ru—$CH_3CN$ bond of the ligand positioned trans to biq. These results point at the direct role of the MLCT states in the photoinduced ligand exchange process. The techniques described herein can be used for the synthesis of heteroleptic inorganic complexes, as well as for a new method of wavelength selective drug delivery in photochemotherapeutic applications.

Example 13

Pharmaceutical Dosage Forms

The following formulations illustrate representative pharmaceutical dosage forms that may be used for the therapeutic or prophylactic administration of a compound of a formula described herein, a compound or complex specifically disclosed herein, or a pharmaceutically acceptable salt or solvate thereof (hereinafter referred to as 'Compound X'):

|  | mg/mL |
| --- | --- |
| (i) Injection 1 (1 mg/mL) | |
| 'Compound X' (free acid form) | 1.0 |
| Dibasic sodium phosphate | 12.0 |
| Monobasic sodium phosphate | 0.7 |
| Sodium chloride | 4.5 |

| | mg/mL |
|---|---|
| 1.0N Sodium hydroxide solution (pH adjustment to 7.0-7.5) | q.s. |
| Water for injection | q.s. ad 1 mL |
| (ii) Injection 2 (10 mg/mL) | |
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |
| (iii) Aerosol | mg/can |
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (iii) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula IA:

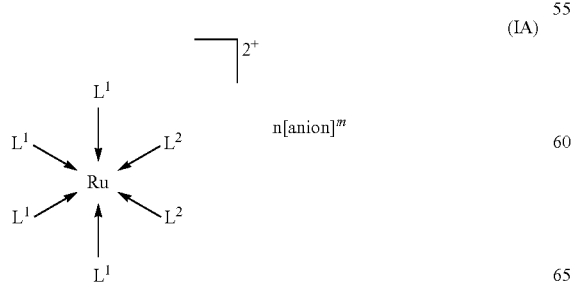

(IA)

wherein
Ru is ruthenium;
each $L^2$ is a protease inhibitor having a —C≡N— bonded to Ru through the nitrogen of the —C≡N—, wherein the protease inhibitor is a cysteine protease inhibitor, a cathepsin protease inhibitor, a serine protease inhibitor, or an aspartic protease inhibitor; or
one $L^2$ is a protease inhibitor having a —C≡N— bonded to Ru through the nitrogen of the —C≡N—, wherein the protease inhibitor is a cysteine protease inhibitor, a cathepsin protease inhibitor, a serine protease inhibitor, or an aspartic protease inhibitor, and the other $L^2$ is a solvent molecule coordinated to ruthenium;
each $L^1$ is independently a nitrogen-containing ruthenium ligand, optionally connected to one or more other $L^1$ groups to form a multidentate ruthenium ligand or a solvent molecule;
wherein one $L^1$ group optionally forms a monodentate ligand, two $L^1$ groups optionally form a bidentate ruthenium ligand, three $L^1$ groups optionally form a tridentate ruthenium ligand, or four $L^1$ groups optionally form a tetradentate ruthenium ligand; and
n[anion]$^m$ is a pharmaceutically acceptable anion where n is 2 and m is −1, or n is 1 and m is −2.

2. The compound of claim 1, wherein the protease inhibitor having a —C≡N— bonded to the Ru is balicatib, L-006235, L-873724, MK-1256, nilvadipine, odanacatib, saxagliptin, or vildagliptin.

3. The compound of claim 1, wherein the protease inhibitor having a —C≡N— bonded to the Ru is:

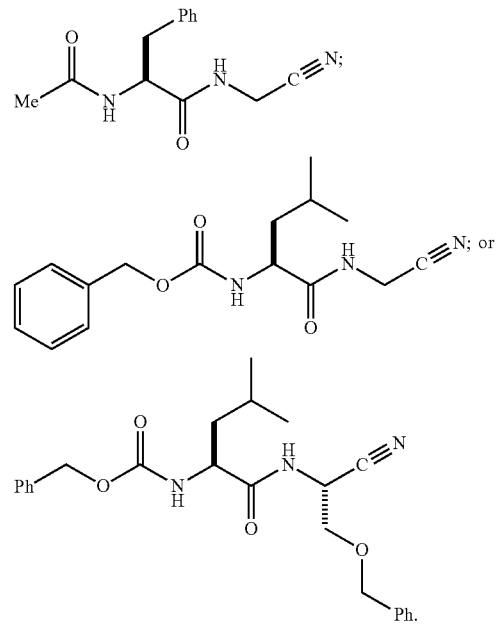

4. The compound of claim 1 wherein:
a) Formula IA comprises two 2,2'-bipyridine (bpy) ligands;
b) Formula IA comprises two 1,10-phenanthroline (phen) ligands;
c) Formula IA comprises two 2,2'-biquinoline (biq) ligands;
d) Formula IA comprises a 2,2'-biquinoline (biq) ligand and a 1,10-phenanthroline (phen) ligand;
e) Formula IA comprises three $L^1$ groups to form a terpyridine (tpy) ligand; or f) Formula IA comprises a tri(2-methylpyridyl)amine (TPA) ligand.

5. The compound of claim 1, wherein the compound of Formula IA is a compound of Formula XI-A, wherein the compound of Formula XI-A is:

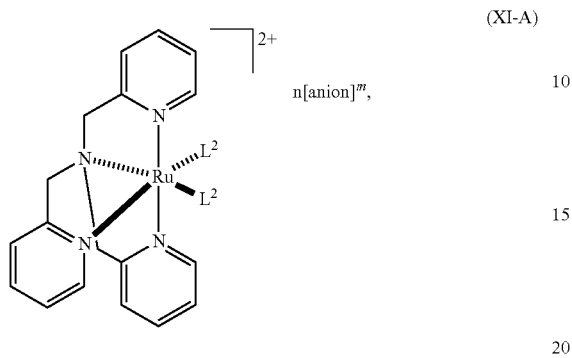

(XI-A)

wherein Formula XI-A comprises a tri(2-methylpyridyl)amine (TPA) ligand.

6. The compound of claim 1 wherein n[anion]$^m$ is 2PF$_6^-$.

7. The compound of claim 1, having a light:dark ratio of the IC$_{50}$ values (μM) of from 5 to 150 for human cathepsins.

8. The compound of claim 7 having a light:dark ratio of the IC$_{50}$ values (μM) of from 6 to 15 for human cathepsins.

9. A pharmaceutical composition comprising a compound of claim 1 or 3, and a pharmaceutically acceptable excipient, diluent, or carrier.

* * * * *